(12) United States Patent
Chisholm et al.

(10) Patent No.: US 8,372,384 B2
(45) Date of Patent: Feb. 12, 2013

(54) QUATERNARY AMMONIUM FUNCTIONALIZED CROSS-LINKED POLYALKYLSILOXANES WITH ANTI-FOULING ACTIVITY

(75) Inventors: Bret Ja Chisholm, West Fargo, ND (US); Partha Majumdar, Fargo, ND (US); Shane J. Stafslien, West Fargo, ND (US); Philip Boudjouk, Fargo, ND (US)

(73) Assignee: NDSU Research Foundation, Fargo, ND (US)

( * ) Notice: Subject to any disclaimer, the term of this patent is extended or adjusted under 35 U.S.C. 154(b) by 1251 days.

(21) Appl. No.: 12/006,926

(22) Filed: Jan. 7, 2008

(65) Prior Publication Data

US 2008/0181862 A1    Jul. 31, 2008

Related U.S. Application Data

(60) Provisional application No. 61/005,719, filed on Dec. 7, 2007, provisional application No. 60/995,918, filed on Sep. 28, 2007, provisional application No. 60/879,313, filed on Jan. 8, 2007.

(51) Int. Cl.
*A61K 31/74* (2006.01)
(52) U.S. Cl. .................................................. 424/78.09
(58) Field of Classification Search ........................ None
See application file for complete search history.

(56) References Cited

U.S. PATENT DOCUMENTS

| | | | |
|---|---|---|---|
| 4,125,491 A | 11/1978 | Gorman | |
| 4,298,543 A | 11/1981 | Law et al. | |
| 4,400,288 A * | 8/1983 | Dhanani et al. | 510/347 |
| 4,417,066 A * | 11/1983 | Westall | 556/425 |
| 4,687,813 A | 8/1987 | Lenz et al. | |
| 4,697,913 A | 10/1987 | Kuramoto et al. | |
| 4,895,964 A * | 1/1990 | Margida | 556/425 |
| 4,902,767 A | 2/1990 | Roitman et al. | |
| 4,910,252 A | 3/1990 | Yonehara et al. | |
| 4,933,178 A | 6/1990 | Capelli | |
| 4,996,257 A | 2/1991 | Saito et al. | |
| 5,001,210 A | 3/1991 | Coury et al. | |
| 5,019,096 A | 5/1991 | Fox, Jr. et al. | |
| 5,203,991 A | 4/1993 | Kutsuna et al. | |
| 5,225,190 A | 7/1993 | Halloran et al. | |
| 5,237,082 A | 8/1993 | Leir et al. | |
| 5,260,400 A | 11/1993 | Karydas | |
| 5,602,224 A | 2/1997 | Vrckovnik et al. | |

(Continued)

FOREIGN PATENT DOCUMENTS

| CA | 2 413 672 A1 | 8/2003 |
|---|---|---|
| CA | 2621000 | 3/2007 |

(Continued)

OTHER PUBLICATIONS

Japanese Patent Abstract for Japanese Publication No. JP 2003-327912, "Primer Antifouling Coating Material Composition for Ship, Composite Antifouling Coating Film for Ship, Method for Forming the Composite Antifouilng Coating Film, Ship Coated with the Composite Antifouilng Coating Film and Antifouling Method for Outer Hull of Ship", date of publication Nov. 19, 2003.

(Continued)

*Primary Examiner* — Paul Dickinson
(74) *Attorney, Agent, or Firm* — Foley & Lardner LLP

(57) ABSTRACT

Functionalized cross-linked polysiloxanes, such as quaternary ammonium terminated cross-linked polyalkylsiloxanes are described herein. The functionalized cross-linked polysiloxanes may be used in an antifouling composition to prevent biological fouling in aqueous and/or marine environments.

28 Claims, 32 Drawing Sheets

U.S. PATENT DOCUMENTS

| | | | |
|---|---|---|---|
| 5,641,855 A | 6/1997 | Scherr et al. | |
| 5,986,018 A | 11/1999 | Yamaguchi et al. | |
| 6,030,632 A | 2/2000 | Sawan et al. | |
| 6,099,897 A | 8/2000 | Sayo et al. | |
| 6,153,724 A | 11/2000 | Hollingsworth | |
| 6,224,579 B1 | 5/2001 | Modak et al. | |
| 6,369,186 B1 | 4/2002 | Branlard et al. | |
| 6,387,997 B1 | 5/2002 | Grolemund et al. | |
| 6,413,446 B1 | 7/2002 | Mechtel et al. | |
| 6,451,437 B1 | 9/2002 | Amidaiji et al. | |
| 6,458,878 B1 | 10/2002 | Tsuboi et al. | |
| 6,482,912 B2 | 11/2002 | Boudjouk et al. | |
| 6,500,549 B1 | 12/2002 | Deppisch et al. | |
| 6,524,564 B1 | 2/2003 | Kim et al. | |
| 6,559,201 B2 | 5/2003 | Simendinger, III | |
| 6,565,924 B2 * | 5/2003 | Babu et al. | 427/344 |
| 6,716,895 B1 | 4/2004 | Terry | |
| 6,723,439 B2 | 4/2004 | Amidaiji et al. | |
| 6,861,493 B2 | 3/2005 | Bauer et al. | |
| 6,949,598 B2 | 9/2005 | Terry | |
| 7,098,256 B2 | 8/2006 | Ong et al. | |
| 7,141,183 B2 | 11/2006 | Hattori et al. | |
| 7,179,789 B2 | 2/2007 | Patt | |
| 7,204,940 B2 | 4/2007 | McDonald et al. | |
| 7,235,230 B2 | 6/2007 | LeGrow et al. | |
| 7,265,194 B1 | 9/2007 | Lichtenhan et al. | |
| 7,297,745 B2 | 11/2007 | Amidaiji et al. | |
| 7,345,131 B2 | 3/2008 | Selbertinger et al. | |
| 7,378,156 B2 | 5/2008 | Terry | |
| 7,449,537 B2 | 11/2008 | Boudjouk et al. | |
| 7,452,956 B2 | 11/2008 | Cheng et al. | |
| 7,544,722 B2 | 6/2009 | Boudjouk et al. | |
| 7,989,074 B2 | 8/2011 | Webster et al. | |
| 8,053,535 B2 | 11/2011 | Boudjouk et al. | |
| 8,062,729 B2 | 11/2011 | Webster et al. | |
| 8,071,706 B2 | 12/2011 | Stafslien et al. | |
| 8,278,400 B2 | 10/2012 | Chisholm et al. | |
| 8,283,432 B2 | 10/2012 | Stafslien et al. | |
| 8,299,200 B2 | 10/2012 | Webster et al. | |
| 2002/0013385 A1 | 1/2002 | Simendinger, III | |
| 2002/0098214 A1 | 7/2002 | Adams et al. | |
| 2002/0156223 A1 | 10/2002 | Boudjouk et al. | |
| 2003/0022793 A1 | 1/2003 | Ring et al. | |
| 2003/0044451 A1 | 3/2003 | McGhee et al. | |
| 2003/0129421 A1 | 7/2003 | Terauchi et al. | |
| 2003/0207962 A1 | 11/2003 | Oya et al. | |
| 2003/0236552 A1 | 12/2003 | Roby | |
| 2004/0116551 A1 | 6/2004 | Terry | |
| 2005/0008613 A1 | 1/2005 | Peterson et al. | |
| 2005/0009953 A1 | 1/2005 | Shea | |
| 2005/0009985 A1 | 1/2005 | Selbertinger et al. | |
| 2005/0080158 A1 | 4/2005 | Ong et al. | |
| 2005/0129962 A1 | 6/2005 | Amidaiji et al. | |
| 2005/0227092 A1 | 10/2005 | Yamaya et al. | |
| 2006/0014015 A1 | 1/2006 | Travelute et al. | |
| 2006/0223969 A1 | 10/2006 | Roesler et al. | |
| 2006/0252094 A1 | 11/2006 | Zhou et al. | |
| 2006/0276608 A1 | 12/2006 | Lang et al. | |
| 2007/0021529 A1 | 1/2007 | Boudjouk et al. | |
| 2007/0032626 A1 | 2/2007 | Roesler et al. | |
| 2007/0042199 A1 | 2/2007 | Chisholm et al. | |
| 2007/0048344 A1 | 3/2007 | Yahiaoui et al. | |
| 2007/0093618 A1 | 4/2007 | Cheng et al. | |
| 2007/0112161 A1 | 5/2007 | Roesler et al. | |
| 2007/0112164 A1 | 5/2007 | Roesler et al. | |
| 2007/0129474 A1 | 6/2007 | Salamone et al. | |
| 2007/0132949 A1 | 6/2007 | Phelan | |
| 2008/0001318 A1 * | 1/2008 | Schorzman et al. | 264/1.32 |
| 2008/0112920 A1 | 5/2008 | Chia et al. | |
| 2008/0181862 A1 | 7/2008 | Chisholm et al. | |
| 2008/0199536 A1 | 8/2008 | Terry | |
| 2008/0213599 A1 | 9/2008 | Webster et al. | |
| 2009/0018276 A1 | 1/2009 | Boudjouk et al. | |
| 2009/0111937 A1 | 4/2009 | Webster et al. | |
| 2009/0143496 A1 | 6/2009 | Ziche | |
| 2009/0194733 A1 | 8/2009 | Schulz et al. | |
| 2009/0215762 A1 | 8/2009 | Stafslien et al. | |
| 2010/0004202 A1 | 1/2010 | Chisholm et al. | |
| 2010/0204399 A1 | 8/2010 | Chisholm et al. | |
| 2010/0280148 A1 | 11/2010 | Webster et al. | |
| 2011/0236343 A1 | 9/2011 | Chisholm et al. | |

FOREIGN PATENT DOCUMENTS

| | | |
|---|---|---|
| EP | 1 496 079 A1 | 1/2005 |
| JP | 02047371 | 2/1990 |
| WO | WO 2005/030405 A2 | 4/2005 |
| WO | WO 2006/086092 A2 | 8/2006 |
| WO | WO 2006/121937 A1 | 11/2006 |
| WO | WO 2007/053163 A2 | 5/2007 |
| WO | WO 2008/008077 A2 | 1/2008 |
| WO | WO 2009/025924 A2 | 2/2009 |

OTHER PUBLICATIONS

Japanese Patent Abstract for Japanese Publication No. JP 63-270738, "Polyamine/Polysiloxane Block Copolymer", date of publication Nov. 8, 1988.

Japanese Patent Abstract for Japanese Publication No. JP 53-139653, "Marine Antifouling Material", date of publication Dec. 6, 1978.

Abstract for Japanese Publication No. JP 11-222402, Publication Date Aug. 17, 1999, Patentee or Applicant listed as Osaka Gas Co. Ltd., 1 page.

U.S. Appl. No. 12/633,334, filed Dec. 7, 2009, Webster et al.

U.S. Appl. No. 60/934,093, filed Jun. 11, 2007, Webster et al.

U.S. Appl. No. 11/810,696, filed Jun. 6, 2007, Webster et al.

Abstract for Japanese Publication No. JP 2001-029451 (A), "Antibacterial Urethral Catheter and Manufacture of the same," Toyo Boseki et al., publication date Feb. 6, 2001, 1 page.

Abstract for JP 2000-264803, "Silver Microbide-Containing Photopolymerizable Monomer Compositions, and Solventless UV- or Electron Beam-Curable Resin Compositions Containing Them," Takeuchi et al., publication date Sep. 26, 2000, 1 page.

Abstract for JP 51-17554, "UV-Curable Antimicrobial Acrylic Coating Materials," Honda et al., publication date May 14, 1993, 1 page.

Abstract for JP 60-09919, "Crosslinked Urethane Acrylate Polymer Particle-Containing Antimicrobial Coatings," Honda et al., publication date Jan. 18, 1994, 1 page.

Adhikari et al., "Mixed Macrodiol-Based Siloxane Polyurethanes: Effect of the Comacrodiol Structure on Properties and Morphology," *Journal of Applied Polymer Science*, 2000, vol. 78, pp. 1071-1082.

Bullock et al., "Surface Science of a Filled Polydimethylsiloxane-Based Alkoxysilane-Cured Elastomer: RTV11[1.]" *Journal of Colloid and Interface Science*, 1999, vol. 210, pp. 18-36, Article ID jcis.1998. 5856, available online at http://www.idealibrary.com.

Chen et al., "*Macromolecules*," 1995, vol. 28, pp. 1635-1642.

Chen et al., "Solvent Effects on the Surface Composition of Poly(dimethylsiloxane) -co-Polystyrene/Polystyrene Blends," *Macromolecules*, 1998, vol. 31, No. 26, pp. 9328-9336.

El-Hayek et al., Bacteriostatic polymer film immobilization. *Journal of biomedical materials research*. Part A 2006, vol. 79 No. 4, pp. 874-881 (Plus Cover Sheet, 9 pages total).

Ha et al., *Journal of Macromolecular Science, Polymer Reviews*, 2005, vol. C45, 32 pgs.

Ho et al., "Polydimethylsiloxane-Urea-Urethane Copolymers with 1,4-Benzenedimethanol as Chain Extender," *Macromolecules*, 1993, vol. 26, No. 25, pp. 7029-7036.

Holohan et al., "Monofunctional polydimethylsiloxane oligomers for graft copolymerization," *Macromol. Chem. Phys.*, 1994, vol. 195, No. 9, pp. 2965-2979 (Plus cover Sheet, 16 pages total).

Iojoiu et al., "Modified poly (ε-caprolactone)s and their use for drug-encapsulating nanoparticles," Journal of Polymer Science Part A: Polymer chemistry, 2004, vol. 42, No. 3, pp. 689-700.

Jiang et al., Preparation of crosslinked polystyrenes with quaternary ammonium and their antibacterial behavior *Reactive & Functional Polymers 2005*, vol. 62, 5 pages.

Johnston et al., "Networks from α,ω-Dihydroxypoly(dimethylsiloxane) and (Tridecafluoro-1,1,2,2-tetrahydrooctyl)triethoxysilane: Surface Microstructures and Surface Characterization," *Macromolecules*, 1999, vol. 32, No. 24, pp. 8173-8182.

Karal et al., "Blend of polycaprolactone-poly (dimethylsiloxane)-polycaprolactone triblock copolymer with poly(vinyl chloride) preparation and characterization," Polymer, 1997, vol. 38, No. 24, pp. 6071-6078.

Kawakami et al., "Silicone Macromers for Graft Polymer Synthesis," Polymer Journal, 1982, vol. 14, No. 11, pp. 913-917.

Lee et al., Journal of Applied Polymer Science, 2003, vol. 87, pp. 375-380.

Lenoir et al., Antimicrobial activity of polystyrene particles coated by photo-crosslinked block copolymers containing a biocidal polymethacrylate block. e-Polymers 2005, 11 pages.

Mahoney et al., Macromolecules, 2002, vol. 35, pp. 5256-5266.

Patel et al., Macromolecules, 1988, vol. 21, pp. 2689-2696.

Pike et al., "Water-Induced Surface Rearrangements of Poly(dimethylsiloxane-urea-urethane) Segmented Block Copolymers," Chem. Mater., 1996, vol. 8, No. 4, pp. 856-860.

Schweizer, Triclosan: a widely used biocide and its link to antibiotics. FEMS Microbiology Letters, 2001, vol. 202, No. 1, pp. 1-7 (Plus Cover Sheet, 9 pages total).

Smetankina et al., "Reactivity of organosilicon diisocyanates," XVII, Carcofunctional organosilicon compounds, Zhurnal Obshchei Khimii, 1974, vol. 44, No. 12, pp. 2638-2641.

Smith et al., Macromolecules, 1992, vol. 25, pp. 2575-2581.

Tanaka, et al., Physical Review Letters, 1992, vol. 68, No. 18, pp. 2794-2797.

Tang et al., "Anti-inflammatory properties of triblock siloxane copolymer-blended materials," Biomaterials, 1999, vol. 20, pp. 1365-1370 (Plus Figure, 6 pages total).

Tezuka et al., "Environmentally induced Macromolecular Rearrangement on the Surface of Polyurethane-Polysiloxane Block Copolymers," J. Chem. Soc. Paraday Trans., 1991, vol. 87, pp. 147-152.

Tezuka et al., "Environmentally Induced Macromolecular Rearrangement on the Surface of Polyurethane-Polysiloxane Graft Copolymers", Journal of Colloid and Interface Science, May 1990, vol. 136, No. 2, pp. 408-414.

Thomas et al., "Silicones Containing Pendant Biocides for Antifouling Coatings," Biofouling, vol. 20, Nos. 4/5, Aug./Oct. 2004, pp. 227-236.

Wynne et al., "Poly(dimethysiloxane)-Urea-Urethane Copolymers," Synthesis and Surface Properties, Chapter 7, Ingoranic and Organometallic Polymers II, Am. Chem. Soc., 1994, pp. 64-80.

Wynne et al., ACS Symposium Series, 1994, vol. 572, pp. 64-80.

Yilgor et al., "Novel triblock siloxane copolymer: Synthesis, characterization, and their use as surface modifying additives," Journal of Polymer Science Part A: Polymer chemistry, 1989, pp. 3673-3690.

Zhuang et al., "Determination of the Distribution of Poly(dimethylsiloxane) Segment Lengths at the Surface of Poly[(dimethylsiloxane)-urethane]-Segmented Copolymers by Time-of-Flight Secondary Ion Mass Spectrometry," Macromolecules, 1997, vol. 30, No. 4, pp. 1153-1157.

U.S. Appl. No. 12/378,155, filed Feb. 11, 2009, Chisholm et al.

U.S. Appl. No. 12/378,049, filed Feb. 10, 2009, Stafslien et al.

Abstract for JP 2007246576 (A), "Water Paint Composition", Matsushita et al., publication date Sep. 27, 2007, (1 pg.).

Casse et al., "Laboratory screening of coating libraries for algal adhesion," Biofouling, 2007, 23(3/4), pp. 267-276.

Ekin et al., "Library Synthesis and Characterization of 3-Aminopropyl-Terminated Poly(dimethylsiloxane)s and Poly(ε-caprolactone)-b-Poly(dimethylsiloxane)s," Journal of Polymer Science: Part A: Polymer Chemistry, 2006, vol. 44(16), pp. 4880-4894.

Ekin et al., "Synthesis and Characterization of Novel Hydroxyalkyl Carbamate and Dihydroxyalkyl Carbamate Terminated Poly(dimethylsiloxane) Oligomers and Their Block Copolymers with Poly(ε-caprolactone)," Macromolecules, 2006, 39(25), pp. 8659-8668.

Ekin et al., "Synthesis, formulation, and characterization of siloxane-polyurethane coatings for underwater marine applications using combinatorial high-throughput experimentation," J. Coat. Technol. Res., 2007, 4(4), pp. 435-451.

Ekin et al., "Combinatorial and High-Throughput Screening of the Effect of Siloxane Composition on the Surface Properties of Crosslinked Siloxane—Polyurethane Coatings, J. Comb. Chem., 2007, 9(1), pp. 178-188.

Majumdar et al., "Preparation of Siloxane-Urethane Coatings Having Spontaneously Formed Stable Biphasic Microtopographical Surfaces," Macromolecules, 2005, vol. 38, pp. 5857-5859.

Majumdar et al., "Thermoset Siloxane-Urethane Fouling Release Coatings," A.C.S. Symposium Series, 2007, vol. 957, pp. 61-75.

Pieper et al., "Combinatorial approach to study the effect of acrylic polyol composition on the properties of crosslinked siloxane-polyurethane fouling-release coatings," J. Coat. Technol. Res., 2007, 4(4), pp. 453-461.

Stafslien et al., "Combinatorial materials research applied to the development of new surface coatings IV. A high-throughput bacterial biofilm retention assay for screening fouling-release performance of coatings," Biofouiing, 2007, 23(1/2), pp. 45-54.

Abstract for Japanese Publication No. JP 04-370163 A, "Coating Composition", date of publication Dec. 22, 1992 (1 pg.).

Abstract for Japanese Publication No. JP 63-277222 A, "Curing Resin", date of publication Nov. 15, 1998 (1 pg.).

Chojnowski et al., "Polysilsesquioxanes and Oligosilsesquioxanes Substituted by Alkylammonium Salts as Antibacterial Biocides," Journal of Inorganic and Organometallic Polymers and Materials, vol. 16. No. 3, Sep. 2006, pp. 219-230.

Extended European Search Report for European Patent Application No. 08779542.3, mailing date Jul. 5, 2011.

Gelest—Reactive Silicones: Forging New Polymer Links, available at least by Aug. 10, 2011, pp. 17-20.

Lligadas et al., "Bionanocomposites from Renewable Resources: Epoxidized Linseed Oil-Polyhedral Oligomeric Silsesquioxanes Hybrid Materials," Biomacromolecules 2006, vol. 7 No. 12, pp. 3521-3526.

Neumann et al., "Synthesis and Characterization of an Isocyanate Functionalized Polyhedral Oligosilsesquioxane and the Subjsequent Formation of an Organic-Inorganic Hybrid Polyurethane," Journal of American Chemical Society, vol. 124, No. 47, 2002, pp. 13998-13999.

Majumdar et al., "Influence of solvent composition and degree of reaction on the formation of surface microtopography in a thermoset siloxane-urethane system," Polymer, vol. 47, 2006, pp. 4172-4181.

Scott, Donald W., "Thermal Rearrangement of Branched-Chain Methylpolysiloxanes," Contribution From The Research Laboratory, General Electric Co., vol. 68, Mar. 1946, pp. 356-358.

Tamaki et al., "Octa(aminophenyl)silsesquioxane as a Nanoconstruction Site," Journal of American Chemical Society, vol. 123, No. 49, 2001, pp. 12416-12417.

Majumdar et al., "Influence of Solvent Composition and Degree of Reaction on the Formation of Surface Microtopography in a Thermoset Siloxane-Urethane System," Polymer, 47, 4172-4181 (2006).

* cited by examiner

PDMS MW 2000

PDMS MW 18000

PDMS MW 49000

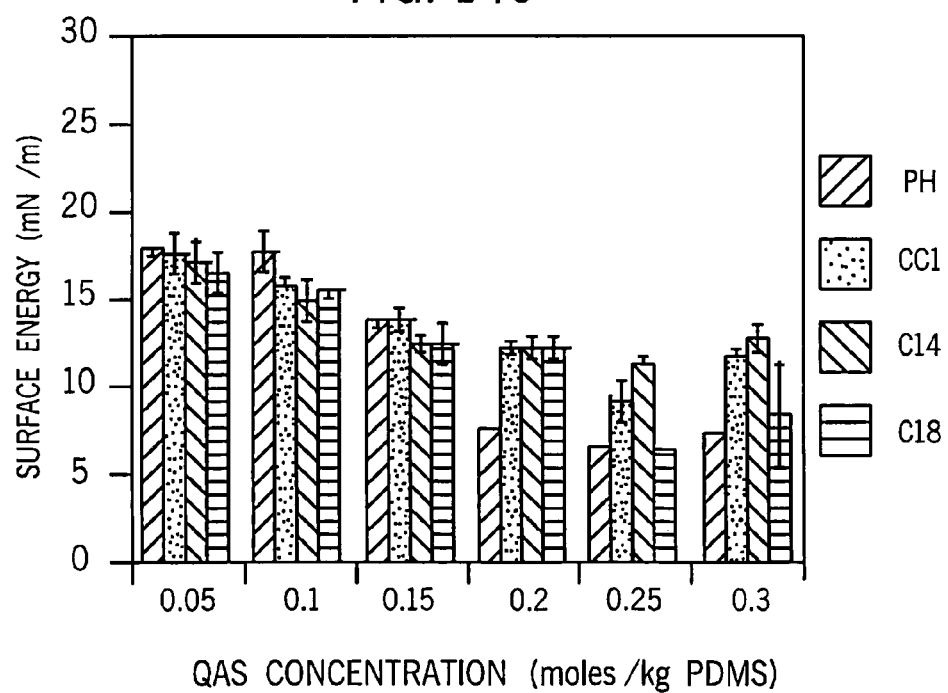

QUATERNARY AMMONIUM FUNCTIONALIZED CROSS-LINKED POLYALKYLSILOXANES WITH ANTI-FOULING ACTIVITY

CROSS-REFERENCE TO RELATED PATENT APPLICATIONS

This application claims priority to U.S. Provisional Patent Application Ser. No. 60/879,313, entitled "Quaternary Ammonium Functionalized Cross-Linked Polyalkylsiloxanes with Anti-Fouling Activity," filed on Jan. 8, 2007, U.S. Provisional Patent Application Ser. No. 60/995,918, entitled "Quaternary Ammonium Functionalized Cross-Linked Polyalkylsiloxanes with Anti-Fouling Activity," filed on Sep. 28, 2007, and to U.S. Provisional Patent Application Ser. No. 61/005,719, entitled "Quaternary Ammonium Functionalized Cross-Linked Polyalkylsiloxanes with Anti-Fouling Activity," filed on Dec. 7, 2007, all of which are expressly incorporated herein by reference in their entireties, as if the complete and entire text and figures, had been included herein.

GOVERNMENT RIGHTS STATEMENT

This invention was made with government support under Grant Nos. N00014-05-1-0822 and N00014-06-1-0952, awarded by the Department of Defense Office of Naval Research. The government has certain rights in the invention.

BACKGROUND

Quaternary ammonium salts (QASs) have been known and widely used for more than half a century as disinfectants. It is now accepted that they exert their biocidal activity by an electrostatic mechanism with the cell wall of bacteria. Surfaces coated with QAS-containing polymers retained their activity over a longer period of time. Polysiloxanes with QAS groups were attractive as biocidal polymers as polysiloxanes have high chain flexibility which allows easier contact between microorganisms and QAS. QASs with long alkyl chains were good candidates for this function. Structure, density, and distribution of QASs in the polymer matrix could affect their biocidal activity. A typical coating formulation containing QAS has large number of variables including the types of QASs, their levels of addition, molecular weight of polysiloxanes, levels of catalyst, and the amount of crosslinker.

SUMMARY

The present application relates to functionalized cross-linked polysiloxanes, which may be useful in a variety of applications involving inhibition of biofilm growth on a substrate, inhibition of biofilm retention on a substrate, facilitation of biofilm removal from a surface, antimicrobial activity, and/or antifouling activity. For example, a substrate may be formed having an antifouling coating on a surface thereof, where the coating comprises a polymeric material which includes quaternary amino functionalized cross-linked polysiloxane. The functionalized cross-linked polysiloxanes may be used in an antifouling composition to prevent biological fouling in aqueous and/or marine environments and/or may be used in coatings where antimicrobial properties are desirable.

In one embodiment, the quaternary amino functionalized cross-linked polysiloxane is prepared by reacting a mixture which includes alkoxysilyl functionalized quaternary amine and silanol terminated polysiloxane. The mixture may further comprise a tetra-functional acyloxysilane and/or alkoxysilane, e.g., an alkyltriacyloxysilane. In other embodiments, the mixture may comprise a trifunctional silane, e.g., in which the reactive functionality is selected from the group consisting of alkoxysilane, acyloxysilane, silazane, halosilane, and ketoxime-based silane. The alkoxysilyl functionalized quaternary amine may include a compound of the structure

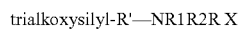

wherein R1 and R2 are lower alkyl, R' is alkylene and X is a halide. In other embodiments, the alkoxysilyl functionalized quaternary amine may include a bis-(alkoxysilyl functionalized)-quaternary amine, e.g., where the quaternary amino functional group is a tetraalkyl quaternary amino group. In some embodiments, the mixture used to produce the quaternary amino functionalized cross-linked polysiloxane may also include a filler, such as silica. For example, suitable cross-linked polysiloxanes may be prepared by reacting a mixture which includes alkoxysilyl functionalized quaternary amine, silanol terminated polysiloxane and up top about 25 wt. % and, more suitably about 5 to 15 wt. % silica.

In other embodiments, a method of inhibiting biofilm retention on a substrate surface, comprising coating the surface with the polymeric material, which includes the quaternary amino functionalized cross-linked polysiloxane, is provided.

In other embodiments, a method of inhibiting biofilm growth on a substrate surface comprising coating the surface with the polymeric material, which includes the quaternary amino functionalized cross-linked polysiloxane, is provided.

In yet other embodiments, a method of facilitating biofilm removal from a substrate surface, comprising coating the surface with the polymeric material, which includes the quaternary amino functionalized cross-linked polysiloxane, is provided.

In some embodiments, a method of forming an antifouling coating on a surface of a substrate comprising coating the surface with the polymeric material, which includes the quaternary amino functionalized cross-linked polysiloxane, is provided.

In some embodiments, a method of forming an antimicrobial polymer coating on a surface of a substrate comprising coating the surface with the polymeric material, which includes the quaternary amino functionalized cross-linked polysiloxane, is provided.

DETAILED DESCRIPTION

Figure 1:
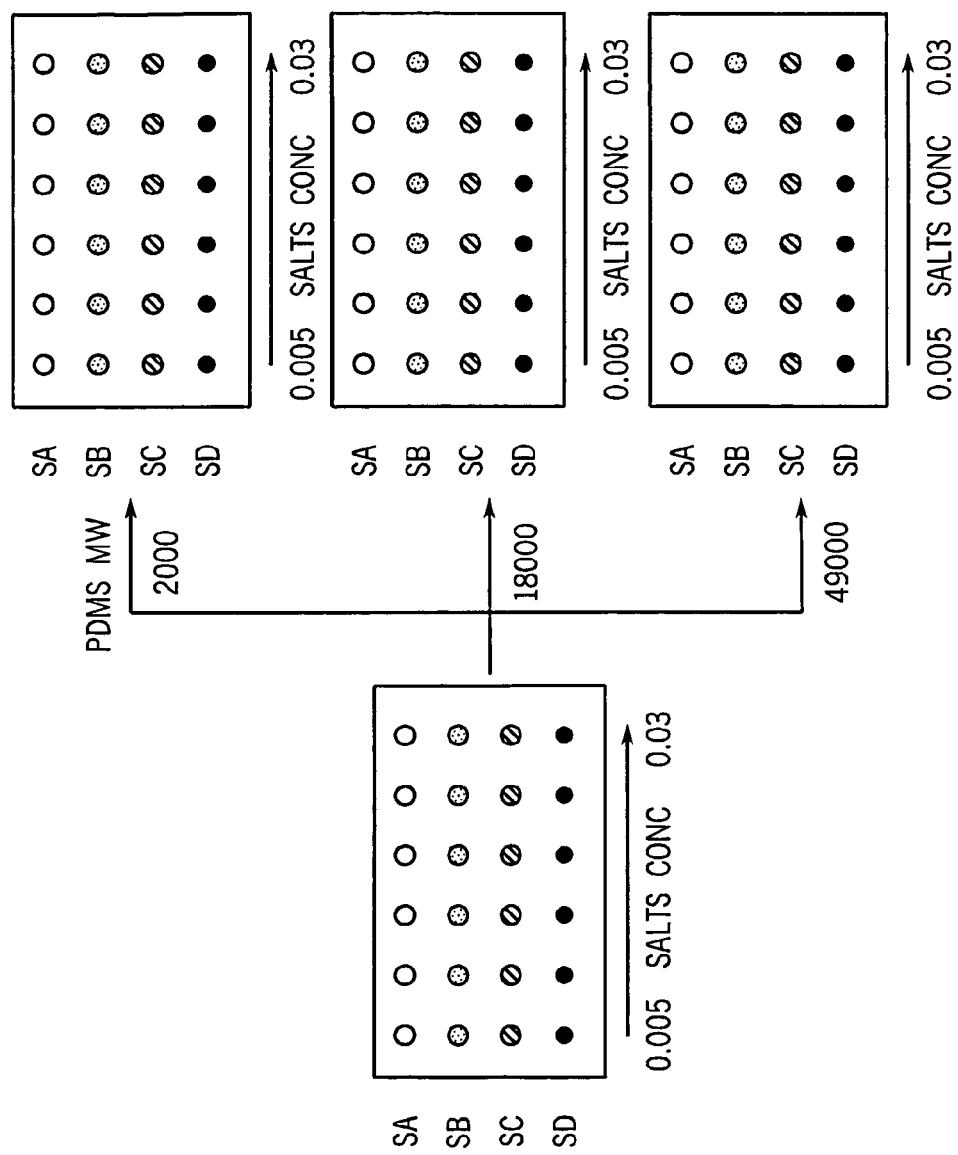
FIG. 1 shows a library design based on four types of QASs and three types of PDMS.

A high-throughput combinatorial approach was taken to develop anti-fouling coating formulations based on three different silanol terminated polydimethylsiloxanes, four different QASs, and levels of addition of QASs. The initial screening of these coatings was performed after one month artificial sea water immersion in order to determine the stability against delaminating from the substrate.

Materials. Silanol terminated polydimethylsiloxane (PDMS) of molecular weight 2000 (DMS-S15), silanol terminated polydimethylsiloxane of molecular weight 18000 (DMS-S27), silanol terminated polydimethylsiloxane of molecular weight 49000 (DMS-S35), n-(trimethoxysilylethyl)benzyl-n,n,n-trimethylammoniumchloride (SIT8395, SA), tetradecyldimethyl(3-trimethoxysilylpropyl)ammoniumchloride (SIT7090, SB), n-trimethoxysilylpropyl-n,n,n-trimethylammoniumchloride (SIT8415, SC), octadecyldimethyl(3-trimethoxysilylpropyl)ammoniumchloride (SIO6620, SD), and methyltriacetoxysilane (SIM6519) were purchased from Gelest. 1.0 M tetrabutylammoniumfluoride (TBAF) in tetrahydrofurane was obtained from Aldrich. Toluene was obtained from VWR. 4-Methyl-2-pentanone was purchased from Alfa Aesar. Stock solutions of 80 wt % of DMS-S35 in toluene and 50 mmolar solution of TBAF in 4-methyl-2-pentanone (Cat sol) were prepared for coating formulations. Other reagents were used as received.

Coating preparation. An automated coating formulation system manufactured by Symyx Discovery Tools, Inc. was used to prepare the formulations. Materials were dispensed into 24 vials using a robotic pipette having interchangeable tips and mixed with a magnetic stir bar on each vial. The drawdowns were made over aluminum panels and kept under ambient conditions for 24 hours followed by overnight oven curing at 50° C.

Coating characterization. An automated surface energy measurement unit manufactured by Symyx Discovery Tools, Inc and First Ten Angstroms was used to measure coating surface energy. Droplets of water and methyleneiodide (MI) were deposited on the coating separately and a CCD camera imaged the droplets and then automated image analysis was used to determine the contact angles. Three droplets of water and MI were used for each measurement. Surface energy was calculated from the contact angles data using the Owens equation. Dynamic contact angles with water were measured with the same automated surface energy measurement unit. Advancing contact angle ($\theta A$) was measured by dispensing additional liquid over a liquid drop placed on a solid under equilibrium condition. Receding contact angle ($\theta R$) was measured during the withdrawing of the liquid. The difference between $\theta A$ and $\theta R$ was reported as the contact angle hysteresis.

In order to identify siloxane-QAS compositions that have anti-fouling properties over a longer period of time, a number of variables must be explored over a wide range. The high throughput approach is a methodology that can be used to accelerate this process, allowing the screening of large number of variables in shorter time. In these experiments, we were interested in exploring different types of QASs, their levels of addition, and molecular weight of PDMS on the stability against delaminating from the aluminum substrates after one month of water immersion. QAS containing trimethoxy groups were reacted with silanol terminated PDMS and methyltriacetoxysilane in presence TBAF catalyst solution to form a crosslinked network where QAS was chemically bonded with PDMS. Model reaction for the formation of crosslinked PDMS network containing QAS is shown in Scheme 1 (preparation of crosslinked PDMS network containing quaternary ammonium salts).

Scheme 1.

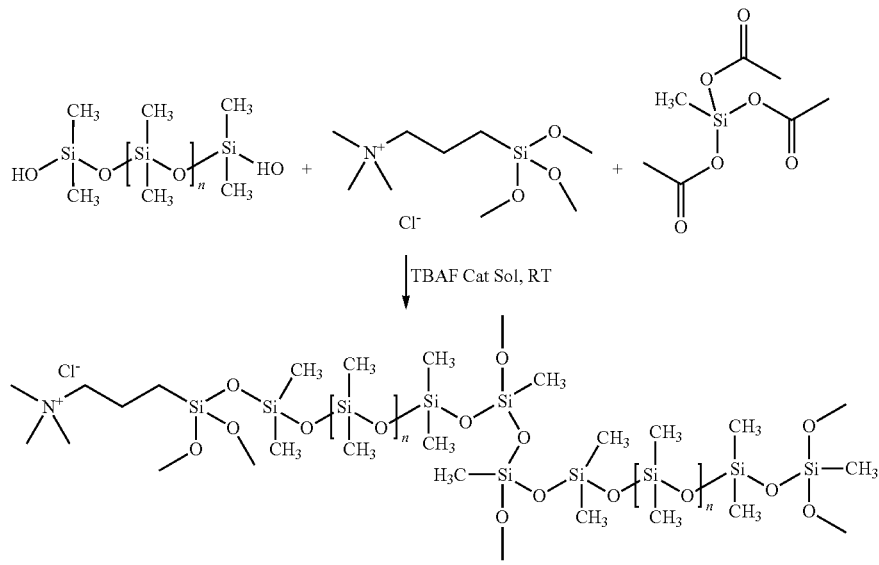

Three libraries were prepared based on silanol terminated PDMS of three different molecular weight (2000, 18000 and 49000). Four different QASs (SA, SB, SC, and SD) were used in each library. The levels of addition of each QAS were varied from 0.005 moles to 0.03 moles per 100 gm of PDMS. In each formulation 15 wt % of methyltriacetoxysilane and 10 wt % of 50 mmolar TBAF solution were added on the basis of total amount of PDMS. The outline of library design is shown in FIG. 1. Overall 72 coating formulations were prepared to study their surface energy, water contact angle hysteresis, and hydrolytic stability.

Figures 2A, 2B:
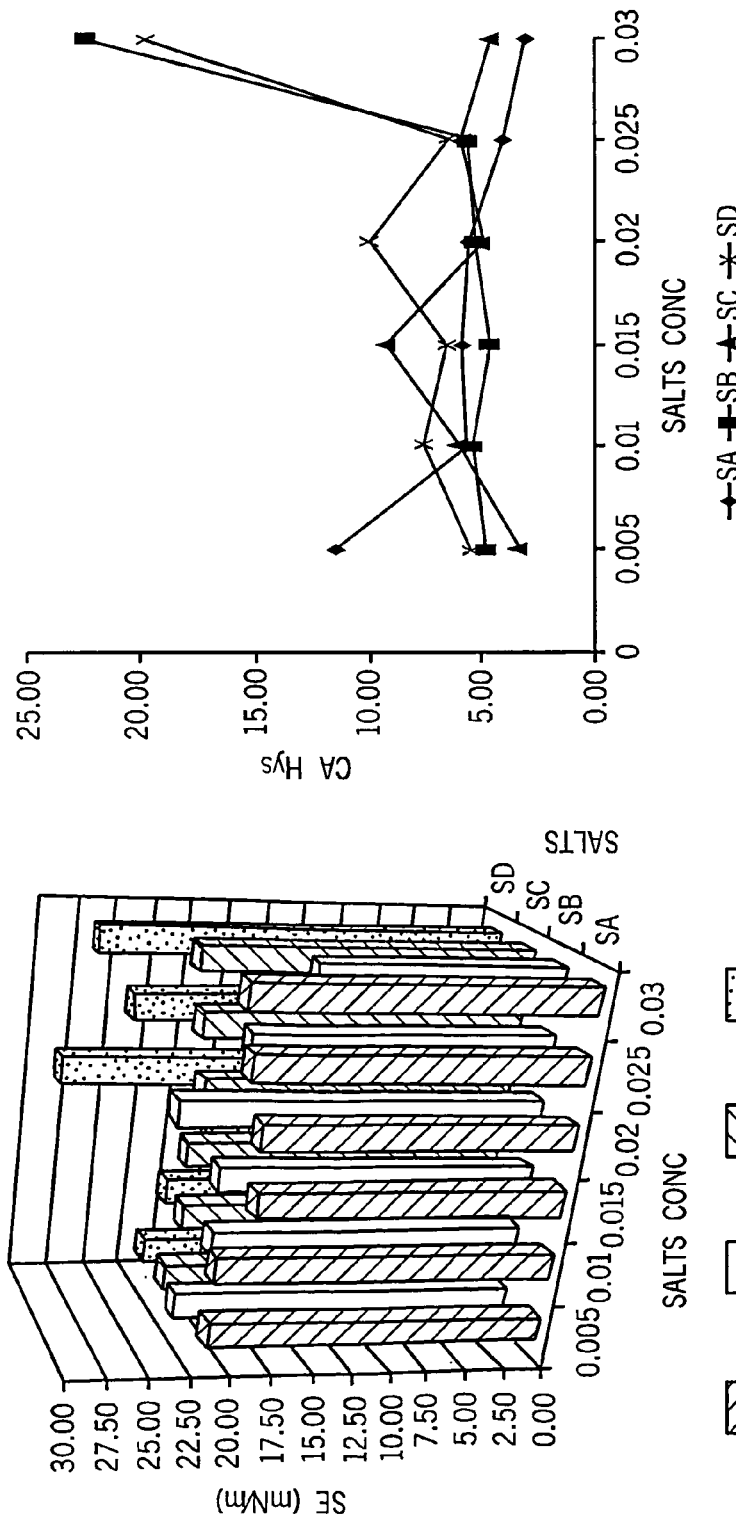
FIG. 2 shows (A) initial surface energy and (B) water contact angle hysteresis of the library based on PDMS MW 2000.
Figures 3A, 3B:
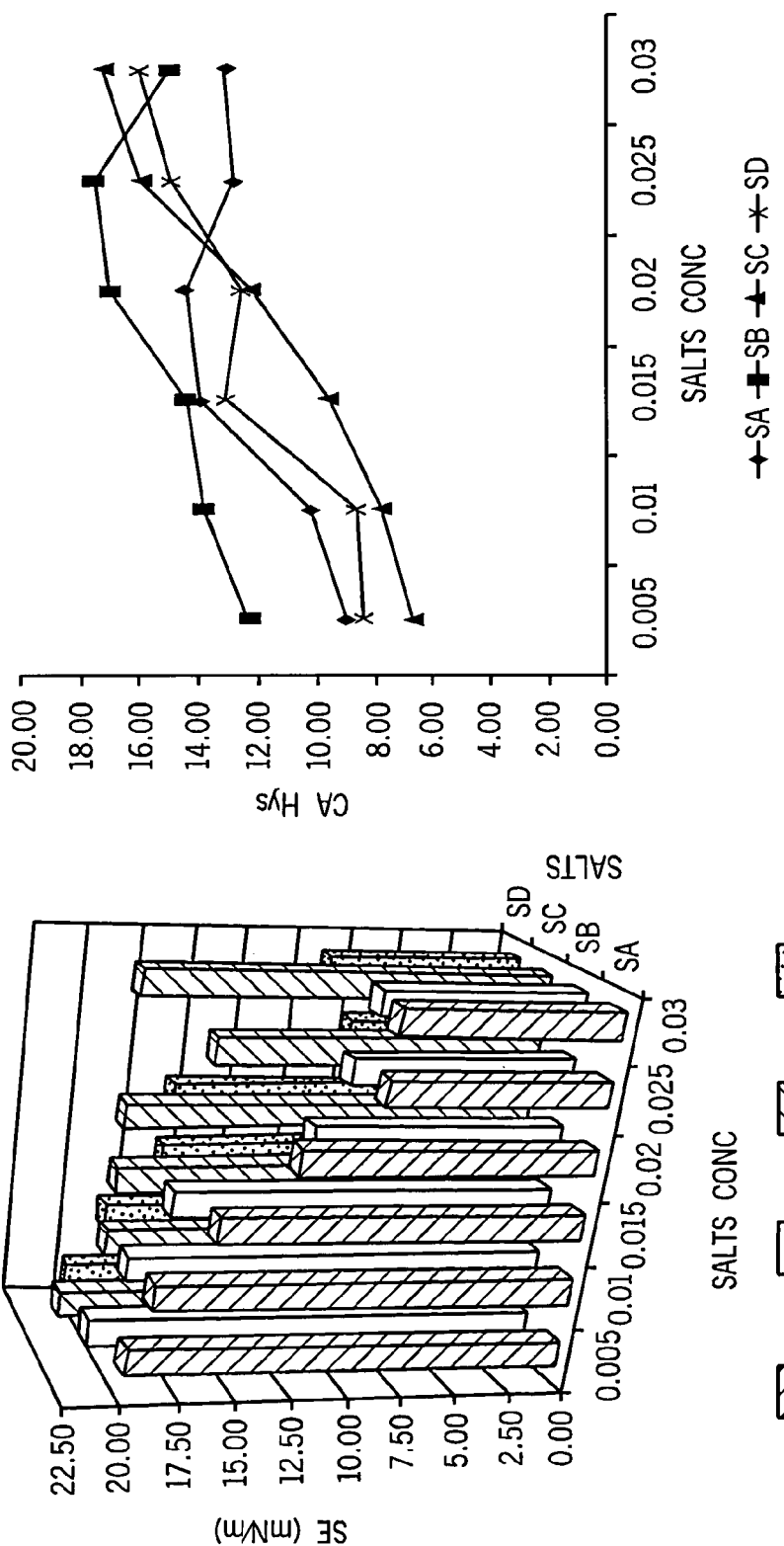
FIG. 3 shows (A) initial surface energy and (B) water contact angle hysteresis of the library based on PDMS MW 18000.
Figure 4B:
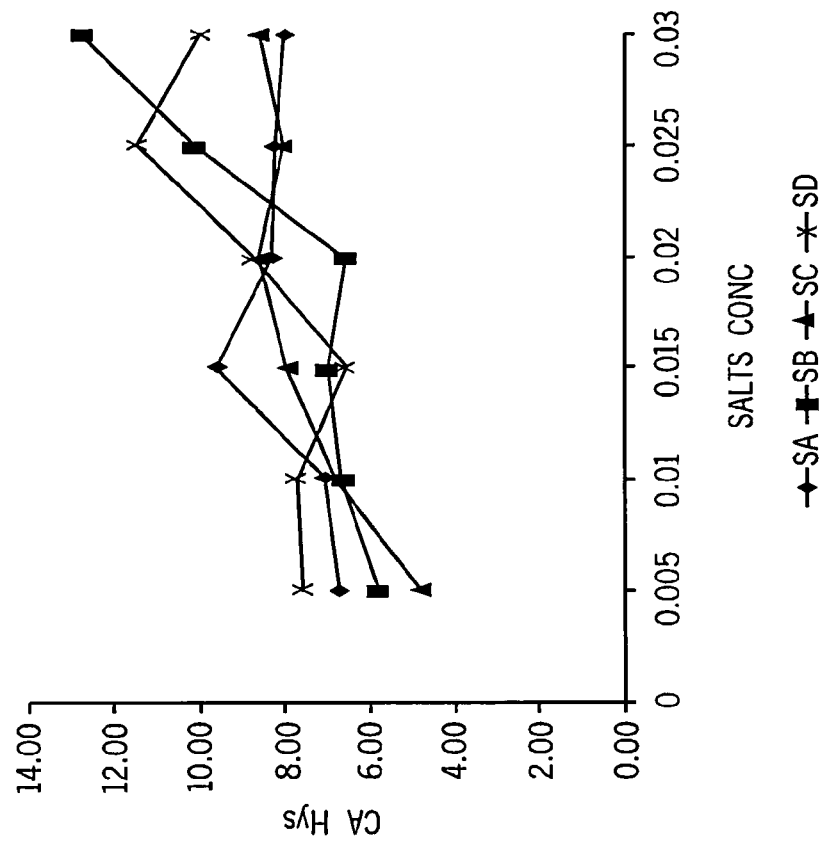
FIG. 4 shows (A) initial surface energy and (B) water contact angle hysteresis of the library based on PDMS MW 49000.
Figure 4A:
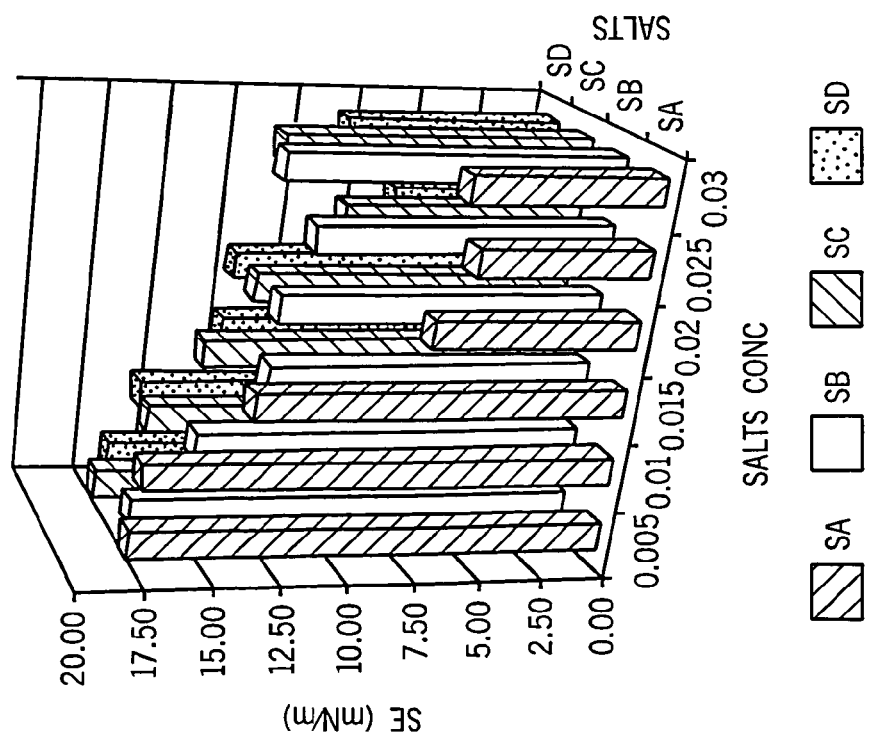

Surface energy and water contact angle hysteresis data of the library prepared with PDMS MW 2000 are shown in FIGS. 2a and 2b respectively. Results of surface energy and water contact angle hysteresis of the libraries with PDMS MW 18000 and 49000 are shown in FIGS. 3 and 4 respectively. Surface energy has been used as a criterion for the evaluation of hydrophobicity and to determine the wettability of the surface. Incorporation of QAS in PDMS did not affect the surface energy of the coatings with low molecular weight PDMS (MW 2000), as shown in FIG. 2a. This might be due to better mixing between low molecular weight PDMS and QASs with trimethoxy groups. With the increase in PDMS molecular weight, the chance of phase separation between PDMS and QASs increases. The amount of QAS in the coating formulation also played an important role in phase separation. The extent of phase separation increased with the increase in the amount of QAS in the formulations. Hence, during the process of film formation, more PDMS would be at the air interface for the formulations containing high molecular weight PDMS and higher amount of QAS, as PDMS had the lowest surface energy. This phenomenon was reflected in the surface energy data in FIG. 3a and 4a from the libraries prepared with PDMS MW 18000 and 49000 respectively. For these two libraries, surface energy of the coatings decreased with the increase in QAS in the formulations as the extent of phase separation between PDMS and QAS increased. As the extent of phase separation increases, the surface roughness might increase, which would also result in a decrease in the surface energy of a hydrophobic surface.

Figure 5:
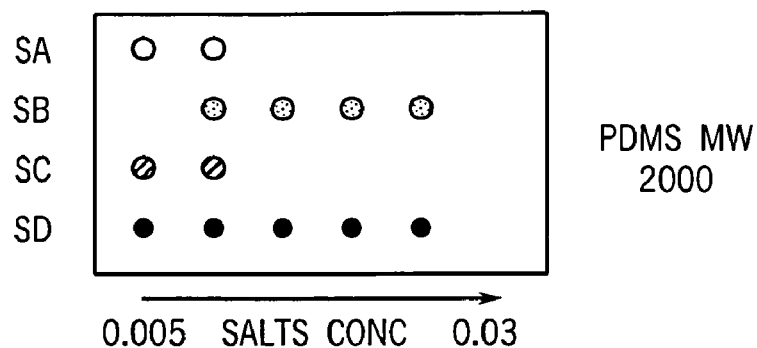
FIG. 5 shows results for selected coating formulations from three libraries after one month of water immersion.
Figure 5:
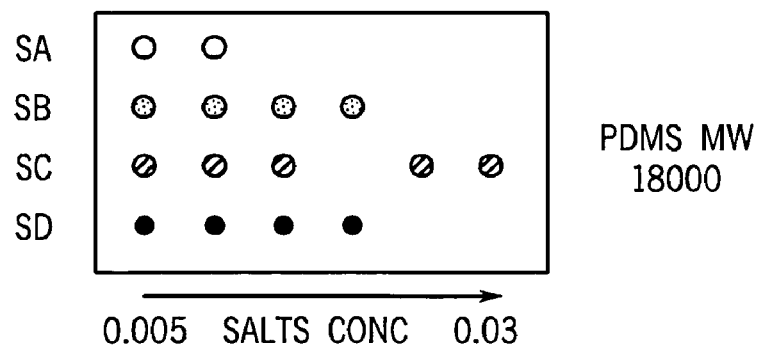
Figure 5:
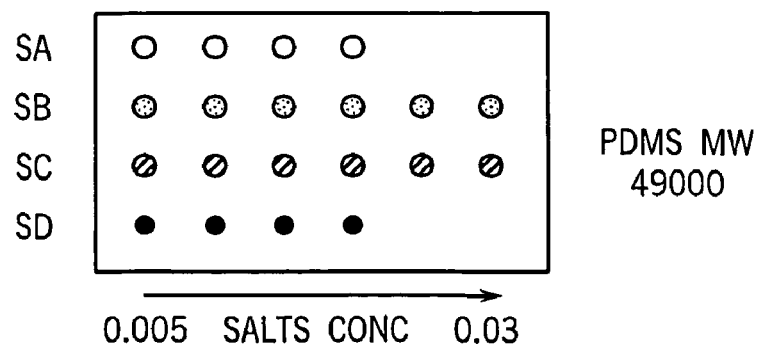

Measurement of contact angle hysteresesis is an important surface characterization technique. Contact angle hysteresis is attributed to heterogeneity present at the surface and surface deformation. Water contact angle hysteresis increased with the increase in the amount of QAS in the formulations in the libraries with PDMS MW 18000 and 49000 as shown in FIGS. 3b and 4b respectively. During the measurement of water contact angle hysteresis the surface was in contact with the water for longer period of time which might allow an increase in surface heterogeneity as more QAS would preferentially orient to the water interface. However, this trend was not observed in the library with PDMS MW 2000 (FIG. 2b). These 72 coatings (from three libraries) were immersed in artificial sea water for one month. After one month of water immersion initial screening were performed in order to determine their stability against delaminating from the aluminum plates. Coatings that delaminated from the aluminum plates were rejected. Coatings from all three libraries that passed this screening are shown in FIG. 5 (which shows results for selected coating formulations from three libraries after one month of water immersion) according to their positions. Blank spaces in the libraries represent delaminated coatings. The number of coatings per library that passed this screening test increases with the increase in the molecular weight of PDMS. The library with PDMS MW 49000 had the highest number of stable coatings (20 of 24), and the library with PDMS MW 2000 had the lowest number of coatings that passed the screening test (13 of 24). Formulations with SA as QAS had the lowest stability irrespective of the molecular weight of PDMS (only 8 formulations out of 18 formulations from the three libraries were stable).

A high-throughput combinatorial approach has successfully applied to formulate and to characterize coatings based on silanol terminated PDMS and QASs. Initial surface energy data revealed that the surface energy of the coatings decreased with the increase in the amount of QAS in the formulation with high molecular weight PDMS. This might be due to an increase in the surface roughness with the increase in phase separation for a hydrophobic surface. Initial contact angle hysteresis results showed that the surface became more heterogeneous as the amount of QAS in the formulation increased when high molecular weight PDMS were used in the formulations. One month water immersion test of these coatings revealed that the coatings with highest molecular weight PDMS (49000) had the highest stability against delaminating from the aluminum substrates.

Antimicrobial Coatings for Infection Control of Endotracheal Tubes

Endotracheal tubes (ETTs) are commonly employed in the health care industry for airway management and mechanical ventilation of patients receiving medical treatment. Serious complications can arise as a result of an ETT intubation including respiratory obstructions (i.e., tracheal impaction) and ventilator-associated pneumonia (VAP). VAP is the leading cause of morbidity and mortality in intensive care units. It has been reported that the average cost per case of VAP is $3,000 to $6,000, requires an additional two weeks of hospitalization for the patient, and accounts for ~60% of all deaths due to nosocomial (i.e., hospital acquired) infections.

The onset of VAP is typically attributed to the aspiration of oropharyngeal secretions that harbor pathogenic microorganisms. In this regard, intubation with an ETT can interfere with the patients normal bodily defenses against aspiration, and facilitate direct access of pathogenic microorganisms into the lungs. VAP that occurs within 48 hours after intubation is categorized as "early-onset" VAP, and those that occur after 72 hours are referred to as "late-onset" VAP. Early-onset VAP is typically caused by antimicrobial sensitive microorganisms, while late-onset VAP is usually associated with antimicrobial resistant, nosocomial organisms (i.e., *P. aeruginosa*, MRSA, *Acinetobacter*, etc.).

A variety of measures can be taken to prevent the prevalence VAP, including: semi-recumbent positioning of the head, continuous oscillation of the body, and continuous aspiration of subglottic secretions. Another approach is to prevent the microbial colonization of ETTs by impregnating the PVC with antimicrobial agents or coating the ETT with an antimicrobial coating. A silver coated antimicrobial ETT has recently been introduced by Bard (i.e., Agento I. C.). Although effective, silver based technologies may contribute to failure of the medical device and foster the development of antimicrobial resistance.

The development of elastomeric coatings containing one or more chemically tethered antimicrobial agents designed to function by direct contact, rather than release and ingestion by the target organism, is currently being investigated. Coatings containing bound quaternary ammonium salts (QAS's) have been shown to possess broad spectrum antimicrobial activity and theorized to be impervious to the development of antimicrobial resistance. Since no leaching of the antimicrobial agent occurs, a contact active antimicrobial coating may maintain therapeutic activity over a longer period of time than a coating system that functions by a release mechanism(s). Furthermore, a coating with long-term antimicrobial activity may significantly reduce the incidence of late-onset VAP.

Figure 6:
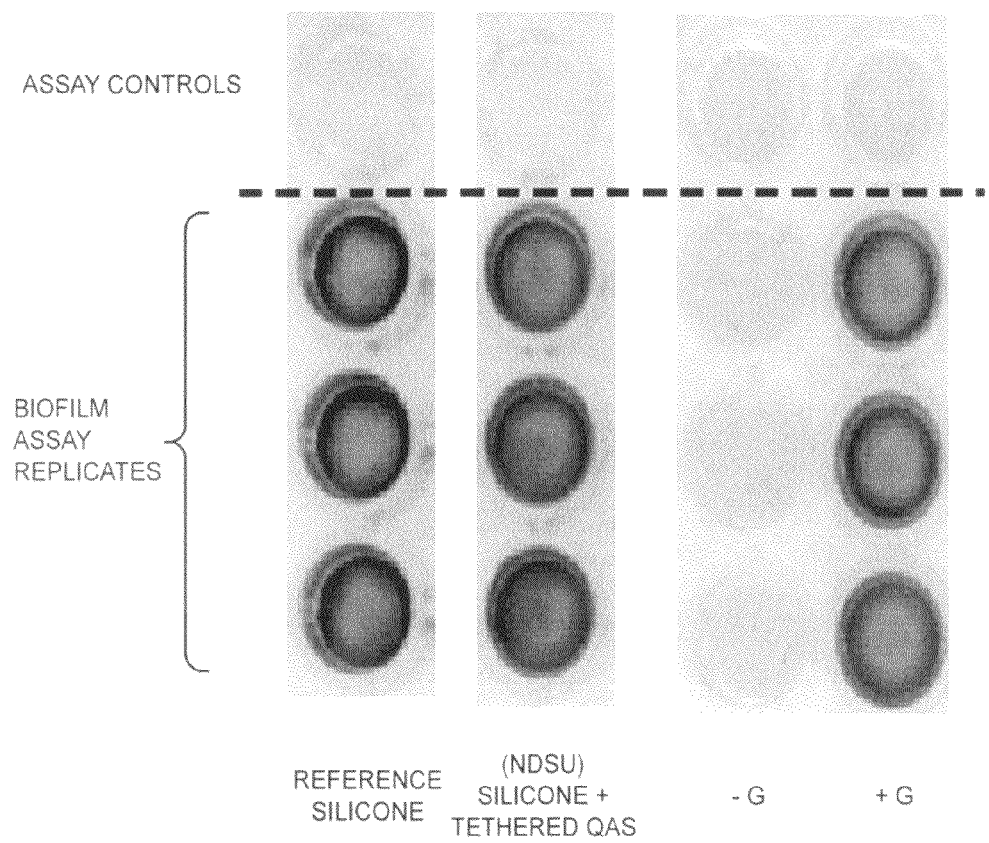
FIG. 6 shows leachate toxicity analysis with *E. coli* of Teleflex urinary catheters coated with an antimicrobial coating.

Preliminary work has been carried out to apply novel, contact active antimicrobial coatings to urinary catheters supplied by Teleflex Medical Inc. As with ETTs, urinary catheters are susceptible to microbial colonization and can serve as a reservoir for infection. Specifically, a siloxane containing a bound QAS was applied to Teleflex urinary catheters using a dip coating process. After curing, the coated catheters were sectioned into 5 mm segments and evaluated for leaching of toxic components after immersion in phosphate buffered saline (PBS) for 24 hours. FIG. 6 shows leachate toxicity analysis with *E. coli* of Teleflex urinary catheters coated with an NDSU antimicrobial coatings (−G=no growth in leachate; +G=growth in leachate). As shown in FIG. 6, no detectable leachate toxicity was observed for the antimicrobial coated catheter when evaluated with the Gram negative bacterium, *E. coli*.

Figure 7:
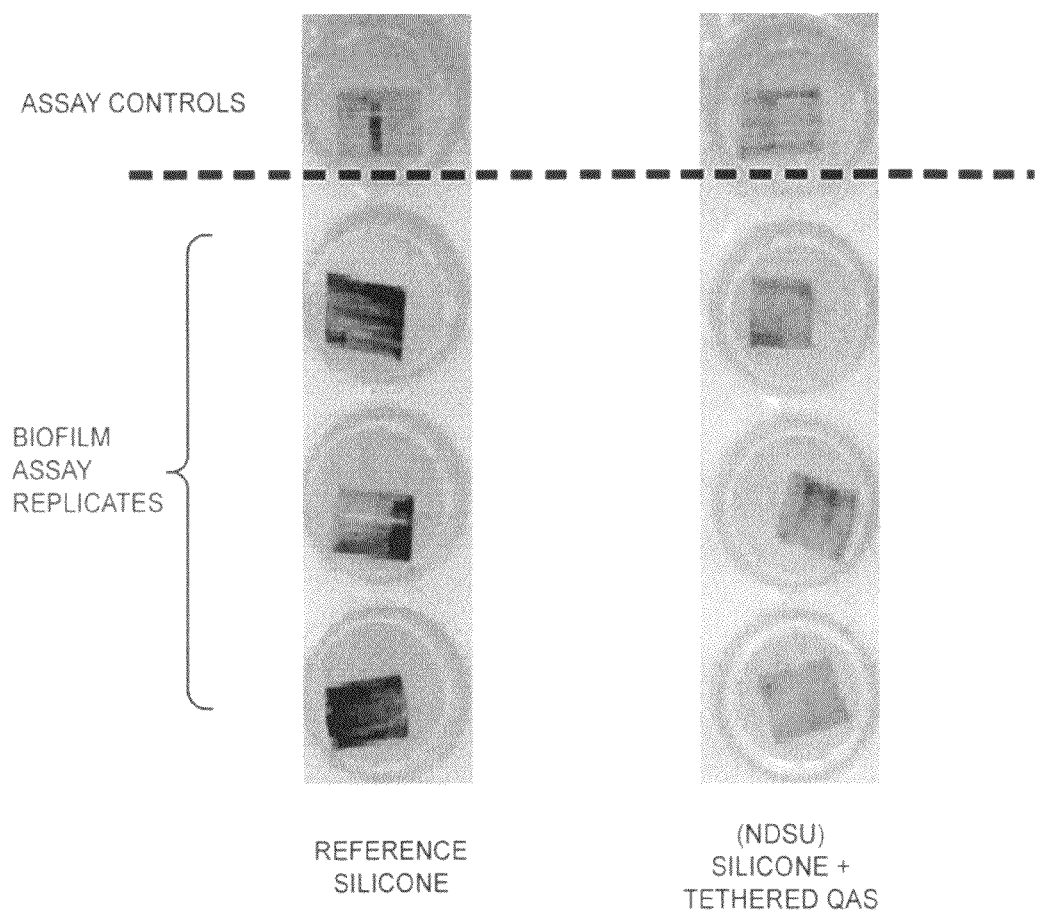
FIG. 7 shows catheter segments after organism exposure and crystal violet staining; an uncoated catheter is shown on the left and a coated catheter is shown on the right.

The antimicrobial coated catheter sections were also evaluated for their resistance to microbial colonization using an array of microorganisms deemed relevant to catheter associated urinary tract infections (CUTI). Coated catheter sections were immersed in microorganism suspensions ($\sim 10^7$ to $10^8$ cells.ml$^{-1}$) for 24 hours to facilitate attachment and biofilm growth. After microorganism exposure, the coated catheters were rinsed and stained with a biomass indicator dye, crystal violet (see FIG. 7; Catheter segments after organism exposure and crystal violet staining. Uncoated catheter is shown on the left. NDSU coated catheter is shown on the right).

Figure 8:
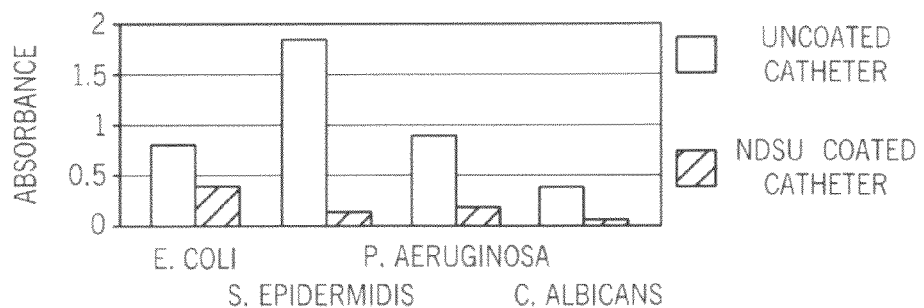
FIG. 8 shows extraction and absorbance measurements of the crystal violet dye (600 nm) for the uncoated and coated catheter segments for the array of microorganisms used for evaluations.

The uncoated catheter segments exhibited dark crystal violet staining due to microbial colonization while the coated catheters segments showed no increase in crystal violet dye uptake relative to the assay control indicating no significant microbial colonization. Extraction and absorbance measurements of the crystal violet dye (600 nm) for the array of microorganisms used for evaluations are shown in FIG. 8 (Crystal violet absorbance measurements for the uncoated and coated catheter segments). It is clear that the coated catheters show a significant reduction in microbial colonization when compared to the uncoated control catheter. Thus, the coated catheters exhibit broad spectrum activity towards both Gram positive (*S. epidermidis*) and Gram negative (*E. coli* and *P. aeruginosa*) bacteria, as well as good activity against a yeast pathogen (*C. albicans*).

Figure 9:
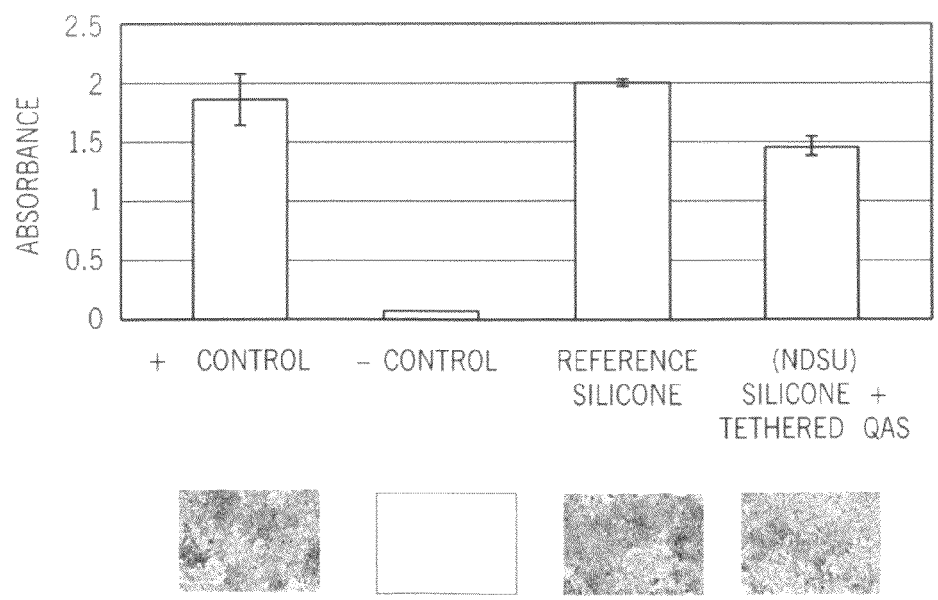
FIG. 9 shows L929 mouse fibroblast biocompatibility evaluation of uncoated and NDSU coated catheter segments; pictures below each bar show a representative image of mouse fibroblast cells after 24 hour incubation in catheter extracts.

The coated catheter segments were also evaluated with respect to biocompatibility. The coated catheter segments were immersed in a cell culture growth medium for 24 hours, and the resulting extracts were transferred to adherent L929 mouse fibroblast cells. After 24 hours of incubation, the viability of the L929 cells were assayed using an MTT viability assay (FIG. 9; L929 mouse fibroblast biocompatibility evaluation of uncoated and NDSU coated catheter segments). Pictures below each bar show representative image of mouse fibroblast cells after 24 hour incubation in catheter extracts (control demonstrates no viable L929 cells due to treatment with 1% triton-X100). There was no significant reduction in L929 viability for the uncoated or coated catheter segments.

Figure 10:
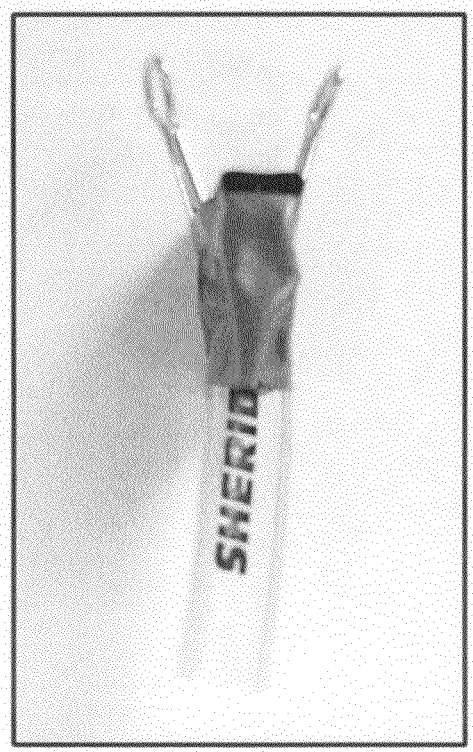
FIG. 10 shows a photograph of a coated segment of an endotracheal tube.

With regard to the physical properties of the coatings, a preliminary, subjective evaluation of coated segments of urinary catheters and ETTs was conducted. For both segments of urinary catheters and ETTs, it was found that dip coating with one of the present coatings resulted in coated specimens that were highly optically transparent, resistant to cracking upon flexing, and resistant to delamination. FIG. 10 shows a photograph of a coated segment of an ETT which illustrates that high optical transparency of the coating.

Figure 11:
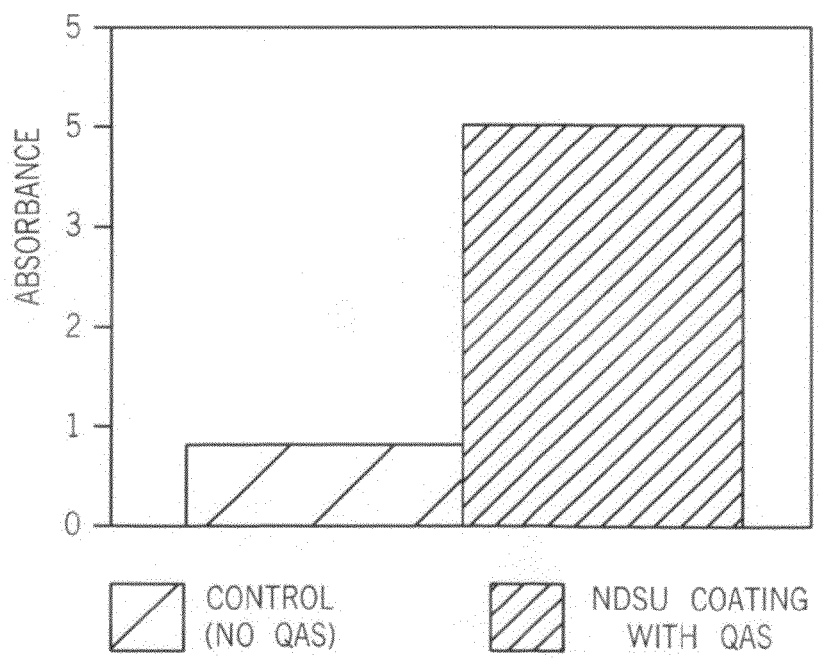
FIG. 11 shows turbidity measurements of siloxane-based coating solutions containing 1 weight percent silver nanoparticles 24 hours after vortex mixing.

Since fluid build-up in the vicinity of the inflated cuff of an ETT may contain pathogenic microorganisms and these microorganisms may not come into contact with the coating, a leachable antimicrobial agent may be desired to use in conjunction with a surface-bound contact active antimicrobial agent. Silver is a widely used antimicrobial agent that is active through a leaching mechanism. Previous work has shown that the addition of silver nanoparticles to silicone coating solutions result in poor dispersion of the silver nanoparticles. This result is most likely due to the nonpolar nature of silicones. It was thought that the highly polar, ionic QAS groups present in the siloxane coatings being investigated may enable a much better dispersion of silver nanoparticles. This hypothesis was tested by making a standard siloxane coating solution containing 1.0 weight percent silver nanoparticles and a comparable coating solution that contained the QAS functionality. Turbidity measurements were made 24 hours after vortex mixing the two coatings solutions. FIG. 11 shows turbidity measurements of siloxane-based coating solutions containing 1 weight percent silver nanoparticles 24 hours after vortex mixing. As shown in FIG. 11, the coating based the QAS functional siloxane was much more turbid (higher absorbance value) than the control coating. The higher turbidity of the QAS-functional siloxane shows that the QAS functionality enables a much better dispersion of the silver nanoparticles and suggests that novel, antimicrobial coatings possessing both long-term contact active antimicrobial activity as well as longer range, releasable antimicrobial activity can be produced using the approach described herein.

Table 1 lists materials used to prepare additional coatings (PDMS=polydimethylsiloxane).

TABLE 1

| Supplier ID | Description | Supplier |
| --- | --- | --- |
| DMS-S27 | 18,000 g./mole silanol terminated PDMS | Gelest |
| DMS-S35 | 49,000 g./mole silanol terminated PDMS | Gelest |
| SIT 7090 | tetradecyldimethyl(3-trimethoxysilylpropyl) ammoniumchloride, 50% in methanol | Gelest |
| SIO 6620 | octadecyldimethyl(3-trimethoxysilylpropyl) ammoniumchloride, 60% in methanol | Gelest |
| SIM 6519 | methyltriacetoxysilane | Gelest |
| 1.0 M TBAF | 1.0 molar tetrabutylammoniumfluoride in tetrahydrofuran | Aldrich |
| Toluene | toluene | VWR |
| 4-Methyl-2-pentanone | 4-Methyl-2-pentanone | Alfa Aesar |
| DC 3140 | Commercially-available silicone coating | Dow-corning |

Formulations Based on C-18 QAS 3.5 gm of DMS-S27, 0.58 gm of SIO 6620, 0.53 gm of SIM 6519, and 0.53 gm of a 50 mmolar tetrabutylammonium fluoride catalyst solution (prepared by diluting 1.0 M TBAF in 4-methyl-2-pentanone) were combined in an 8 ml glass vial using continuous magnetic stirring. The solution was allowed to mix overnight using magnetic stirring. 250 microliter aliquots of coating solution were deposited into wells of a 24 well array plate (6 columns and 4 rows) that were modified with epoxy primed aluminum discs. The deposition was done such that the coating composition occupied an entire column of the 24 well array plate (4 replicate coatings per array plate). In addition to the experimental coating, each array plate contained a silicone reference coating derived from a 35% by weight solution of DC 3140 in 4-methyl-2-pentanone. Coatings were allowed to cure for 24 hours at room temperature, followed by an additional 24 hours at 50° C. Prior to conducting biofilm retention assays, the coatings were preconditioned by immersing the arrays in water for 15 days to remove any leachable toxic components. In addition, leachate toxicity assays were conducted to ensure that coating leachates were not toxic. Percent reductions in biofilm retention of this coating with respect to DC 3140 against different microorganisms are shown Table 2.

TABLE 2

| E. Coli | S. epidermidis |
| --- | --- |
| 90 ± 1 | 57 ± 13 |

4.4 gm of an 80 wt % solution of DMS-S35 in toluene, 0.58 gm of SIO 6620, 0.53 gm of SIM 6519, and 0.53 gm of a 50 mmolar tetrabutylammonium fluoride catalyst solution (prepared by diluting 1.0 M TBAF in 4-methyl-2-pentanone) were combined in an 8 ml glass vial using continuous magnetic stirring. The solution was allowed to mix overnight using magnetic stirring. Coatings were prepared in 24 well array plates, cured, preconditioned, and tested for leachate toxicity as discussed in the previous example. Percent reductions in biofilm retention (% reduction±std) of this coating with respect to DC 3140 against different microorganisms are shown in Table 3.

TABLE 3

| E. Coli | S. epidermidis |
| --- | --- |
| 79 ± 1 | 82 ± 4 |

Formulations Based on C-18 and C-14 QAS 3.5 gm of DMS-S27, 0.43 gm of SIO 6620, 0.15 gm of SIT 7090, 0.53 gm of SIM 6519, and 0.53 gm of a 50 mmolar tetrabutylammonium fluoride catalyst solution (prepared by diluting 1.0 M TBAF in 4-methyl-2-pentanone) were combined in an 8 ml glass vial using continuous magnetic stirring. The solution was allowed to mix overnight using magnetic stirring. Coatings were prepared in 24 well array plates, cured, preconditioned, and tested for leachate toxicity as discussed in the previous example. Percent reductions in biofilm retention of this coating with respect to DC 3140 against different microorganisms are shown Table 4.

TABLE 4

| E. Coli | P. aeruginosa |
| --- | --- |
| 73 ± 11 | 72 ± 21 |

4.4 gm of 80 wt % solution of DMS-S35 in toluene, 0.43 gm of SIO 6620, 0.15 gm of SIT 7090, 0.53 gm of SIM 6519, and 0.53 gm of a 50 mmolar tetrabutylammonium fluoride catalyst solution (prepared by diluting 1.0 M TBAF in 4-methyl-2-pentanone) were combined in an 8 ml glass vial using continuous magnetic stirring. The solution was allowed to mix overnight using magnetic stirring. Coatings were prepared in 24 well array plates, cured, preconditioned, and tested for leachate toxicity as discussed in the previous example. Percent reductions in biofilm retention (% reduction±std) of this coating with respect to DC 3140 against different microorganisms are shown Table 5.

TABLE 5

| E. Coli | P. aeruginosa |
| --- | --- |
| 87 ± 2 | 96 ± 1 |

This coating formulation was also used to coat sections of urinary catheters obtained from Teleflex Corporation. Percent reductions in biofilm retention (% reduction±std) of the coated catheter sections were compared to uncoated catheter sections using different microorganisms are shown Table 6.

ammonium salt (QAS) moieties for application as antifouling coatings to inhibit marine biofouling and antimicrobial coatings for biomedical devices. The synthetic process used to produce the coatings containing chemically-bound QAS moieties is shown in Scheme 2 below.

Scheme 2

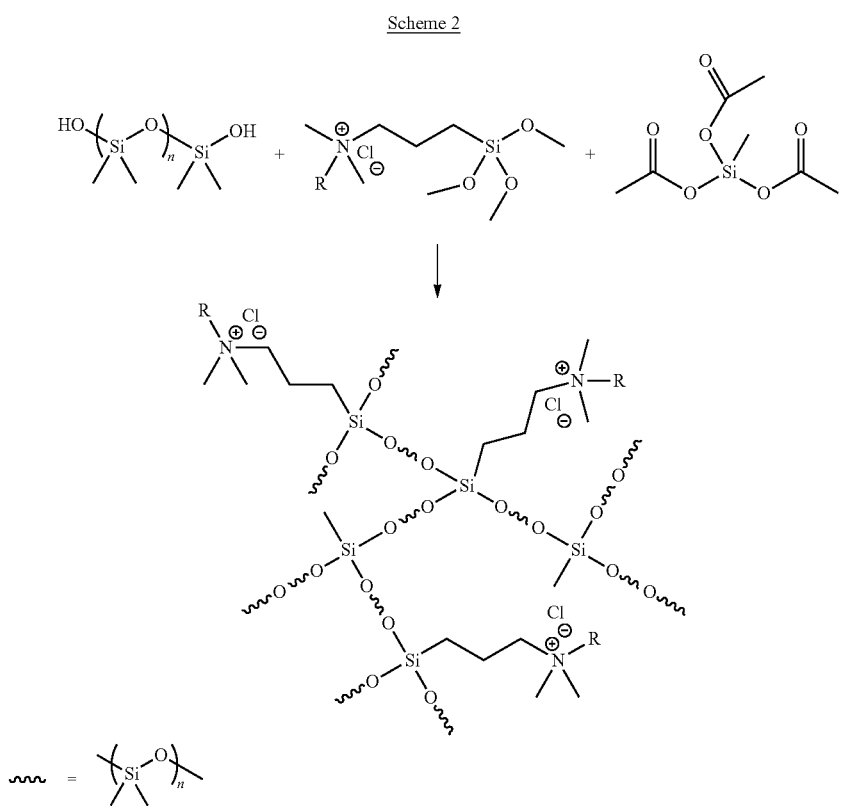

TABLE 6

| E. Coli | S. epidermidis | P. aeruginosa | C. albicans |
|---------|----------------|---------------|-------------|
| 54      | 94             | 80            | 89          |

Antimicrobial Coatings for Biomedical Devices

In today's society, advanced medical treatment sees an increasing amount of procedures in which foreign materials are placed inside or in contact with the human body. For example, from 1996 to 2001 the number of hip and knee replacement surgeries have increased by 14 percent. Other devices, such as venous and urethral catheters, are used daily. Whether temporary or permanent, implantation of these foreign objects into the body can facilitate transmission of microbial pathogens and cause infection in patients receiving medical treatment. Considering the importance of implant-associated infections, there exists a need for new biocompatible, antimicrobial coatings for biomedical devices.

Due to their biocompatibility, low degree of thrombogenicity, and desirable physical properties, polysiloxanes have been extensively used for biomedical applications such as urinary catheters, protective sheaths for pacemakers, and coatings for implantable electronics. Combinatorial capabilities have been used to investigate moisture-curable, polysiloxane-based coatings containing chemical bound quaternary The variables investigated included QAS composition, i.e. alkyl chain length, QAS concentration, and silanol-terminated polydimethylsiloxane molecular weight. In total, 75 unique coating compositions were prepared and characterized with respect surface and antimicrobial properties towards a suite of microorganisms including a marine bacterium, *Cellulophaga lytica*, a species of algae, *Navicula incerta*, the biomedically-relevant Gram-positive bacterium, *Staphylococcus epidermidis*, the biomedically-relevant Gram-negative bacteria, *Escherichia coli* and *Pseudomonas aeruginosa*, and the yeast pathogen, *Candida albicans*.

All three variables influenced coating surface properties as well as antimicrobial characteristics. Characterization of coating surface morphology revealed a heterogeneous, two-phase morphology for many of the coatings. A correlation was found between water contact angle and coating surface roughness with the contact angle increasing with increasing surface roughness. Coatings based on the QAS moiety containing the longest alkyl chain (18 carbons) displayed the highest micro-roughness and, thus, the most hydrophobic surfaces. With regard to antimicrobial properties, coatings based on the 18 carbon QAS moieties were very effective at inhibiting biofilm formation of all of the bacterial species investigated, as well as the yeast pathogen. Coatings based on the 14 carbon QAS were very effective at inhibiting biofilm growth of *N. incerta*.

Antimicrobial Activity of Quaternary Ammonium Compounds Containing Trimethoxysilane Groups Quaternary ammonium compounds (QACs) containing trimethoxysilane (TMS) were synthesized by alkylating 3-(N,N-dimethylaminopropyl) trimethoxysilane and bis(3-trimethoxysilylpropyl)-n-methylamine using alkyl halides ranging in length from $C_4$ to $C_{15}$. A rapid screening assay was utilized to evaluate their antimicrobial activity against the Gram-positive bacterium, *S. aureus*, and the Gram-negative bacterium, *E. coli*.

Synthesis

A schematic of the synthesis of TMS-functional QACs is shown in Scheme 3 below.

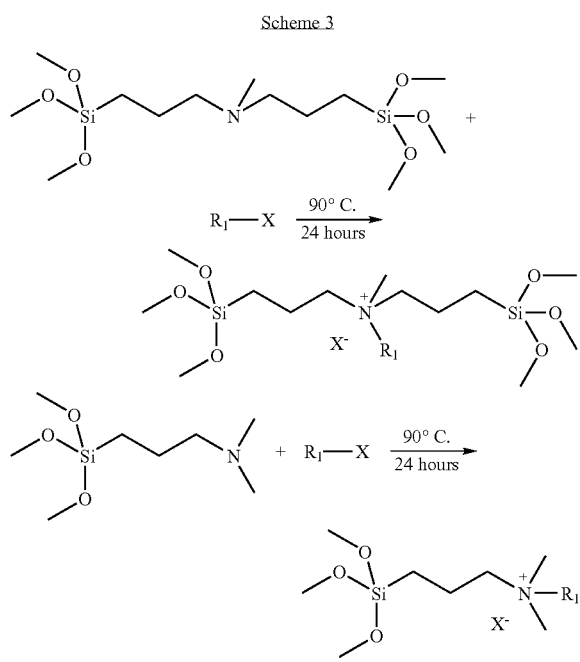

Scheme 3

QACs were synthesized by mixing an alkyl halide with M-amine or D-amine at a 1:1 molar ratio in 8 mL vials and heating the reaction mixture at 90° C. for 24 hours using magnetic stirring. After cooling the reaction to room temperature, methanol was added to each vial to produce a 50 percent (wt./wt.) solution of the QAC in methanol. A list of material used for the synthesis of the QACs is provided in Table 7.

TABLE 7

| Material | Supplier |
| --- | --- |
| Bis(3-trimethoxysilylpropyl)-n-methylamine (D-amine) | Gelest |
| 3-(N,N-Dimethylaminopropyl) trimethoxysilane (M-amine) | Gelest |
| 1-Bromobutane | Aldrich |
| 1-Bromopentane | Aldrich |
| 1-Iodohexane | Aldrich |
| 1-Iodoheptane | Aldrich |
| 1-Iodooctane | Aldrich |
| 1-Iodononane | Aldrich |
| 1-Iododecane | Aldrich |
| 1-Iodoundecane | Aldrich |
| 1-Iodododecane | Aldrich |
| 1-Bromotridecane | Aldrich |
| 1-Bromotetradecane | Aldrich |
| 1-Bromopentadecane | Aldrich |

The compositional details for each QAC synthesis are provided in Table 8 (all values are in grams).

TABLE 8

| Sample | D-amine | M-amine | Alkyl halide | Wt. Alkyl halide | Methanol |
| --- | --- | --- | --- | --- | --- |
| DC4Br | 2.67 | 0.0 | 1-bromobutane | 1.03 | 3.70 |
| DC5Br | 2.67 | 0.0 | 1-bromopentane | 1.13 | 3.80 |
| DC6I | 2.67 | 0.0 | 1-iodohexane | 1.59 | 4.26 |
| DC7I | 2.67 | 0.0 | 1-iodoheptane | 1.70 | 4.37 |
| DC8I | 2.67 | 0.0 | 1-iodooctane | 1.80 | 4.47 |
| DC9I | 2.67 | 0.0 | 1-iodononane | 1.91 | 4.58 |
| DC10I | 2.67 | 0.0 | 1-iododecane | 2.01 | 4.68 |
| DC11I | 2.67 | 0.0 | 1-iodoundecane | 2.12 | 4.79 |
| DC12I | 2.67 | 0.0 | 1-iodododecane | 2.22 | 4.89 |
| DC13Br | 2.67 | 0.0 | 1-bromotridecane | 1.97 | 4.64 |
| DC14Br | 2.67 | 0.0 | 1-bromotetradecane | 2.08 | 4.75 |
| DC15Br | 2.67 | 0.0 | 1-bromopentadecane | 2.19 | 4.86 |
| MC4Br | 0.0 | 1.56 | 1-bromobutane | 1.03 | 2.59 |
| MC5Br | 0.0 | 1.56 | 1-bromopentane | 1.13 | 2.69 |
| MC6I | 0.0 | 1.56 | 1-iodohexane | 1.59 | 3.15 |
| MC7I | 0.0 | 1.56 | 1-iodoheptane | 1.70 | 3.26 |
| MC8I | 0.0 | 1.56 | 1-iodooctane | 1.80 | 3.36 |
| MC9I | 0.0 | 1.56 | 1-iodononane | 1.91 | 3.47 |
| MC10I | 0.0 | 1.56 | 1-iododecane | 2.01 | 3.57 |
| MC11I | 0.0 | 1.56 | 1-iodoundecane | 2.12 | 3.68 |
| MC12I | 0.0 | 1.56 | 1-iodododecane | 2.22 | 3.78 |
| MC13Br | 0.0 | 1.56 | 1-bromotridecane | 1.97 | 3.53 |
| MC14Br | 0.0 | 1.56 | 1-bromotetradecane | 2.08 | 3.64 |
| MC15Br | 0.0 | 1.56 | 1-bromopentadecane | 2.19 | 3.75 |

For *S. aureus*, the diTMS-functional QACs showed greater activity than the monoTMS-functional analogs for QACs possessing an alkyl chain length below 10 carbons. However, both the mono- and diTMS-functional QACs possessing an alkyl chain length of 10 carbons and higher gave log reduction values of 7. In contrast, for *E. coli*, the monoTMS-functional QACs were more active than the diTMS-functional QACs. In addition, an optimum in activity toward *E. coli* with the diTMS-functional QACs was found at an alkyl chain length of 11 carbons.

Both the number of TMS groups (one or two) and alkyl chain length of the QACs had an effect on antimicrobial activity. For *S. aureus*, diTMS-functional QACs were more effective than monoTMS-functional QACs, while the opposite behavior was observed for the Gram-negative bacterium, *E. Coli*. Overall, monoTMS-functional QACs possessing a C10 to C12 alkyl chain length gave maximum antimicrobial activity (log 7 reduction) toward both *S. aureus* and *E. coli*.

Anti-Fouling/Fouling-Release Coatings Containing Quaternary Ammonium Salt Groups Polysiloxane coatings containing chemically-bound ("tethered") quaternary ammonium salt (QAS) moieties were investigated for potential application as environmentally-friendly coatings to control marine biofouling. A combinatorial/high-throughput approach was applied to the investigation to enable multiple variables to be probed simultaneously and efficiently. The variables investigated for the moisture-curable coatings included QAS composition, i.e. alkyl chain length, and concentration as well as silanol-terminated polysiloxane molecular weight. A total of 75 compositionally unique coatings were prepared and characterized using surface characterization techniques and biological assays. Biological assays were based on two different marine microorganisms, a bacterium, *Cellulophaga lytica* and a diatom, *Navicula incerta*, as well as a macrofouling alga, *Ulva*. The results of the study showed that all three variables influenced coating surface properties as well as antifouling and fouling-release characteristics.

Characterization of coating surface morphology revealed a heterogeneous, two-phase morphology for many of the coatings investigated. A correlation was found between water contact angle and coating surface roughness with the contact angle increasing with increasing surface roughness. Coatings based on the QAS moiety containing the longest alkyl chain (18 carbons) displayed the highest micro-roughness. With regard to antifouling and fouling-release properties, coatings—based on the 18 carbon QAS moieties were very effective at inhibiting *C. lytica* biofilm formation and enabling easy removal of *Ulva* sporelings (young plants), while coatings based on the 14 carbon QAS moieties were very effective at inhibiting biofilm growth of *N. incerta*.

Marine biological fouling is defined as the undesirable accumulation of microorganisms, plants, and animals on artificial surfaces immersed in seawater, and has been a serious problem for mariners for more than 2,000 years. The fouling of ship hulls increases hydrodynamic drag which can significantly increase fuel consumption. For example, heavy calcareous fouling results in powering penalties up to 86 percent at cruising speed. In addition to an increase in fuel consumption, biofouling increases the frequency of dry-docking, initiates corrosion, and may result in the introduction of invasive species to a marine environment.

There are more than 4,000 species of marine organisms responsible for biofouling, and it has been found that the process of biofouling typically occurs in stages. In the first stage, organic molecules, such as proteins and polysaccharides, rapidly accumulate over the surface to form a "conditioning film" which can promote the growth of a microbial biofilm derived from the attachment of single cell organisms such as bacteria and diatoms. The presence of a microbial biofilm, in turn, can provide cues that facilitate or inhibit the settlement of more complex organisms which attach and grow into relatively large adults, referred to as macrofoulers. Barnacles and tubeworms are examples of common hard calcareous macrofoulers, while the green seaweed, *Ulva* (*Enteromorpha*), is the most common algal macrofouler. Due to the vast array of organisms involved in marine biofouling and the complexity of the fouling process, development of an effective surface coating to combat biofouling has been, and still remains, a major technical challenge.

Historically, the most effective approach to inhibit biofouling has been to utilize toxic compounds, such as organotin compounds, in a surface coating designed to allow for a gradual release of the toxic compounds into the aquatic environment. While this approach has been very effective at controlling marine fouling, it has created significant environmental concern. In fact, the International Maritime Organization banned all new uses of organotin-containing, antifouling coatings after Jan. 1, 2003.

As a result of the environmental concerns associated with the use of antifouling coatings based on leachable biocides, a significant amount of effort has gone into the development of nontoxic coatings which do nothing to inhibit settlement, but, instead, allow for easy-removal of attached biofoulers. Marine coatings based on the "easy-release" approach have been referred to as fouling-release coatings. At present, the commercially-available fouling-release coatings are polysiloxane-based materials. Due to the low surface energy, low modulus, and low surface roughness of polysiloxane coatings, they have been found to be the most effective for providing fouling-release characteristics.

A hybrid approach to the development of environmentally-friendly marine coatings, in which aspects of both antifouling coatings and fouling-release coatings are combined into a single coating composition, has been utilized. Antifouling character is imparted by chemically binding or "tethering" biocidal moieties to the coating matrix, while fouling-release character is imparted by creating a low surface energy, low modulus coating matrix. Since marine fouling often occurs as a staged process in which biofilm formation tends to trigger settlement of macrofoulers, it is believed that inhibition of biofilm formation using tethered, contact-active biocide moieties will, at a minimum, delay the fouling process.

A primary limitation of using a tethered biocide approach is that the length scale of interaction between tethered biocide moieties and microorganisms approaching the coating surface is much shorter than between approaching microorganisms and biocides being leached from the coating surface into the boundary layer. As a result, adsorption of molecular species such as proteins and/or polysaccharides from the aquatic environment onto the coating surface will eventually interfere with the antifouling effect by blocking the interaction between the tethered biocide moieties and approaching microorganisms. It is for this reason, that the coatings must also possess good fouling-release characteristics so that the surface can be easily cleaned periodically to regenerate antifouling efficacy.

Quaternary ammonium salt (QAS) moieties have been widely used as disinfectants for more than half a century. The high charge density associated with QAS moieties exerts a strong electrostatic interaction with the negatively-charged cell walls of many microorganisms, and kills them by contact. Surfaces coated with QAS-containing polymers have been shown to be very effective at killing a wide range of microorganisms such as Gram-positive and Gram-negative bacteria, yeasts, and molds.

Since QAS moieties provide effective antimicrobial activity through a contact mechanism, the creation of hybrid antifouling/fouling-release coatings involved tethering QAS moieties to a polysiloxane matrix. Polysiloxane-based matrix-forming materials were chosen because previous work has clearly shown that this class of materials provides the best fouling-release character.

To facilitate a through investigation of QAS-functional polysiloxane coatings for the creation of novel, hybrid antifouling/fouling-release coatings, a combinatorial/high-throughput methodology was utilized. The application of a combinatorial/high-throughput approach allows for multiple compositional variables to be investigated simultaneously which enables extensive structure-property relationships to be developed.

Materials. Table 9 provides a description of most of the starting materials used for the investigation (PDMS=polydimethylsiloxane). All reagents were used as received from the vendor.

TABLE 9

| Material ID | Supplier ID | Description | Supplier |
|---|---|---|---|
| 2K-PDMS | DMS-S15 | 2,000 g./mole silanol terminated PDMS | Gelest |
| 18K-PDMS | DMS-S27 | 18,000 g./mole silanol terminated PDMS | Gelest |
| 49K-PDMS | DMS-S35 | 49,000 g./mole silanol terminated PDMS | Gelest |

TABLE 9-continued

| Material ID | Supplier ID | Description | Supplier |
|---|---|---|---|
| Ph | SIT 8395 | n-(trimethoxysilyethyl)benzyl-n,n,n trimethylammoniumchloride | Gelest |
| C14 | SIT 7090 | tetradecyldimethyl(3-trimethoxysilylpropyl) ammoniumchloride | Gelest |
| C1 | SIT 8415 | n-trimethoxysilylpropyl-n,n,n-trimethylammoniumchloride | Gelest |
| C18 | SIO 6620 | octadecyldimethyl(3-trimethoxysilylpropyl) ammoniumchloride | Gelest |
| MeAcS | SIM 6519 | methyltriacetoxysilane | Gelest |
| TBAF | 1.0 M TBAF | 1.0 molar tetrabutylammoniumfluoride in tetrahydrofuran | Aldrich |
| Toluene | Toluene | toluene | VWR |
| MIBK | 4-Methyl-2-pentanone | 4-Methyl-2-pentanone | Alfa Aesar |
| DC 3140 | DC 3140 | Commercially-available silicone coating | Dow-Corning |
| DMSO | dimethylsulfoxide | dimethylsulfoxide | Aldrich |
| IS | Intersleek | Commercially-available silicone fouling-release coating | International Intersleek |
| T2 | Silastic-T2 | Commercially-available silicone coating | Dow-Corning |

Tables 10-12 provide the compositions of each of the coating solutions used for the investigation. Table 10 provides the composition of coating solutions based on 2K-PDMS (all values are in grams).

TABLE 10

| Coating | 2K-PDMS | Ph | C1 | C14 | C18 | MeAc | TBAF | toluene |
|---|---|---|---|---|---|---|---|---|
| 2K-no QAS | 3.5 | 0.000 | 0.000 | 0.000 | 0.000 | 0.525 | 0.525 | 0.00 |
| 2K-Ph-0.05 | 3.5 | 0.097 | 0.000 | 0.000 | 0.000 | 0.525 | 0.525 | 0.00 |
| 2K-Ph-0.10 | 3.5 | 0.194 | 0.000 | 0.000 | 0.000 | 0.525 | 0.525 | 0.00 |
| 2K-Ph-0.15 | 3.5 | 0.292 | 0.000 | 0.000 | 0.000 | 0.525 | 0.525 | 0.00 |
| 2K-Ph-0.20 | 3.5 | 0.389 | 0.000 | 0.000 | 0.000 | 0.525 | 0.525 | 0.00 |
| 2K-Ph-0.25 | 3.5 | 0.486 | 0.000 | 0.000 | 0.000 | 0.525 | 0.525 | 0.00 |
| 2K-Ph-0.30 | 3.5 | 0.584 | 0.000 | 0.000 | 0.000 | 0.525 | 0.525 | 0.00 |
| 2K-C1-0.05 | 3.5 | 0.000 | 0.090 | 0.000 | 0.000 | 0.525 | 0.525 | 0.00 |
| 2K-C1-0.10 | 3.5 | 0.000 | 0.180 | 0.000 | 0.000 | 0.525 | 0.525 | 0.00 |
| 2K-C1-0.15 | 3.5 | 0.000 | 0.270 | 0.000 | 0.000 | 0.525 | 0.525 | 0.00 |
| 2K-C1-0.20 | 3.5 | 0.000 | 0.360 | 0.000 | 0.000 | 0.525 | 0.525 | 0.00 |
| 2K-C1-0.25 | 3.5 | 0.000 | 0.451 | 0.000 | 0.000 | 0.525 | 0.525 | 0.00 |
| 2K-C1-0.30 | 3.5 | 0.000 | 0.541 | 0.000 | 0.000 | 0.525 | 0.525 | 0.00 |
| 2K-C14-0.05 | 3.5 | 0.000 | 0.000 | 0.154 | 0.000 | 0.525 | 0.525 | 0.00 |
| 2K-C14-0.10 | 3.5 | 0.000 | 0.000 | 0.308 | 0.000 | 0.525 | 0.525 | 0.00 |
| 2K-C14-0.15 | 3.5 | 0.000 | 0.000 | 0.462 | 0.000 | 0.525 | 0.525 | 0.00 |
| 2K-C14-0.20 | 3.5 | 0.000 | 0.000 | 0.616 | 0.000 | 0.525 | 0.525 | 0.00 |
| 2K-C14-0.25 | 3.5 | 0.000 | 0.000 | 0.770 | 0.000 | 0.525 | 0.525 | 0.00 |
| 2K-C14-0.30 | 3.5 | 0.000 | 0.000 | 0.924 | 0.000 | 0.525 | 0.525 | 0.00 |
| 2K-C18-0.05 | 3.5 | 0.000 | 0.000 | 0.000 | 0.144 | 0.525 | 0.525 | 0.00 |
| 2K-C18-0.10 | 3.5 | 0.000 | 0.000 | 0.000 | 0.289 | 0.525 | 0.525 | 0.00 |
| 2K-C18-0.15 | 3.5 | 0.000 | 0.000 | 0.000 | 0.434 | 0.525 | 0.525 | 0.00 |
| 2K-C18-0.20 | 3.5 | 0.000 | 0.000 | 0.000 | 0.579 | 0.525 | 0.525 | 0.00 |
| 2K-C18-0.25 | 3.5 | 0.000 | 0.000 | 0.000 | 0.723 | 0.525 | 0.525 | 0.00 |
| 2K-C18-0.30 | 3.5 | 0.000 | 0.000 | 0.000 | 0.868 | 0.525 | 0.525 | 0.00 |

Table 11 provides the composition of coating solutions based on 18K-PDMS (all values are in grams).

TABLE 11

| Coating | 18K-PDMS | Ph | C1 | C14 | C18 | MeAc | TBAF | toluene |
|---|---|---|---|---|---|---|---|---|
| 18K-no QAS | 3.5 | 0.000 | 0.000 | 0.000 | 0.000 | 0.525 | 0.525 | 0.00 |
| 18K-Ph-0.05 | 3.5 | 0.097 | 0.000 | 0.000 | 0.000 | 0.525 | 0.525 | 0.00 |
| 18K-Ph-0.10 | 3.5 | 0.194 | 0.000 | 0.000 | 0.000 | 0.525 | 0.525 | 0.00 |
| 18K-Ph-0.15 | 3.5 | 0.292 | 0.000 | 0.000 | 0.000 | 0.525 | 0.525 | 0.00 |
| 18K-Ph-0.20 | 3.5 | 0.389 | 0.000 | 0.000 | 0.000 | 0.525 | 0.525 | 0.00 |
| 18K-Ph-0.25 | 3.5 | 0.486 | 0.000 | 0.000 | 0.000 | 0.525 | 0.525 | 0.00 |
| 18K-Ph-0.30 | 3.5 | 0.584 | 0.000 | 0.000 | 0.000 | 0.525 | 0.525 | 0.00 |
| 18K-C1-0.05 | 3.5 | 0.000 | 0.090 | 0.000 | 0.000 | 0.525 | 0.525 | 0.00 |
| 18K-C1-0.10 | 3.5 | 0.000 | 0.180 | 0.000 | 0.000 | 0.525 | 0.525 | 0.00 |

TABLE 11-continued

| Coating | 18K-PDMS | Ph | C1 | C14 | C18 | MeAc | TBAF | toluene |
|---|---|---|---|---|---|---|---|---|
| 18K-C1-0.15 | 3.5 | 0.000 | 0.270 | 0.000 | 0.000 | 0.525 | 0.525 | 0.00 |
| 18K-C1-0.20 | 3.5 | 0.000 | 0.360 | 0.000 | 0.000 | 0.525 | 0.525 | 0.00 |
| 18K-C1-0.25 | 3.5 | 0.000 | 0.451 | 0.000 | 0.000 | 0.525 | 0.525 | 0.00 |
| 18K-C1-0.30 | 3.5 | 0.000 | 0.541 | 0.000 | 0.000 | 0.525 | 0.525 | 0.00 |
| 18K-C14-0.05 | 3.5 | 0.000 | 0.000 | 0.154 | 0.000 | 0.525 | 0.525 | 0.00 |
| 18K-C14-0.10 | 3.5 | 0.000 | 0.000 | 0.308 | 0.000 | 0.525 | 0.525 | 0.00 |
| 18K-C14-0.15 | 3.5 | 0.000 | 0.000 | 0.462 | 0.000 | 0.525 | 0.525 | 0.00 |
| 18K-C14-0.20 | 3.5 | 0.000 | 0.000 | 0.616 | 0.000 | 0.525 | 0.525 | 0.00 |
| 18K-C14-0.25 | 3.5 | 0.000 | 0.000 | 0.770 | 0.000 | 0.525 | 0.525 | 0.00 |
| 18K-C14-0.30 | 3.5 | 0.000 | 0.000 | 0.924 | 0.000 | 0.525 | 0.525 | 0.00 |
| 18K-C18-0.05 | 3.5 | 0.000 | 0.000 | 0.000 | 0.144 | 0.525 | 0.525 | 0.00 |
| 18K-C18-0.10 | 3.5 | 0.000 | 0.000 | 0.000 | 0.289 | 0.525 | 0.525 | 0.00 |
| 18K-C18-0.15 | 3.5 | 0.000 | 0.000 | 0.000 | 0.434 | 0.525 | 0.525 | 0.00 |
| 18K-C18-0.20 | 3.5 | 0.000 | 0.000 | 0.000 | 0.579 | 0.525 | 0.525 | 0.00 |
| 18K-C18-0.25 | 3.5 | 0.000 | 0.000 | 0.000 | 0.723 | 0.525 | 0.525 | 0.00 |
| 18K-C18-0.30 | 3.5 | 0.000 | 0.000 | 0.000 | 0.868 | 0.525 | 0.525 | 0.00 |

Table 12 provides the composition of coating solutions based on 49K-PDMS (all values are in grams).

TABLE 12

| Coating | 49K-PDMS | Ph | C1 | C14 | C18 | MeAc | TBAF | toluene |
|---|---|---|---|---|---|---|---|---|
| 49K-no QAS | 3.5 | 0.000 | 0.000 | 0.000 | 0.000 | 0.525 | 0.525 | 0.875 |
| 49K-Ph-0.05 | 3.5 | 0.097 | 0.000 | 0.000 | 0.000 | 0.525 | 0.525 | 0.875 |
| 49K-Ph-0.10 | 3.5 | 0.194 | 0.000 | 0.000 | 0.000 | 0.525 | 0.525 | 0.875 |
| 49K-Ph-0.15 | 3.5 | 0.292 | 0.000 | 0.000 | 0.000 | 0.525 | 0.525 | 0.875 |
| 49K-Ph-0.20 | 3.5 | 0.389 | 0.000 | 0.000 | 0.000 | 0.525 | 0.525 | 0.875 |
| 49K-Ph-0.25 | 3.5 | 0.486 | 0.000 | 0.000 | 0.000 | 0.525 | 0.525 | 0.875 |
| 49K-Ph-0.30 | 3.5 | 0.584 | 0.000 | 0.000 | 0.000 | 0.525 | 0.525 | 0.875 |
| 49K-C1-0.05 | 3.5 | 0.000 | 0.090 | 0.000 | 0.000 | 0.525 | 0.525 | 0.875 |
| 49K-C1-0.10 | 3.5 | 0.000 | 0.180 | 0.000 | 0.000 | 0.525 | 0.525 | 0.875 |
| 49K-C1-0.15 | 3.5 | 0.000 | 0.270 | 0.000 | 0.000 | 0.525 | 0.525 | 0.875 |
| 49K-C1-0.20 | 3.5 | 0.000 | 0.360 | 0.000 | 0.000 | 0.525 | 0.525 | 0.875 |
| 49K-C1-0.25 | 3.5 | 0.000 | 0.451 | 0.000 | 0.000 | 0.525 | 0.525 | 0.875 |
| 49K-C1-0.30 | 3.5 | 0.000 | 0.541 | 0.000 | 0.000 | 0.525 | 0.525 | 0.875 |
| 49K-C14-0.05 | 3.5 | 0.000 | 0.000 | 0.154 | 0.000 | 0.525 | 0.525 | 0.875 |
| 49K-C14-0.10 | 3.5 | 0.000 | 0.000 | 0.308 | 0.000 | 0.525 | 0.525 | 0.875 |
| 49K-C14-0.15 | 3.5 | 0.000 | 0.000 | 0.462 | 0.000 | 0.525 | 0.525 | 0.875 |
| 49K-C14-0.20 | 3.5 | 0.000 | 0.000 | 0.616 | 0.000 | 0.525 | 0.525 | 0.875 |
| 49K-C14-0.25 | 3.5 | 0.000 | 0.000 | 0.770 | 0.000 | 0.525 | 0.525 | 0.875 |
| 49K-C14-0.30 | 3.5 | 0.000 | 0.000 | 0.924 | 0.000 | 0.525 | 0.525 | 0.875 |
| 49K-C18-0.05 | 3.5 | 0.000 | 0.000 | 0.000 | 0.144 | 0.525 | 0.525 | 0.875 |
| 49K-C18-0.10 | 3.5 | 0.000 | 0.000 | 0.000 | 0.289 | 0.525 | 0.525 | 0.875 |
| 49K-C18-0.15 | 3.5 | 0.000 | 0.000 | 0.000 | 0.434 | 0.525 | 0.525 | 0.875 |
| 49K-C18-0.20 | 3.5 | 0.000 | 0.000 | 0.000 | 0.579 | 0.525 | 0.525 | 0.875 |
| 49K-C18-0.25 | 3.5 | 0.000 | 0.000 | 0.000 | 0.723 | 0.525 | 0.525 | 0.875 |
| 49K-C18-0.30 | 3.5 | 0.000 | 0.000 | 0.000 | 0.868 | 0.525 | 0.525 | 0.875 |

A polyurethane (Pu) was used as a reference coating for fouling-release studies. The Pu coating was prepared by dissolving 3.9 g. of Tone Polyol 0305 (Dow Chemical), 10.9 g. of Tolonate XIDT (Rhodia), and 0.097 g. of a 1.0 weight percent solution of dibutyltin diacetate in methyl n-amyl ketone (Aldrich) in 6.21 g. of Sherwin Williams Reducer No. 15.

Coating Preparation. An automated coating formulation system manufactured by Symyx Discovery Tools, Inc. was used to prepare coating solutions. Materials were dispensed into 8 mL glass vials using a robotic pipette having interchangeable tips and mixed with a magnetic stir bar.

Coating Application. Samples for surface energy measurements, dynamic water contact angle hysteresis measurements, and surface morphology characterization were prepared using a drawdown bar. Drawdowns were made over aluminum panels and curing was achieved by allowing the coatings to lie horizontally for 24 hours at ambient conditions followed by a 12 hour heat treatment at 50° C.

For high throughput measurements involving the microorganisms, Cellulophaga lytica and Navicula incerta, each coating solution was deposited into a 24 well array plate (6 columns and 4 rows) modified with epoxy primed aluminum discs in each well. The deposition was done such that a given coating composition occupied an entire column of the 24 well array plate (4 replicate coatings per array plate). The volume of coating solution transferred to each well was 0.25 mL. In addition to experimental coatings, each array plate also contained a silicone reference coating (35% by weight solution of DC 3140 in 4-methyl-2-pentanone) which was used to compare coating performance among the plates. Coatings were allowed to cure for 24 hours at room temperature, followed by an additional 24 hours at 50° C.

For measurements involving Ulva sporelings, each coating solution was deposited into all the wells of a 24 well array plate modified with epoxy primed aluminum discs using 0.25 mL of coating solution per well. Coatings were allowed to cure for 24 hours at room temperature, followed by an additional 24 hours at 50° C.

Coating Surface Characterization. An automated surface energy measurement unit manufactured by Symyx Discovery Tools, Incorporated and First Ten Angstroms was used to measure coating surface energy. The instrument robotically deposited droplets of water and methylene iodide (MI) on a coating surface and a CCD camera was used to automatically image the droplets. Automated image analysis was then conducted to determine contact angles. Three droplets of water and MI were used for each measurement. Surface energy was calculated from the contact angle data using the Owens-Wendt equation.

Water contact angle hysteresis was measured using the same automated surface energy measurement unit used to measure surface energy. Advancing contact angle ($0_A$) was measured by robotically adding water to a water droplet residing on the coating surface using an addition rate of 0.2 μL/s and monitoring changes in contact angle with time; while receding contact angle ($0_R$) was measured by monitoring contact angle as water was withdrawn from the droplet using a withdrawal rate of 0.2 μL/s. The first image was taken after 20 seconds and subsequent images were taken every 10 seconds. The total duration of the water addition was 70 seconds as was the total duration of water removal. $0_A$ was determined by averaging the second to fifth data points during water addition while $0_R$ was determined by averaging the last four data points. The difference between $0_A$ and $0_R$ was reported as the contact angle hysteresis.

Coating surface morphology was characterized using atomic force microscopy (AFM). The instrument utilized was a Dimension 3100® microscope with a Nanoscope IIIa controller from Veeco Incorporated. Experiments were carried out in tapping mode at ambient conditions and both topographical and phase images were collected. A silicon probe with a spring constant of 0.1-0.4 N/m and resonant frequency of 17-24 kHz was used. The set point ratio for collection of images was 0.8-0.9.

To obtain elemental analysis of the coating surfaces, samples were mounted on aluminum mounts and coated with gold using a Technics Hummer II sputter coater. Images were obtained using a JEOL JSM-6300 Scanning Electron Microscope. Elemental information was obtained via a Thermo Noran EDS detector using a VANTAGE Digital Acquisition Engine.

Characterization of Antifouling and Fouling-Release Characteristics. Biological assays were used to characterize the antifouling and fouling-release characteristics of the coatings. Four different biological assays were utilized. A leachate toxicity assay was used to determine if antifouling character was due to a leaching effect or a surface contact effect. A bacterial biofilm retention assay was used to characterize antifouling behavior toward a marine bacterium, *Cellulophaga lytica*. An algal biofilm growth assay was used to characterize antifouling behavior toward a marine diatom, *Navicula incerta*. An *Ulva* sporeling (young plant) removal assay was used to characterize fouling-release characteristics.

Leachate Toxicity Assay. Coating arrays were immersed in a recirculating water bath for at least one week to remove leachable residues from the coatings. The preconditioned coatings were then incubated in 1.0 mL of growth medium for 18 hours and the resultant coating leachates collected. 0.05 ml, of a *C. lytica* suspension in biofilm growth medium (BGM) (~$10^7$ cells.mL$^{-1}$) or 0.05 mL of a *N. incerta* suspension in Guillard's F/2 medium (~$10^5$ cells.mL$^{-1}$) was added to 1.0 mL of coating leachate. 0.2 mL of coating leachate, with the addition of *C. lytica* or *N. incerta*, was transferred in triplicate to a 96-well array plate. *C. lytica*-containing array plates were incubated for 18 hours at 28° C., while *N. incerta*-containing array plates were incubated for 48 hours at 18° C. in an illuminated growth cabinet with a 16:8 light:dark cycle (photon flux density 33 μmol m$^{-2}$s$^{-1}$). *C. lytica*-containing array plates were rinsed three times with deionized water and the retained biofilms stained with 0.5 mL of crystal violet dye. 0.5 mL of glacial acetic acid was added to each coating well to extract the crystal violet dye and absorbance measurements were made at 600 nm with a multi-well plate reader. *N. incerta*-containing array plates were characterized by extracting biofilms with DMSO and quantifying chlorophyll concentration using fluorescence spectroscopy (Excitation: 360 nm; Emission: 670 nm). A reduction in the amount of bacterial biofilm retention or algal growth compared to a positive growth control (i.e., organism in fresh growth media) was considered to be a consequence of toxic components being leached from the coating into the overlying medium.

Bacterial Biofilm Retention Assay. The rapid evaluation of bacterial biofilm retention on coatings cast in 24-well array plates has been reported previously. Briefly, array plates were inoculated with a 1.0 mL suspension of *C. lytica* in BGM (~$10^7$ cells/mL). The plates were then incubated statically in a 28° C. incubator for 18 hours to facilitate bacterial attachment and subsequent colonization. The plates were then rinsed three times with 1.0 mL of deionized water to remove any planktonic or loosely attached biofilm. The biofilm retained on each coating surface after rinsing was then stained with crystal violet dye. Once dry, the crystal violet dye was extracted from the biofilm with the addition of 0.5 mL of glacial acetic acid and the resulting eluate was measured for absorbance at 600 nm. The absorbance values were directly proportional to the amount of biofilm retained on the coating surface. Each data point represented the mean absorbance value of three replicate samples and was reported as a relative reduction compared to a control coating. Error bars represent one standard deviation.

Diatom Biofilm Growth Assay. The rapid evaluation of algal growth on coatings cast in 24-well array plates has been reported previously. Briefly, a 1.0 mL suspension of the marine diatom, *N. incerta*, in F/2 medium (~$10^5$ cells.mL$^{-1}$) was delivered to each well of the array plate. Plates were incubated statically for 48 hours at 18° C. in an illuminated growth cabinet with a 16:8 light:dark cycle (photon flux density 33 μmol m$^{-2}$ s$^{-1}$). Biomass was quantified by the fluorescence of chlorophyll which was extracted from the biomass with 1.0 mL of DMSO. The plates were incubated in darkness for 30 minutes and 0.2 mL of the resulting eluate was pipetted from each well into wells of a 96 well-plate and the fluorescence measured (Excitation wavelength: 360 nm; Emission wavelength: 670 nm). Fluorescence was recorded as relative fluorescence units (RFU). Each data point was represented by the mean RFU value of three replicates and reported as a relative reduction compared to a reference coating, DC 3140. Error bars represent one standard deviation.

*Ulva* Sporeling Removal Assay. *Ulva* (*Enteromorpha*) is a green macroalga that reproduces by producing large numbers of motile zoospores that rapidly settle and adhere to the substratum through the release of a glycoprotein adhesive(s). Settled spores germinate and grow into sporelings (young plants). The removal assay quantifies the strength of attachment of sporelings to the coating. The coatings in 24-well array plates were preleached in recirculating deionized water for 30 days. Just before the start of the experiment, each well of the 24-well plates was filled with deionized water, allowed to sit for 48 hours, and subsequently equilibrated in artificial water for two hours. The *Ulva* spore inoculum was adjusted to 5×$10^5$ spores mL$^{-1}$. Spores settled on the 24-well plates were grown for 6 days inside an illuminated incubator at 18° C. with a 16:8 light:dark cycle (photon flux density 65 μmol $m^{-2}s^{-1}$) with renewal of nutrients after 48 hours growth. After 6 days growth, the plates were water-jetted at 18, 43 and 89 kPa impact pressure. One row of the array plate (6 replicates) was not jetted while three rows were jetted using a different pressure for each row resulting in 6 replicates per pressure. Biomass was determined by extraction of chlorophyll as described for *Navicula*. Percentage removal was calculated from the mean chlorophyll concentration before and after water-jetting.

As shown in Scheme 4, the QAS-functional polysiloxanes investigated were derived from silanol-terminated PDMS, QAS-functional trimethyoxysilanes, and methyltriacetoxysilane. With this system, curing and QAS tethering occurred by a mixture of condensation reactions, as illustrated in Scheme 5. In addition to the condensation reactions, hydrolysis of methoxysilane groups and acetoxysilane groups occur to produce silanols which undergo condensation reactions.

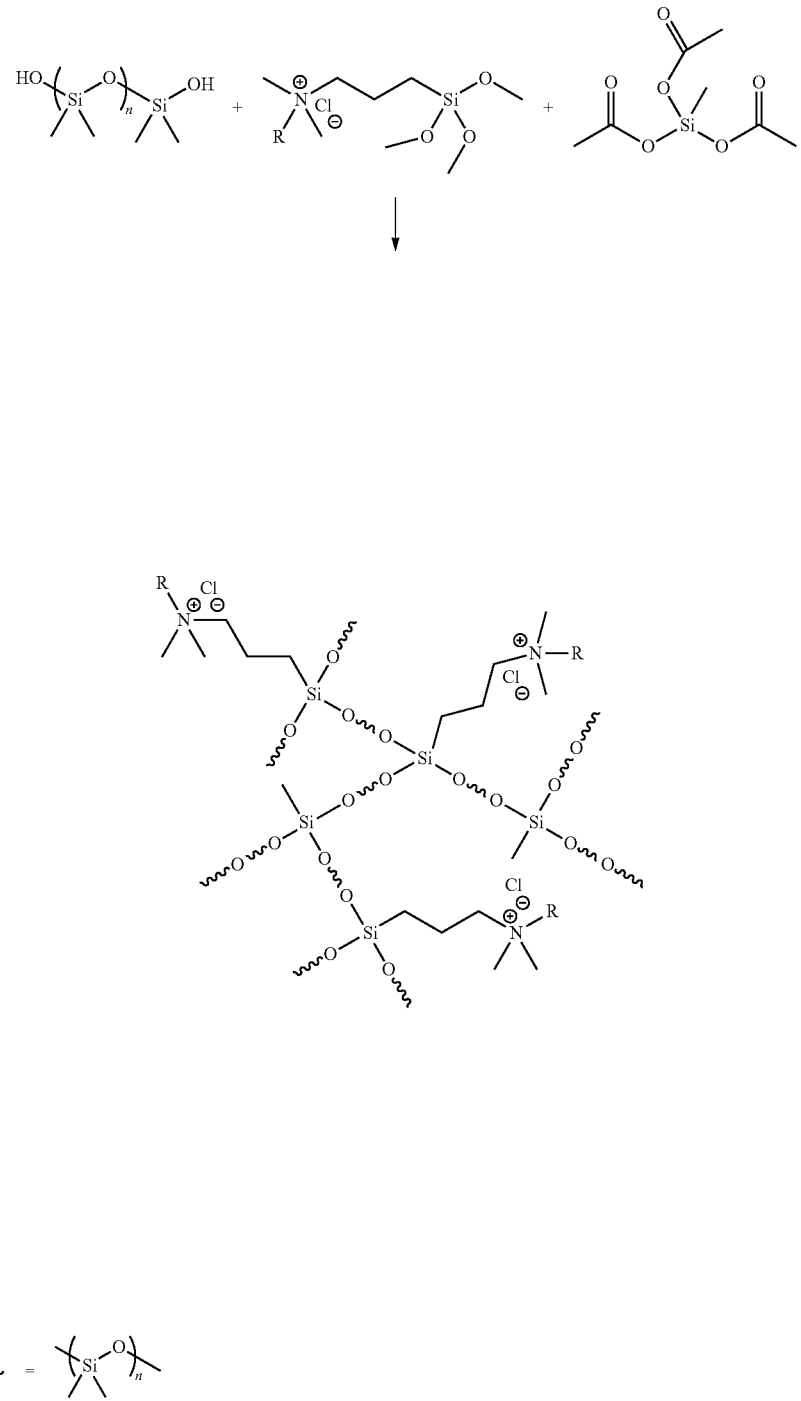

Scheme 4

Scheme 5

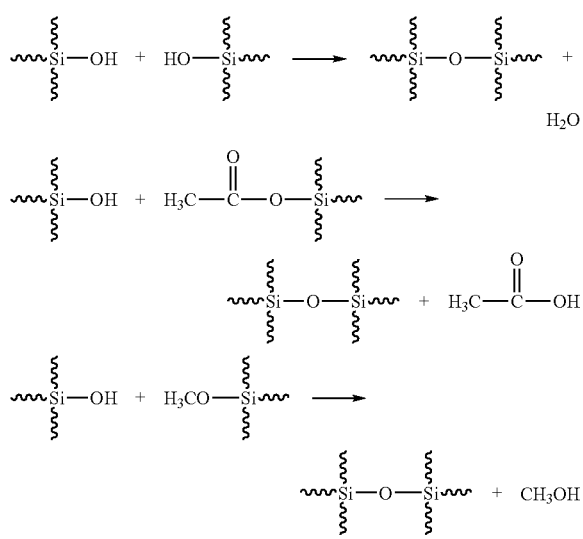

The variables investigated for this compositional space included QAS composition, QAS concentration, and silanol-terminated PDMS molecular weight. Four different QAS-functional trimethoxysilanes were chosen for the experiment, wherein alkyl chain length of the QAS was varied from a one carbon alkyl chain (C1) to an 18 carbon alkyl chain (C18):

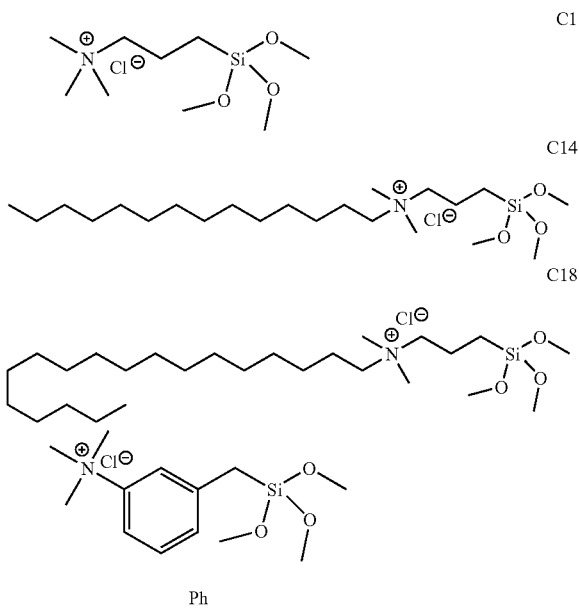

Figure 12:
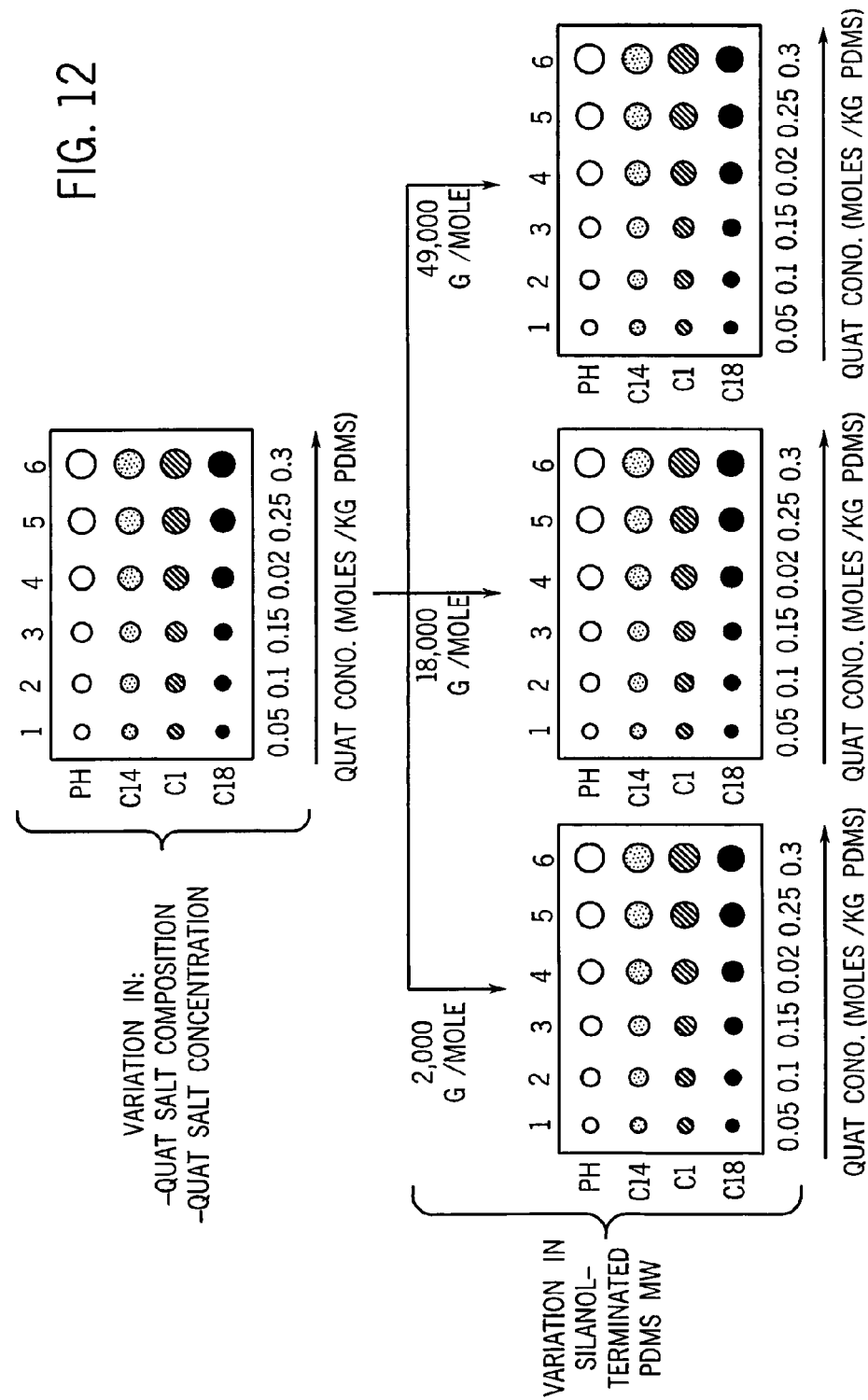
FIG. 12 shows a schematic illustration of the experimental design used for the investigation.
Figure 13A:
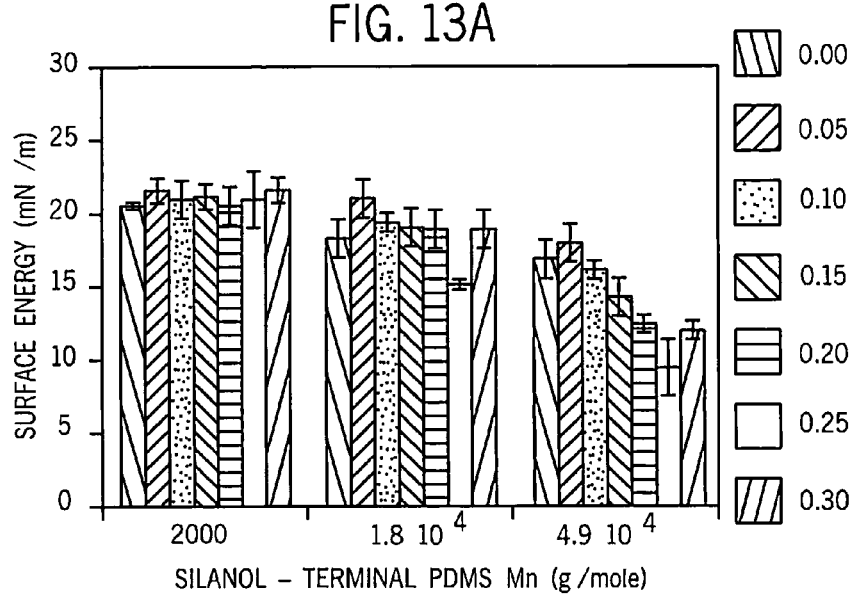
FIG. 13 shows surface energy as a function of QAS concentration in moles/kg of PDMS for coatings derived from (A), (B) Ph, (C) C14, and (D) C18; each data point is the mean of three replicates and error bars represent one standard deviation.
Figure 13B:
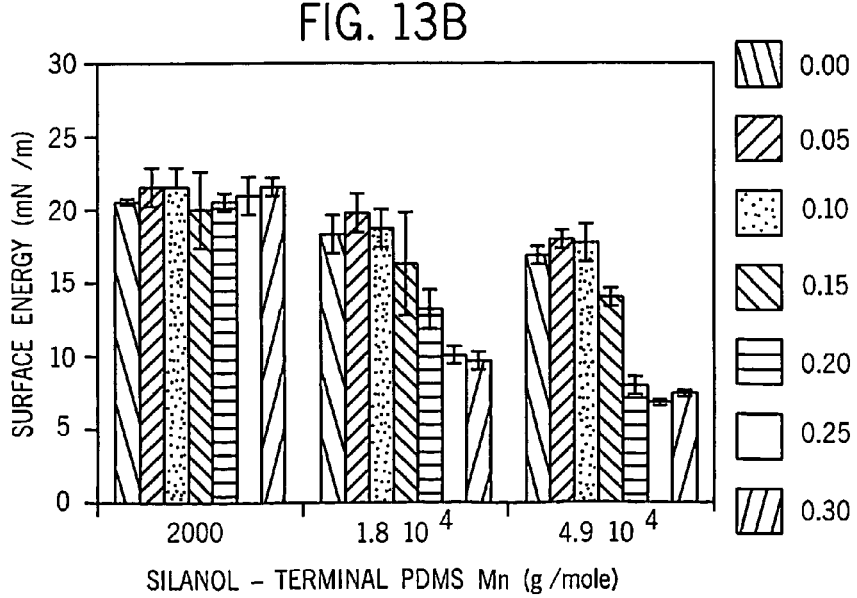
Figure 13C:
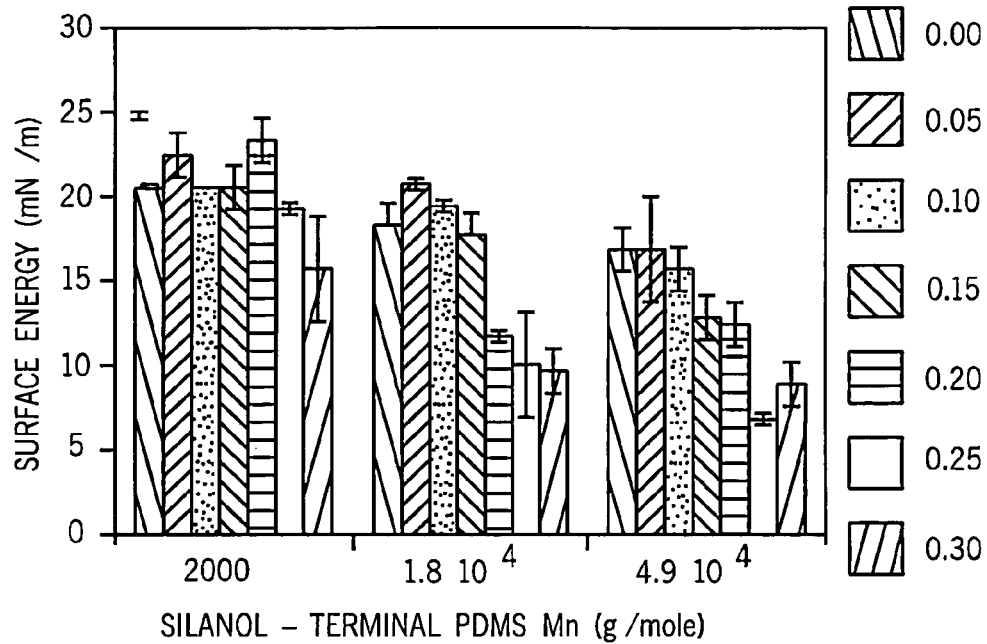
Figure 13D:
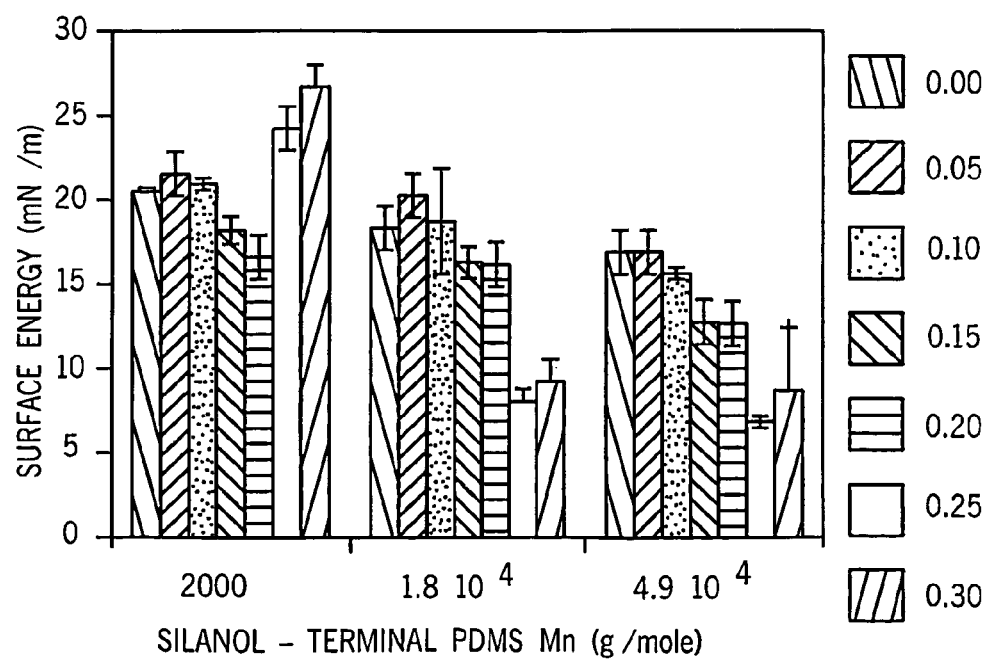

FIG. 12 displays a schematic of the experimental design. QAS concentration was varied at six levels while silanol-terminated PDMS molecular weight was varied at three levels. In addition to the 72 unique coating compositions described in FIG. 12, three QAS-free siloxane coatings were produced which varied with respect to silanol-terminated PDMS molecular weight. The application of the combinatorial/high-throughput methodology allowed for efficient and rapid synthesis and characterization of this relatively large number of coatings.

Figure 14A:
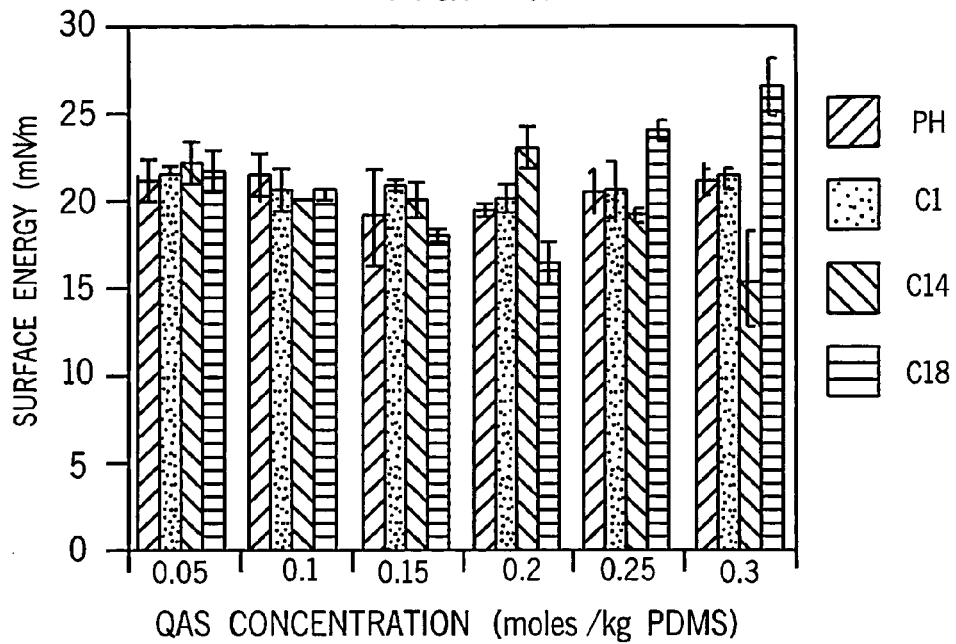
FIG. 14 shows surface energy as a function of QAS composition for coatings derived from (A) 2K-PDMS, (B) 18K-PDMS, and (C) 49K-PDMS; each data point is the mean of three replicates and error bars represent one standard deviation.
Figure 14B:
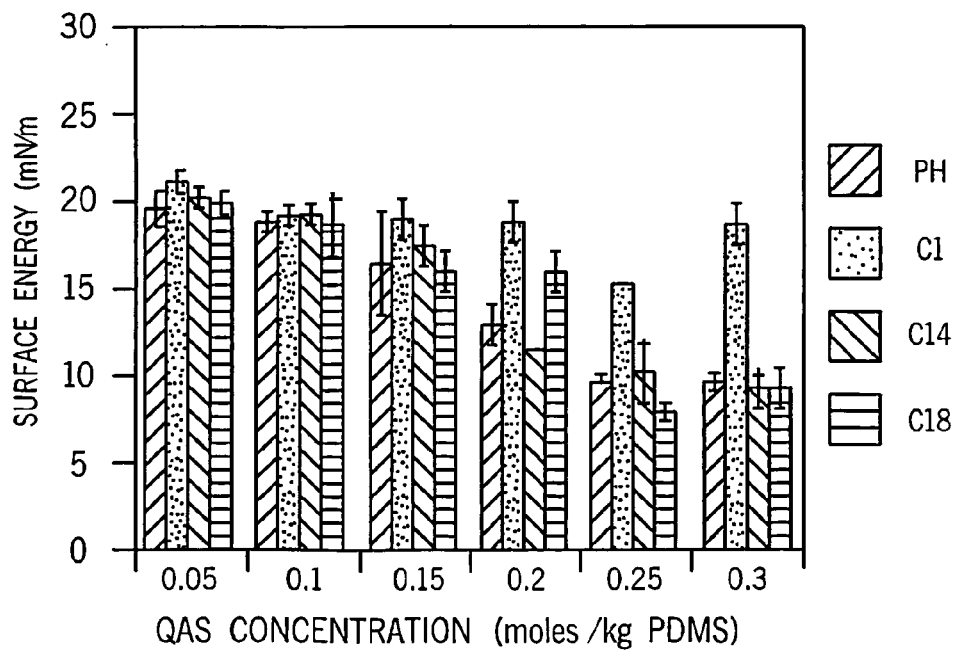
Figure 15A:
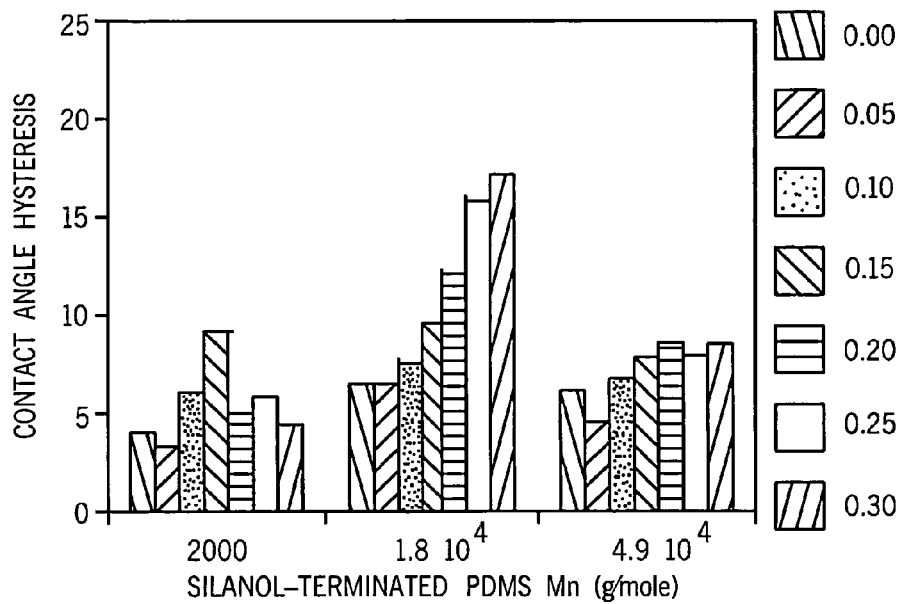
FIG. 15 shows water contact angle hysteresis as a function of QAS concentration in moles/kg of PDMS for coatings derived from (A) Cl, (B) Ph, (C) C14, and (D) C18.
Figure 15B:
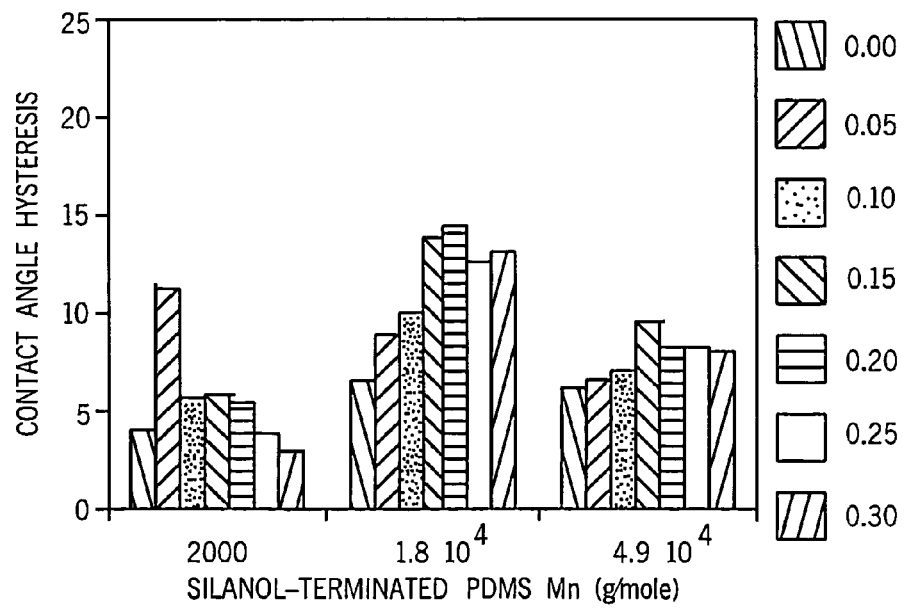
Figure 15C:
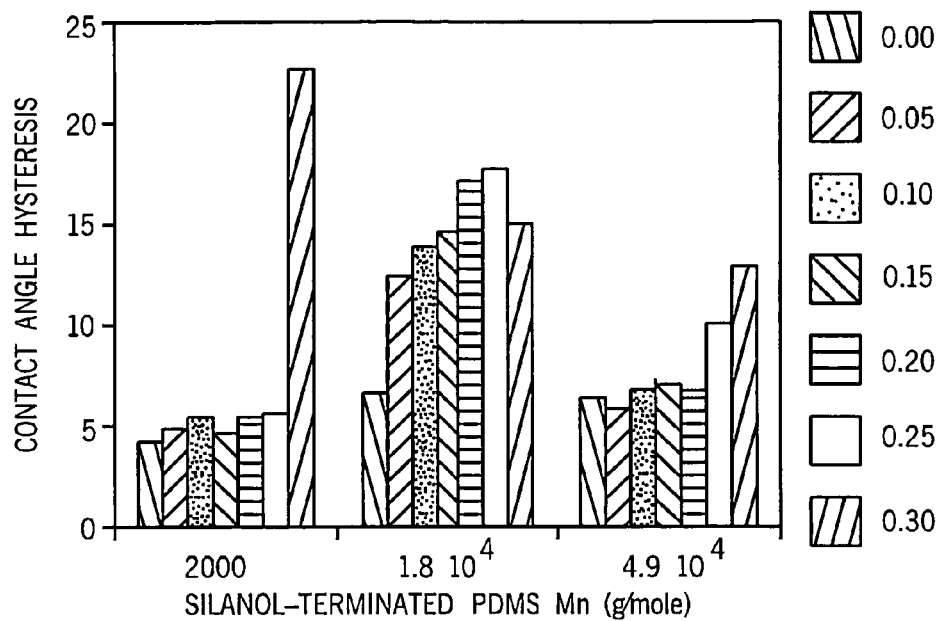
Figure 15D:
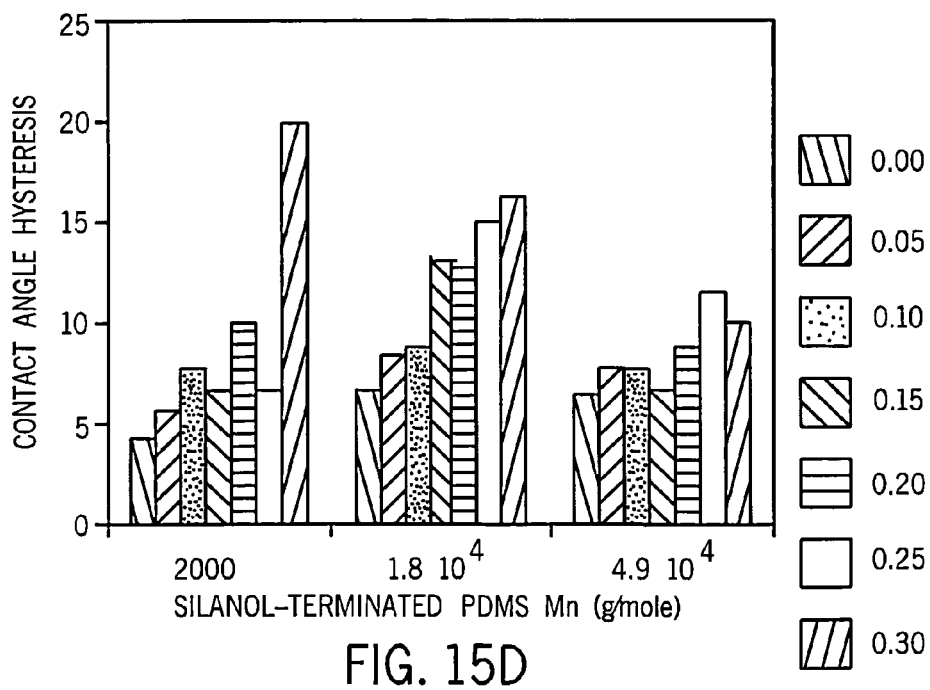

Surface Properties and Composition. Surface energy data plotted as a function of QAS concentration and QAS composition are shown in FIGS. 13 and 14, respectively. The results show that all three compositional variables effected surface energy. In addition, obvious interactions between compositional variables were observed.

The surface energy of coatings produced from the lowest molecular weight silanol-terminated PDMS, 2K-PDMS, did not vary much with QAS composition or concentration compared to coatings derived from the two higher molecular weight silanol-terminated PDMS polymers, 18K-PDMS and 49K-PDMS. Interestingly, for coatings derived from the two higher molecular weight silanol-terminated PDMS polymers, surface energy decreased with increasing QAS concentration. This result was counterintuitive considering the fact that QAS groups are quite hydrophilic due to their ionic nature.

Figure 16A:
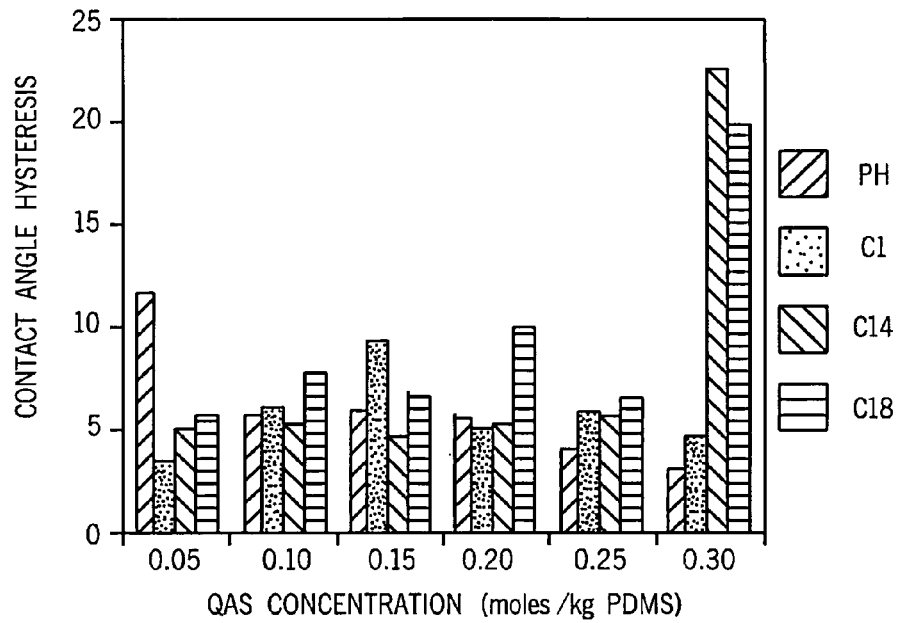
FIG. 16 shows water contact angle hysteresis as a function of QAS composition for coatings derived from (A) 2K-PDMS, (B) 18K-PDMS, and (C) 49K-PDMS.
Figure 16B:
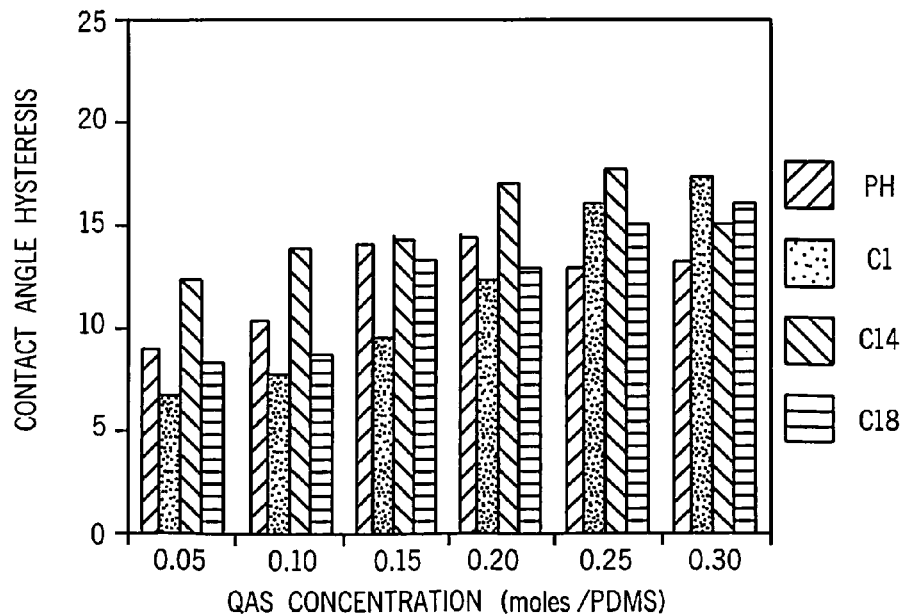
Figure 16C:
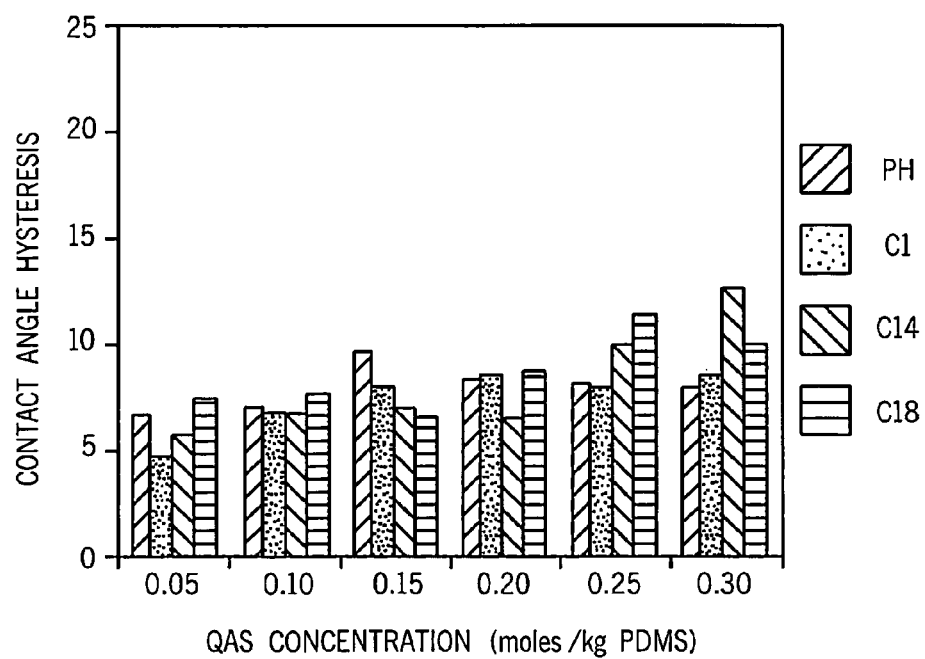

In addition to surface energy, water contact angle hysteresis (CAH) was measured. FIGS. 15 and 16 display CAH as a function of QAS concentration and QAS composition, respectively. CAH varied widely over the compositional space investigated. In general, it was found that CAH was the highest for coatings based on 18K-PDMS. Variations in CAH can be attributed to a variety of factors including variations in surface heterogeneity, roughness, and segmental polymer chain mobility. In order to understand the trends observed for surface energy and CAH, AFM was used to characterize coating surface morphology.

Figure 17:
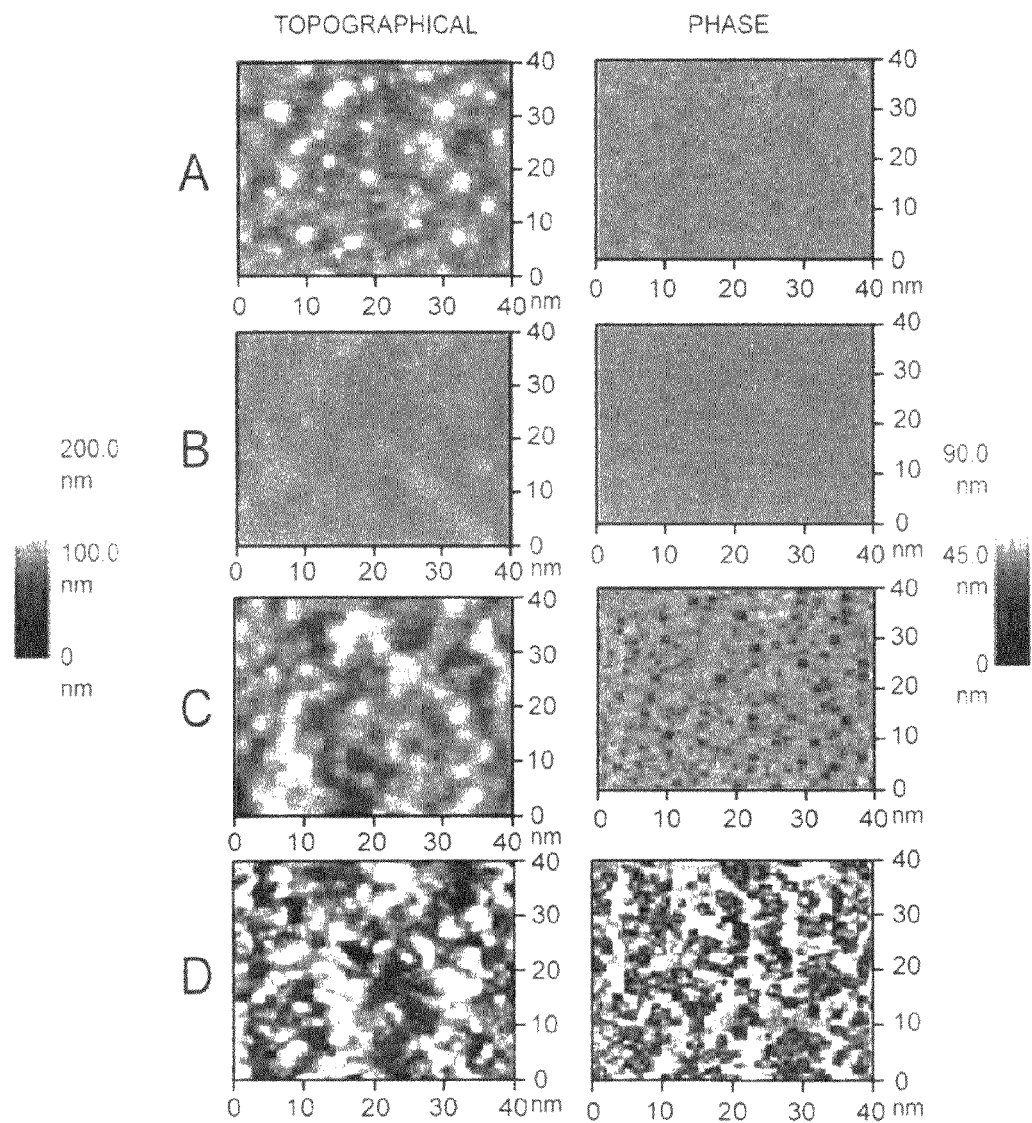
FIG. 17 shows AFM images of coatings (A) 18K-Ph-0.20, (B) 18K-Cl-0.20, (C) 18K-C14-0.20 and, (D) 18K-C18-0.20; each image shows a 40 micron square field.
Figure 18:
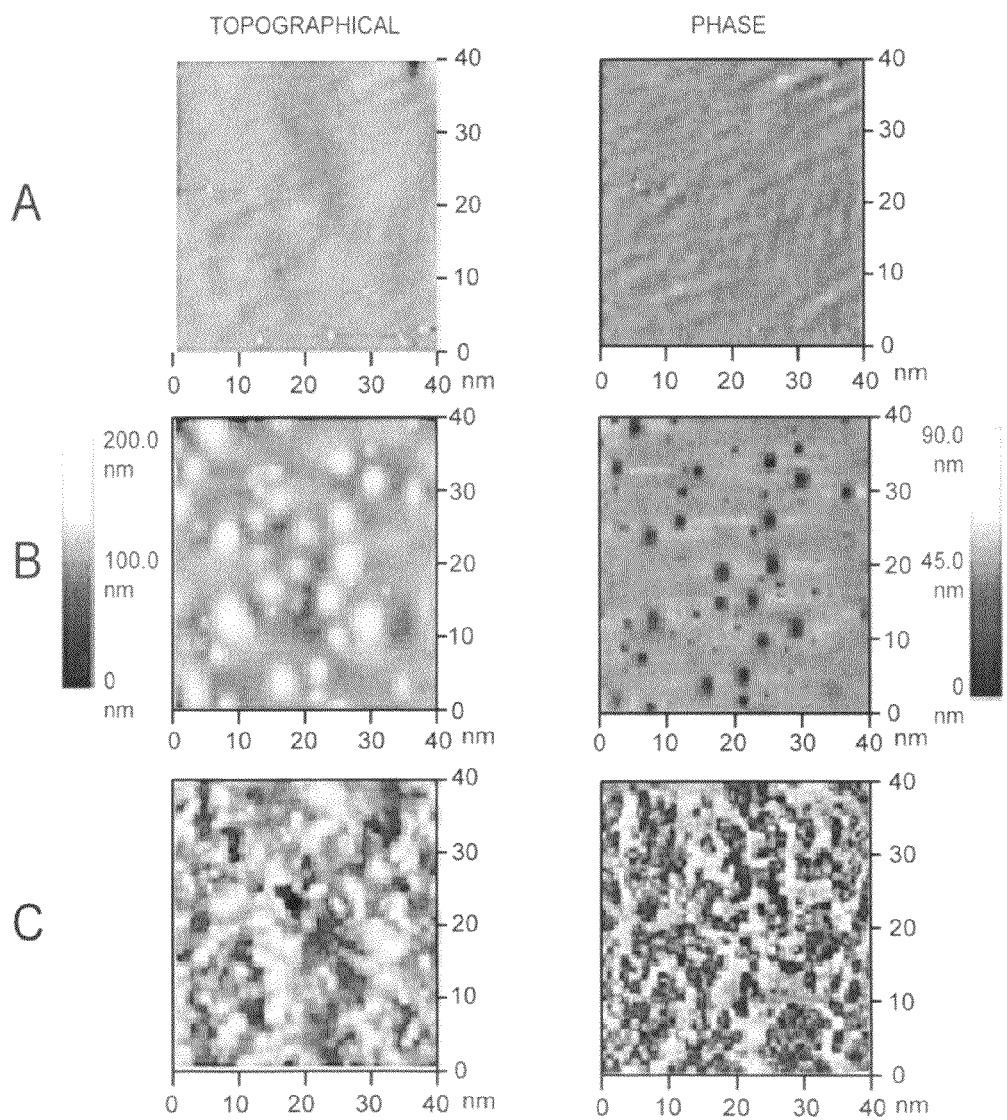
FIG. 18 shows AFM images of coatings (A) 18K-no QAS, (B) 18K-C18-0.10, and (C) 18K-C18-0.20; each image shows a 40 micron square field.
Figure 19:
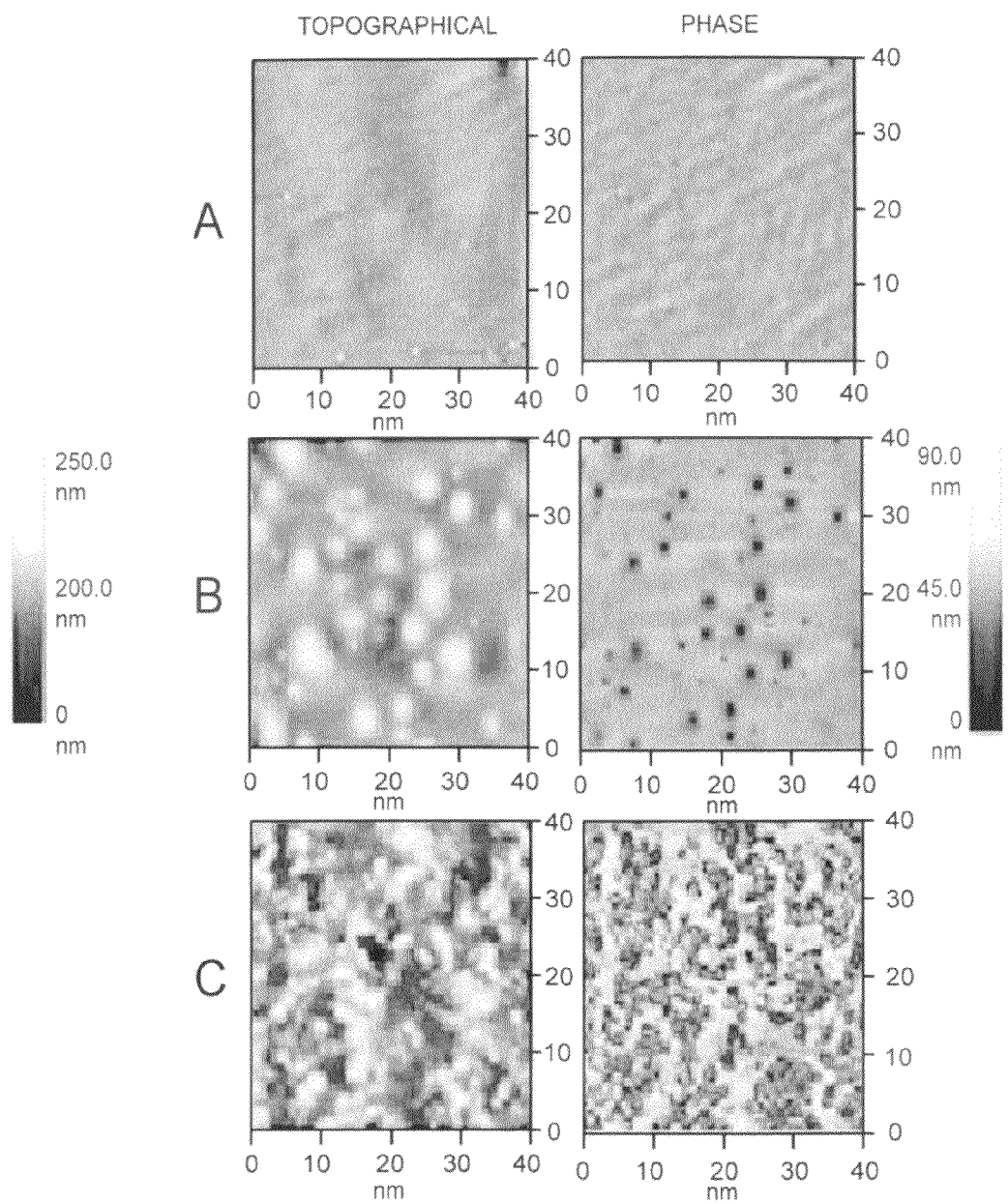
FIG. 19 shows AFM images of coatings (A) 2K-C18-0.20, (B) 18K-C18-0.20, and (C) 49K-C18-0.20; each image shows a 40 micron square field.

The effects of QAS composition, QAS concentration, and silanol-terminated PDMS molecular weight on surface morphology are illustrated in FIGS. 17, 18, and 19, respectively. The AFM images displayed in FIG. 17 were all obtained from coatings produced using the same silanol-terminated PDMS (18K-PDMS) and the same QAS concentration (0.20 moles/kg PDMS) enabling a direct comparison of the effect of QAS chemical composition. A comparison of the images obtained from coatings based on the aliphatic QAS moieties, C1, C14, and C18, clearly shows that surface heterogeneity increased with increasing QAS alkyl chain length. A relatively smooth, uniform surface morphology was obtained for the coating based on C1 while a relatively rough, two phase surface morphology consisting of interconnected surface protrusions in the 0.60 to 2.9 micron size range was observed for the C18-based coating. The images obtained for the coating based on C14 showed a two phase morphology consisting mostly of isolated protrusions in the 0.70 to 2.6 micron size range. Based on the data shown in Table 13 (Ra is mean roughness; Rq is root mean square roughness), the relative ranking of the coatings based on surface roughness was 18K-C18-0.20>18K-C14-0.20>18K-Ph-0.20>18K-C1-0.20, which is analogous to a ranking based on QAS molecular weight. Thus, it can be concluded that for analogous coatings at equivalent QAS molar concentration, coating surface roughness and heterogeneity increases with increasing QAS molecular weight.

TABLE 13

| Coating Composition | Ra (nm) | Rq (nm) |
| --- | --- | --- |
| 18K-PDMS | 3.72 | 6.22 |
| 2K-C18-0.10 | 2.57 | 3.25 |
| 2K-C18-0.20 | 6.46 | 8.53 |
| 18K-C18-0.10 | 9.89 | 13.38 |
| 18K-Ph-0.20 | 7.01 | 9.50 |
| 18K-C1-0.20 | 1.78 | 2.32 |
| 18K-C14-0.20 | 10.51 | 13.41 |

TABLE 13-continued

| Coating Composition | Ra (nm) | Rq (nm) |
|---|---|---|
| 18K-C18-0.20 | 21.87 | 28.35 |
| 49K-C18-0.20 | 1.6 | 2.28 |

FIG. 18 displays AFM images for coatings 18K-no QAS, 18K-C18-0.10, and 18K-C 18-0.20 enabling a comparison of the effect of QAS concentration at equivalent silanol-terminated PDMS molecular weight and equivalent QAS composition. As shown in FIG. 18, coating surface heterogeneity and surface roughness (Table 13) increased with increasing QAS concentration. Considering the difference in polarity between the QAS moieties and PDMS polymer chains, it is not surprising that a two phase morphology would exist for coatings containing relatively high levels of QAS. The increase in surface roughness with increasing QAS concentration explains the decrease in surface energy (FIG. 14b) and increase in CAH (FIG. 16b) observed with increasing QAS concentration for these coatings.

FIG. 19 displays AFM images for coatings that vary with respect to silanol-terminated PDMS molecular weight. All three coatings used for the comparison were derived from the same QAS (C18) and QAS concentration (0.20 moles/kg PDMS). The coating based on the lowest molecular weight silanol-terminated PDMS, 2K-PDMS, showed a relatively uniform and smooth surface morphology while the coatings based on the higher molecular weight silanol-terminated PDMSs, 18K-PDMS and 49K-PDMS, showed two phase surface morphologies. The relatively uniform surface morphology exhibited by the coating based on the 2K-PDMS agrees with the surface energy results displayed in FIG. 14a which shows a relatively small variation in surface energy with QAS composition and concentration.

A comparison of the AFM images and roughness data (Table 13) for 18K-C18-0.20 and 49K-C18-0.20 shows higher surface roughness and larger scale phase separation for 18K-C18-0.20 as compared to 49K-C18-0.20. As shown in FIG. 15, analogous coatings based on the 18K-PDMS generally showed higher CAH than coatings based on 2K-PDMS or 49K-PDMS which is consistent with a rougher, more heterogeneous surface morphology derived from the use of 18K-PDMS. The surface morphology for the coatings of interest results from a complex interaction between the thermodynamics and kinetics of film formation and curing. The coating solutions were one-phase; however, upon application to the substrate a two-phase morphology develops as solvent evaporates, crosslinking ensues, and viscosity increases. Considering the difference in chemical structure between PDMS repeat units and the QAS moieties, a relatively strong thermodynamic driving force for phase separation was expected. The only intermolecular interactions associated with PDMS repeat units are Vander Waals interactions while the QAS moieties can form ionic interactions between themselves. It has been previously shown that PDMS polymers containing pendant QAS groups form two-phase materials in which QAS-rich domains exist as a dispersed phase in the PDMS matrix. Thus interactions between the thermodynamics and kinetics of phase separation coupled with the rate of solvent evaporation, rate of crosslinking, and rate of the viscosity increase, results in a greater degree of phase separation for coatings based on 18K-PDMS as compared to those derived from 2K-PDMS or 49K-PDMS.

Since the QAS moieties provide the antimicrobial properties desired, it was of interest to characterize surface chemical composition of select coatings. Table 14 displays results obtained from energy dispersive X-ray spectroscopy (EDS) measurements in which the relative concentrations of silicon (Si), carbon (C), and chlorine (Cl) were measured. Observing relative differences in Cl content allowed for an understanding of the effects of the coating compositional variables on the concentration of QAS groups at the coating surface. A comparison of the Cl content for sample 49K-C14-0.10 to 49K-C14-0.20 and sample 49K-C18-0.10 to 49K-C18-0.20 shows that increasing QAS concentration in the coating formulation increases QAS concentration at the coating surface. A comparison of results for Cl content obtained for 18K-Ph-0.10 to analogous results obtained for 18K-C18-0.10 suggests that increasing the size of the alkyl group of the QAS moiety increases QAS concentration at the coating surface. The apparent increase in QAS surface concentration with increasing alkyl group chain length may be a result of a reduction in QAS surface free energy with increasing alkyl chain length. Since methylene groups are relatively nonpolar, increasing alkyl chain length would result in an overall reduction in QAS surface free energy.

TABLE 14

| | Element wt % ± one standard deviation | | |
|---|---|---|---|
| Sample ID | Si | C | Cl |
| 18K-Ph-0.10 | 46.92 ± 0.66 | 31.37 ± 2.72 | 0.11 ± 0.18 |
| 18K-C18-0.10 | 46.09 ± 0.28 | 35.70 ± 1.65 | 0.41 ± 0.08 |
| 49K-C14-0.10 | 56.05 ± 0.28 | 33.66 ± 1.58 | 0.61 ± 0.09 |
| 49K-C14-0.20 | 46.73 ± 0.50 | 34.63 ± 2.96 | 1.76 ± 0.18 |
| 49K-C18-0.10 | 53.87 ± 0.35 | 31.35 ± 1.82 | 0.62 ± 0.12 |
| 49K-C18-0.20 | 51.45 ± 0.34 | 31.77 ± 1.78 | 1.44 ± 0.12 |

Antifouling Character

Two different marine microorganisms, *C. lytica*, a marine bacterium, and *N. incerta*, a marine diatom, were used to assess the antifouling character of the coatings investigated. High-throughput screening methods based on measurements of *C. lytica* biofilm retention, *C. lytica* biofilm retraction, and *N. incerta* biofilm growth have been previously described in detail. Previous results obtained for silicone coatings using the high-throughput methods based on *C. lytica* were shown to correlate well with barnacle adhesion obtained from ocean immersion testing.

A key component for these screening methods is a preconditioning process followed by a leachate toxicity measurement prior to measuring antifouling efficacy. The preconditioning process involves immersion of coatings in a circulating water bath for at least a week to remove leachable coating components such as residual solvent, catalyst residues, and unreacted QASs from the coating. This process is essential for attributing the observation of antifouling character to a coating surface-associated phenomenon as opposed to a leaching phenomenon. To ensure that the preconditioning process was effective in removing leachable, toxic components from the coatings, a leachate toxicity measurement is made in addition to the antifouling measurement.

Figure 20A:
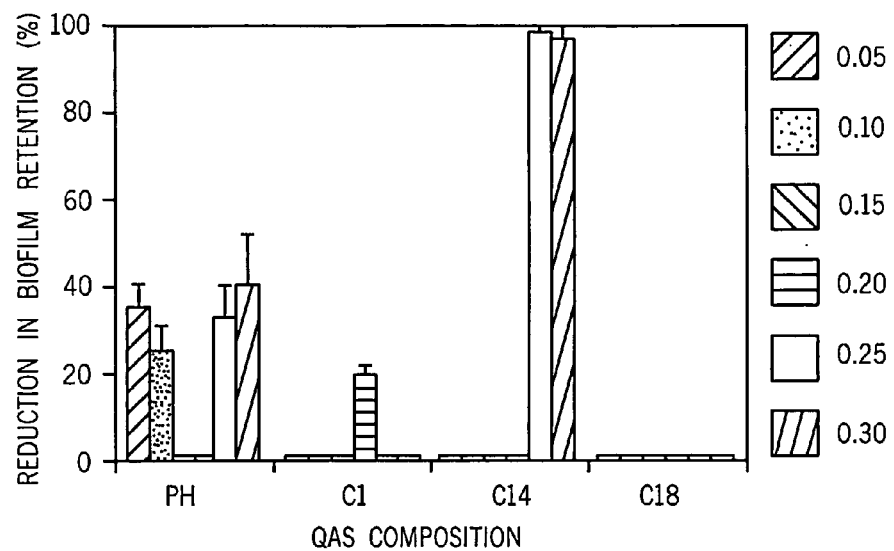
FIG. 20 shows leachate toxicity results for coatings derived from (A) 2K-PDMS, (B) 18K-PDMS, and (C) 49K-PDMS, using *C. Lytica*; each data point is the mean of three replicates and error bars represent one standard deviation.
Figure 20B:
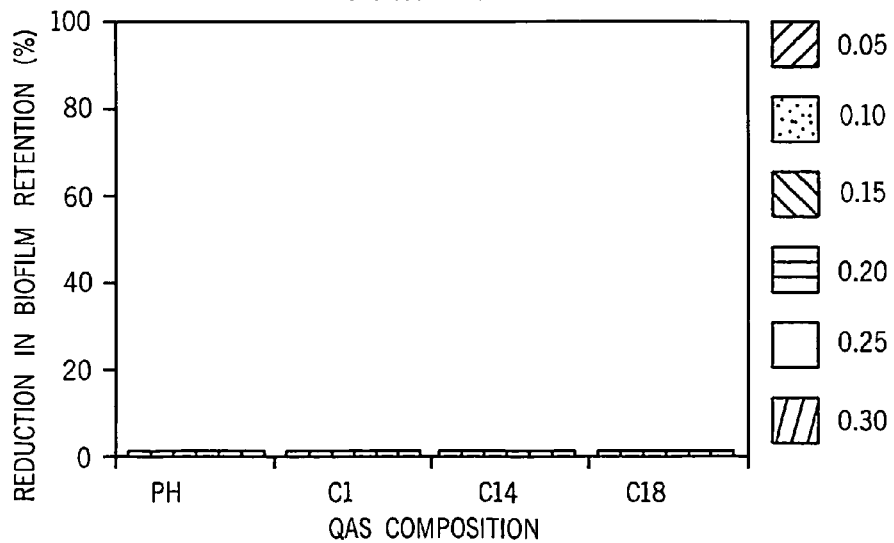
Figure 20C:
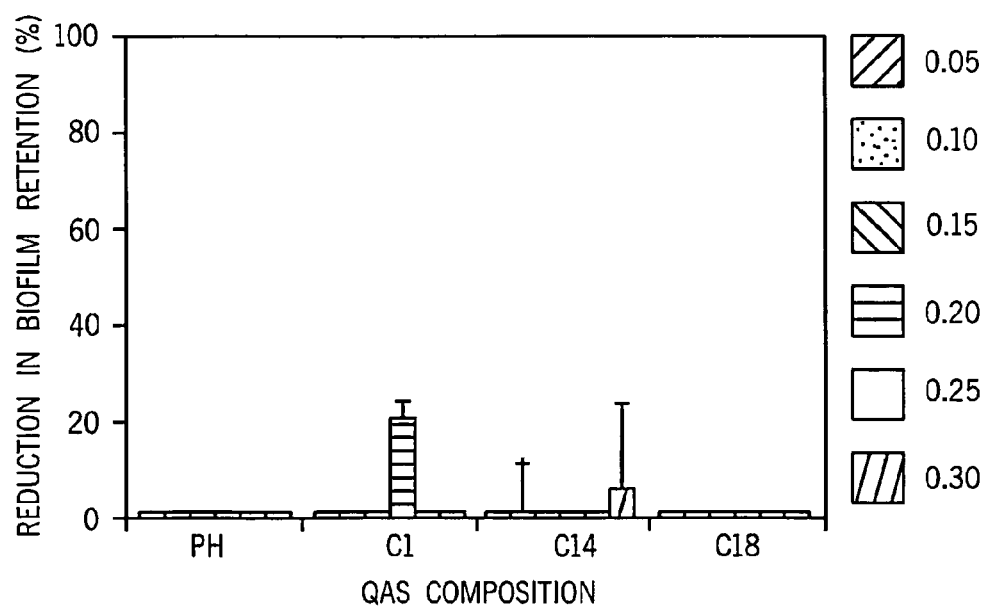
Figure 21A:
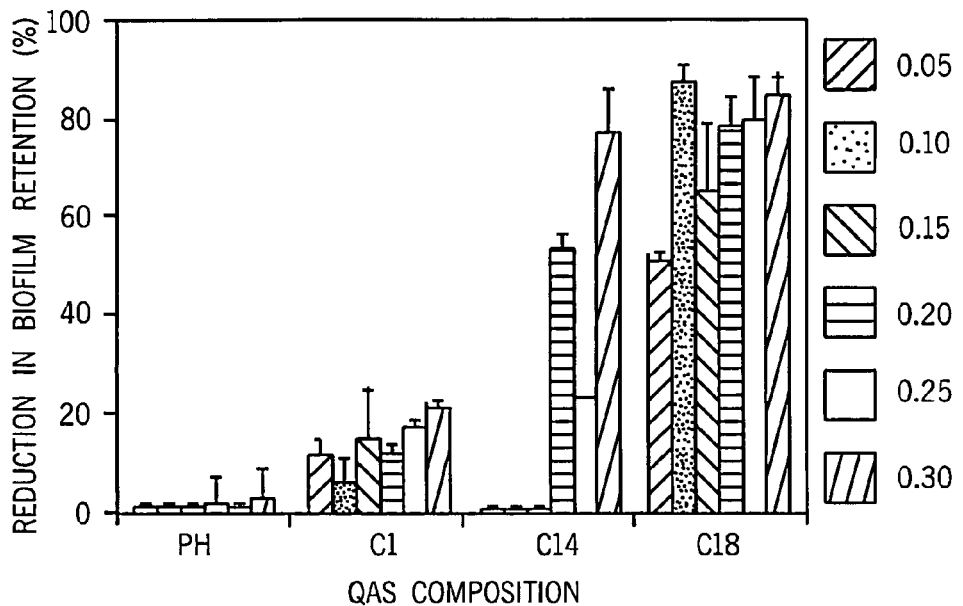
FIG. 21 shows *C. lytica* biofilm retention results for coatings derived from (A) 2K-PDMS, (B) 18K-PDMS, and (C) 49K-PDMS; each data point is the mean of three replicates, error bars represent one standard deviation, and "*" indicates that the sample showed leachate toxicity.
Figure 21B:
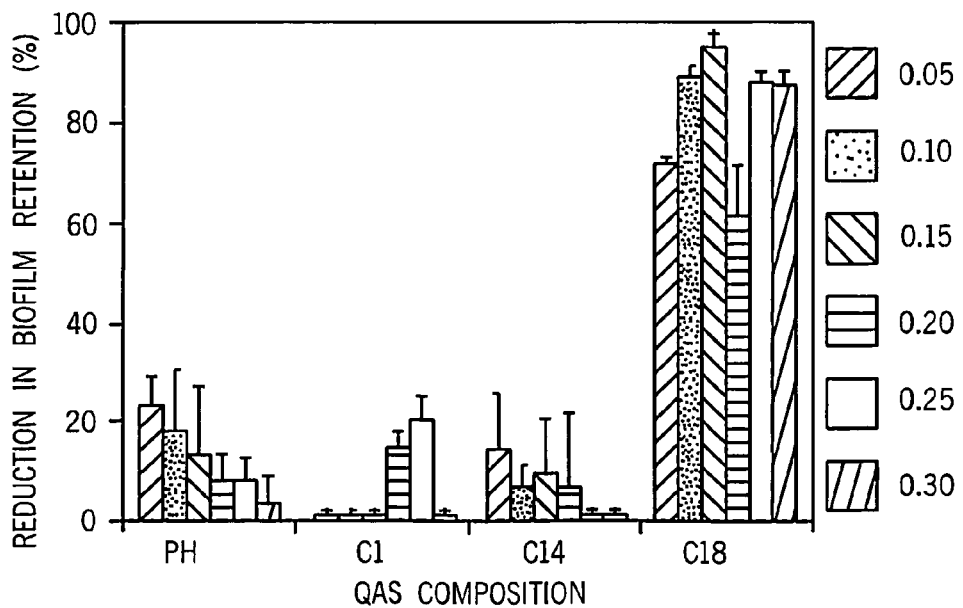
Figure 21C:
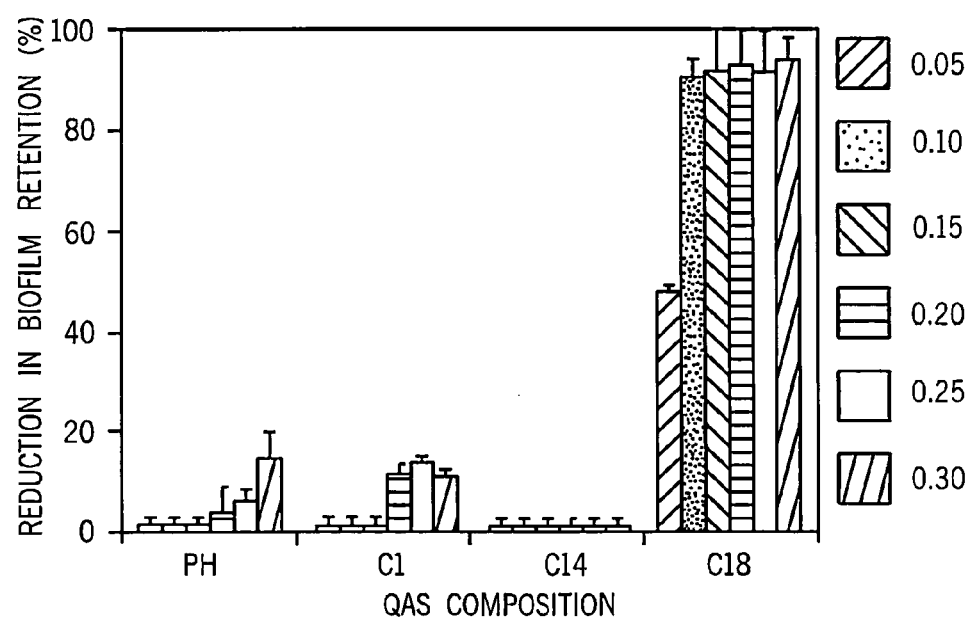

FIG. 20 shows leachate toxicity data obtained using *C. lytica* for coatings that were preleached for 14 days. Of the 72 coatings investigated, only two showed high leachate toxicity. As a result, with the exception of aforementioned coatings exhibiting leachate toxicity, variations in biofilm retention, shown in FIG. 21, can be attributed to differences in coating surface characteristics. The results displayed in FIG. 21 clearly show that coatings based on the C18 QAS functionality were antifouling with respect to *C. lytica*. All of the coatings containing a C18 QAS concentration of 0.10 moles/ kg of PDMS and higher showed a major reduction in biofilm retention. For example, all of the C18 QAS-based coatings derived from the highest molecular weight silanol-terminated PDMS, 49K-PDMS, and possessing a QAS concentration of 0.10 moles/kg of PDMS and higher displayed a greater than 90 percent reduction in C. lytica biofilm retention. This result suggests that C18 QAS moieties were available at the coating surface and were effective toward rupturing the cell wall of the bacterium.

Figure 22A:
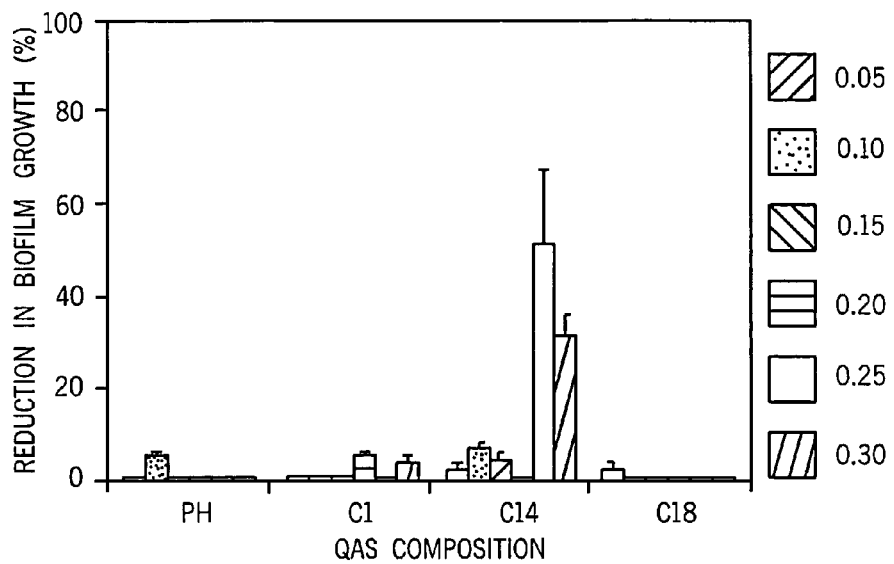
FIG. 22 shows leachate toxicity results for coatings derived from (A) 2K-PDMS, (B) 18K-PDMS, and (C) 49K-PDMS, using *N. incerta*; each data point is the mean of three replicates and error bars represent one standard deviation.
Figure 22B:
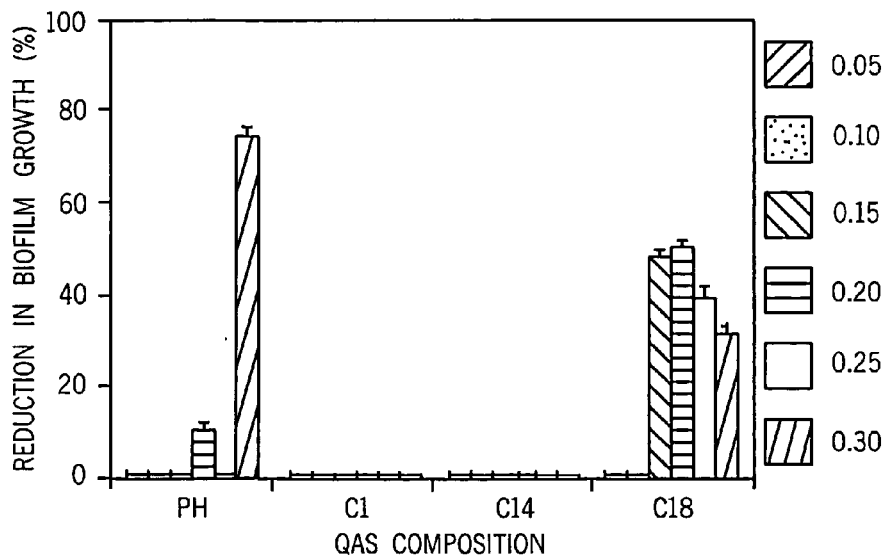
Figure 22C:
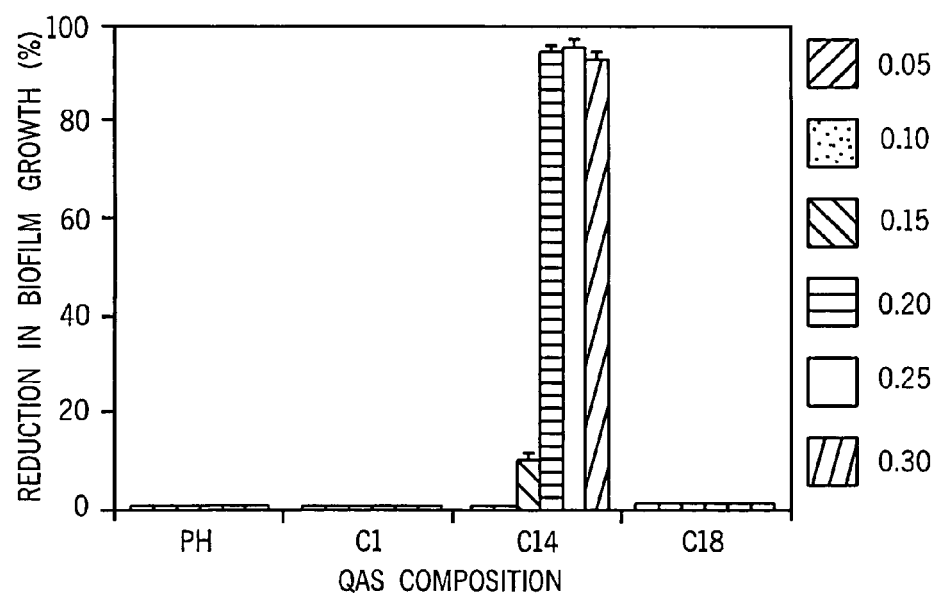
Figure 23A:
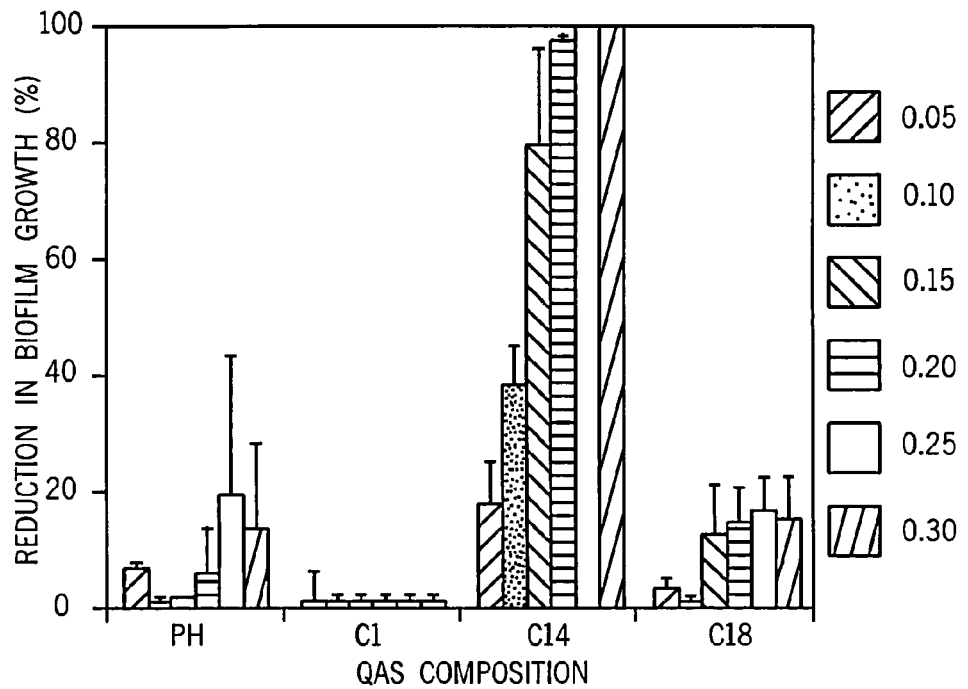
FIG. 23 shows *N. incerta* biofilm growth results for coatings derived from (A) 2K-PDMS, (B) 18K-PDMS, and (C) 49K-PDMS; each data point is the mean of three replicates, error bars represent one standard deviation, and "*" indicates that the sample showed leachate toxicity.
Figure 23B:
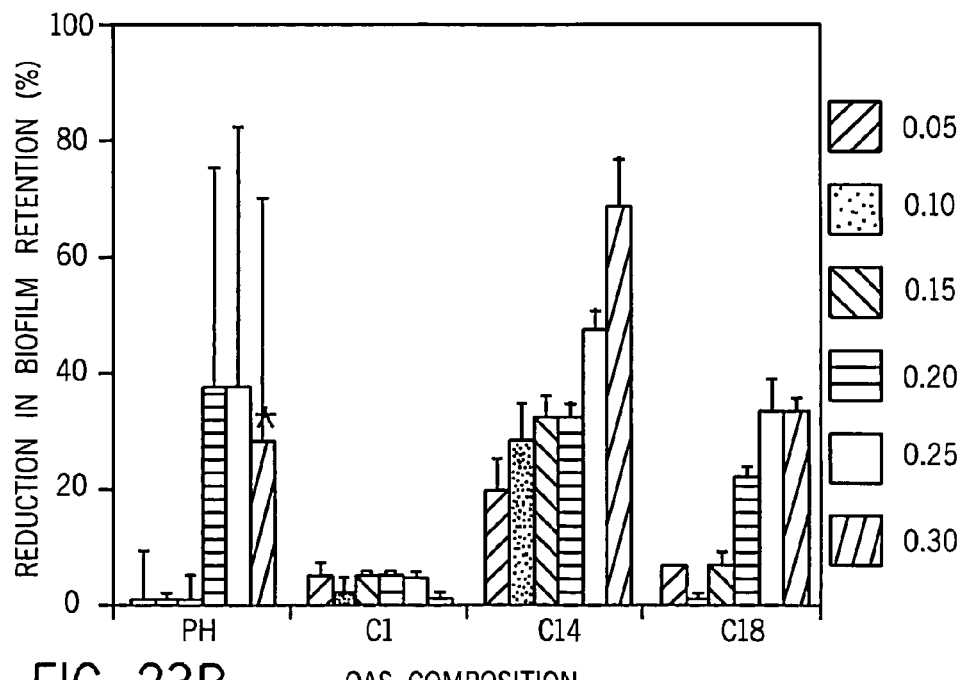
Figure 23C:
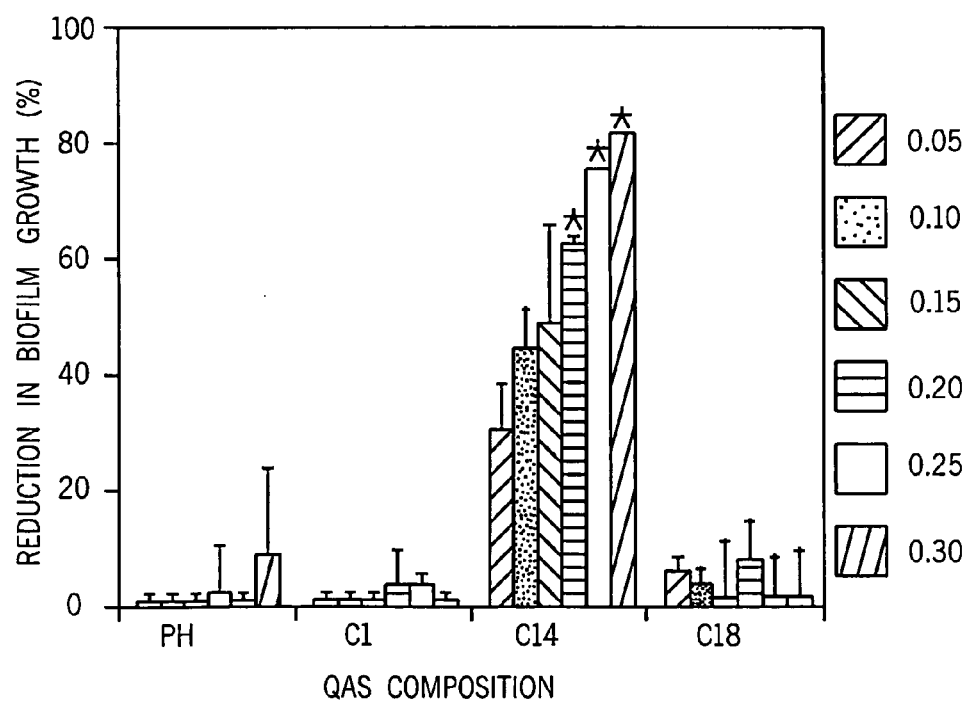

FIGS. 22 and 23 display results obtained with the N. incerta leachate toxicity and biofilm growth assays, respectively. Interestingly, the C18 QAS-based coatings that showed antimicrobial activity toward C. lytica were not effective toward inhibiting N. incerta biofilm growth. However, a major reduction in biofilm growth was observed for some coatings based on C14 QAS moieties. For example, coating 2K-C14-0.20 displayed a 98 percent reduction in N. incerta biofilm growth (FIG. 23) and no leachate toxicity (FIG. 22).

The fact that the lower molecular weight, shorter alkyl chain QAS moieties, Cl and Ph, did not show antimicrobial behavior may be due to a low concentration of the QAS moieties at the surface and/or lower effectiveness of the shorter alkyl chain QAS moieties toward cell membrane disruption. As shown in FIG. 17 and Table 13, the relatively low surface roughness and surface heterogeneity exhibited by coatings 18K-Cl-0.20 and 18K-Ph-0.20 indicates a low level of QAS moieties at the coating surface.

Fouling-Release.

For long-term performance as a marine coating, the QAS-functional coatings of interest will need to have good fouling-release characteristics since long-term ocean immersion will most likely result in the formation of a thin layer of absorbed molecular species or dead microorganisms which may shield the QAS moieties from colonizing microorganisms, spores, and larvae. The fouling-release or surface cleanability of the coatings must be sufficiently adequate to allow for easy removal of the adsorbed/attached moieties to reactivate antimicrobial activity.

A well established fouling-release measurement method based on Ulva sporelings was used to characterize fouling-release performance of a subset of the coatings investigated. Fouling-release performance of eighteen QAS-functional coatings was measured and compared to four reference coatings, namely, IS, DC 3140, T2, and Pu (Table 9). IS is a commercially-available siloxane fouling-release coating designed for ship hulls that has been qualified for use by the United States Navy and shown to exhibit good release of Ulva sporelings.

Figure 24:
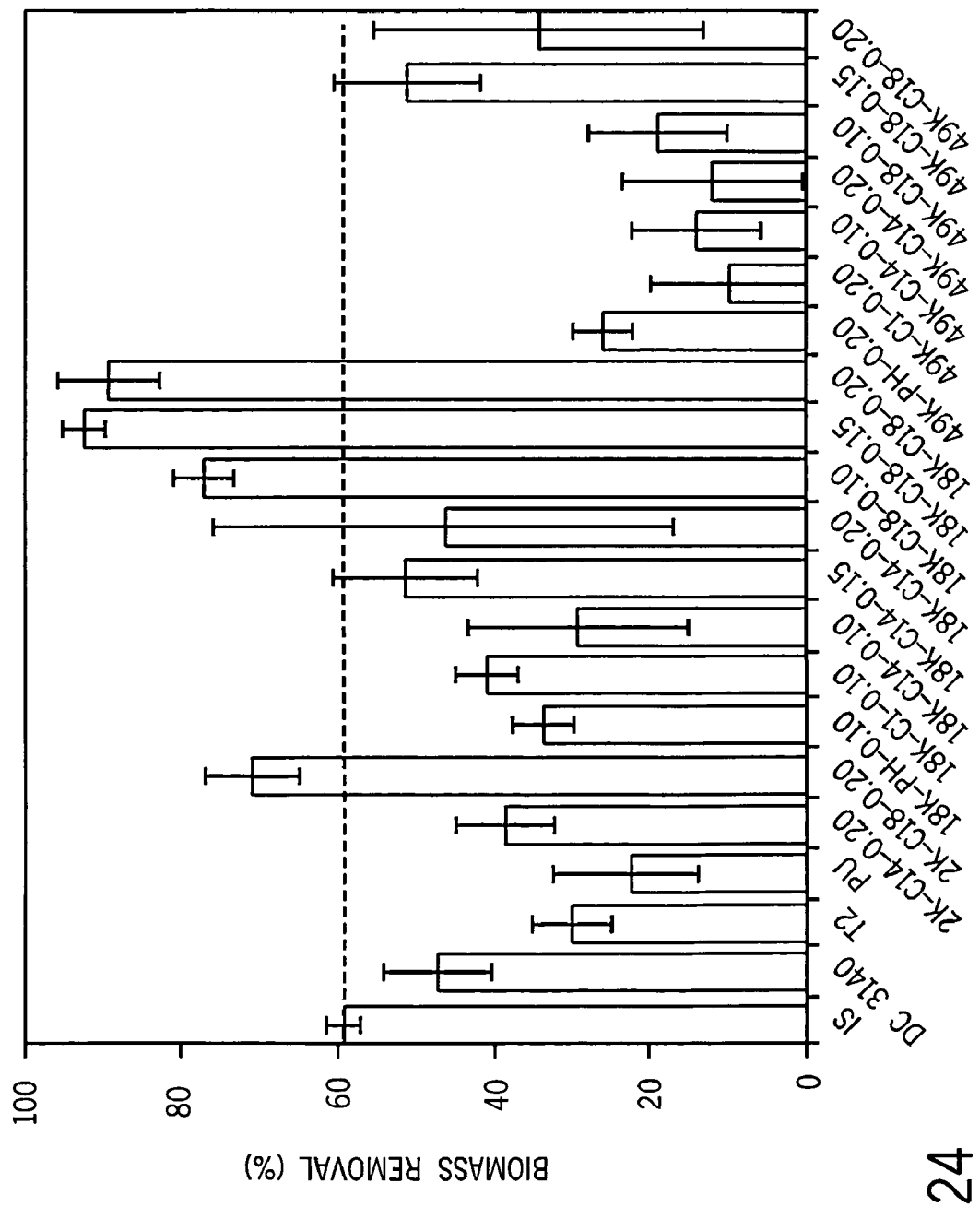
FIG. 24 shows *Ulva* sporeling removal at an impact pressure of 89 kPa; each point is the mean of six replicates, error bars show 95% confidence limits derived from arcsine transformed data, and the dashed line shows mean percent removal from IS.
Figure 25:
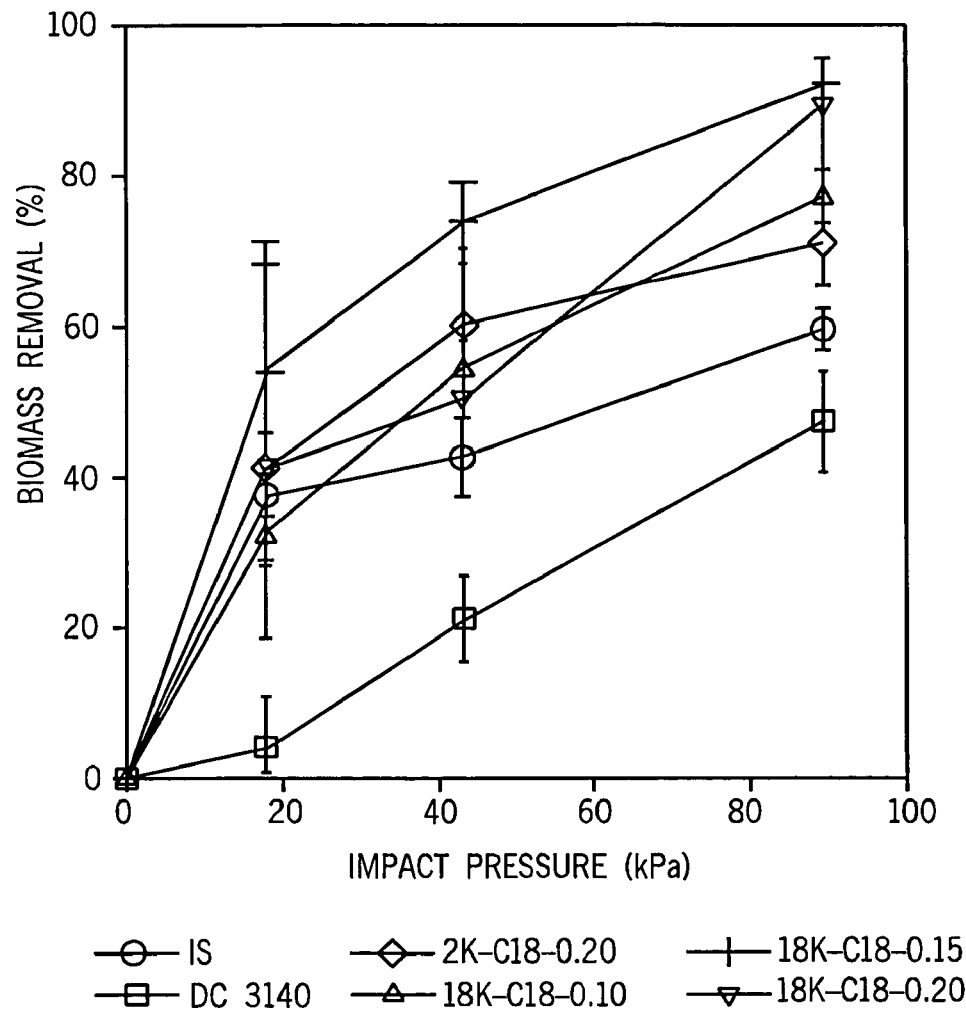
FIG. 25 shows *Ulva* sporeling removal as a function of impact pressure; each point is the mean of six replicates, and error bars show 95% confidence limits derived from arcsine transformed data.

FIG. 24 displays removal of Ulva sporeling biomass after water jetting at 89 kPa of impact pressure. Four of the QAS-functional coatings showed higher removal of Ulva sporelings than IS. Coatings 2K-C18-0.20, 18K-C18-0.10, 18K-C18-0.15, and 18K-C18-0.20 showed Ulva sporeling removal of 70%, 75%, 90%, and 90%, respectively, compared to 60% removal for IS. Removal characteristics of these four promising coatings were further investigated by conducting biomass removal measurements at different impact pressures, as shown in FIG. 25. All four of the QAS-functional coatings displayed better Ulva sporeling removal than IS at essentially all impact pressures.

With regard to coating composition, all four of the best performing coatings were based on C18 QAS groups. In addition, three out of the four best performing coatings were based on the 18K-PDMS. Considering the results obtained for coating surface property characterization, high Ulva sporeling removal correlates with high coating surface heterogeneity. Coatings based on C18 QAS groups and 18K-PDMS were found to exhibit the highest surface heterogeneity and nano-roughness as indicated by AFM measurements and water CAH measurements. A similar correlation was shown for surfaces constructed from amphiphilic block copolymers which had superior release of Ulva sporelings compared to those constructed from either of the individual hydrophilic or hydrophobic components.

The introduction of QAS moieties into moisture-curable polysiloxanes was found to enable the generation of coatings which have both antifouling character and enhanced fouling-release. Compositional variables that resulted in the lowest surface energies were found to possess the highest surface micro-roughness.

Antifouling activity was found to be strongly dependent on QAS composition. For the marine bacterium, C. lytica, the QAS with the longest alkyl chain (C18) was found to be very effective while only the C14-based QAS was effective toward inhibiting N. incerta biofilm formation. With regard to fouling-release, several coatings based on the C18 QAS exhibited higher Ulva sporeling removal than the commercially-available fouling-release coating, IS. The coatings that showed the best fouling-release also possessed the highest surface nano-roughness suggesting a correlation between nano-roughness and fouling-release.

Additional Examples

Additional field tests were conducted with a number of panels coating with examples of the present coating incorporating a C18-QAS (prepared by the methods described herein). The compositions of the components used to produce these coatings are summarized in Table 15. Coatings A3, A5 and A7 had previously showed excellent release performance (comparable to the commercial Intersleek silicone coating) in earlier testing. Earlier testing had also suggested that organism growth may be significantly reduced on coatings A7, A8 and A11 compared to commercial standards. Previous work had also suggested that the optimum amount of silica filler in order to obtain enhanced foul-release properties may be about 10 wt. %.

TABLE 15

| Sample ID | Silanol-PDMS-MW 18000 (gm) | Silanol-PDMS-MW 49000 (gm) | Silanol-fluoro-PDMS (gm) | C18-QAS (moles/100 g PDMS) | Silica filler (gm) |
| --- | --- | --- | --- | --- | --- |
| A1 | 100.0 | 0.0 | 0.0 | 0.02 | 0.0 |
| A2 | 0.0 | 100.0 | 0.0 | 0.02 | 0.0 |
| A3 | 100.0 | 0.0 | 0.0 | 0.02 | 10.0 |
| A4 | 85.0 | 0.0 | 15.0 | 0.02 | 10.0 |
| A5 | 70.0 | 0.0 | 30.0 | 0.02 | 10.0 |
| A6 | 0.0 | 100.0 | 0.0 | 0.02 | 10.0 |
| A7 | 0.0 | 85.0 | 15.0 | 0.02 | 10.0 |
| A8 | 0.0 | 70.0 | 30.0 | 0.02 | 10.0 |
| A9 | 0.0 | 100.0 | 0.0 | 0.02 | 20.0 |
| A10 | 0.0 | 85.0 | 15.0 | 0.02 | 20.0 |
| A11 | 0.0 | 70.0 | 30.0 | 0.02 | 20.0 |

Fouling Resistance Rating on Experimental Coatings

Figure 26:
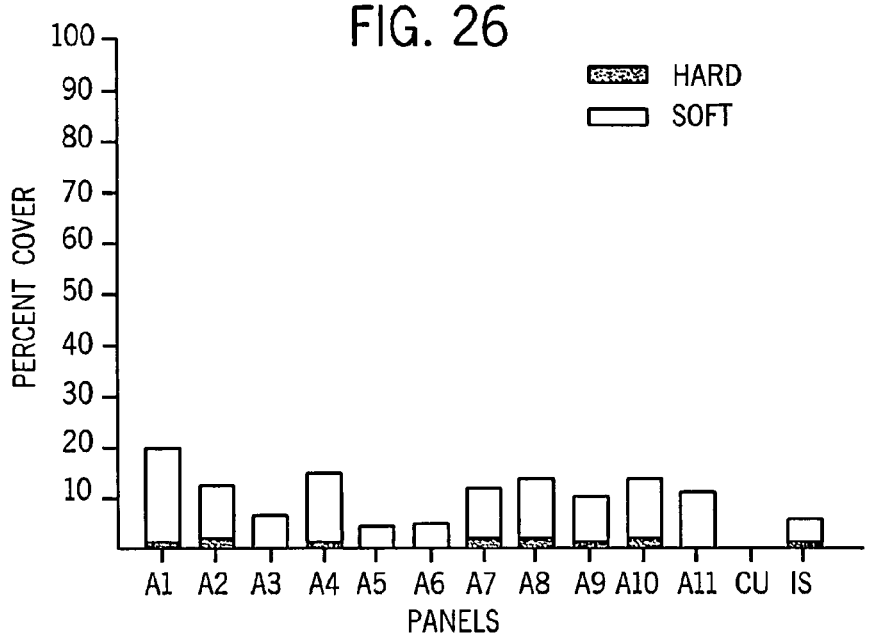
FIG. 26 shows the percent cover by fouling organisms on panels coated with the present coatings by hard and soft macrofouling after 48 days of submersion under marine conditions.

After the coated panels characterized in Table 15 were submerged for 48 days at a test site in Pearl Harbor, Hi., the percent coverage of the coated panels by hard and soft microorganisms was determined. The results are summarized in Table 16 below and in FIG. 26.

Foul-Resistance Rating (FR Rating)

The foul resistance was estimated from the percent of the intact area of the coating covered by fouling organisms. Fouling was ignored on portions of the panel with coating defects.

Panels free of fouling, or for which only algal spores or other biological slimes were present, were awarded a Foul-Resistance Rating (FRRATE) of 100. Panels fouled only by immature forms (e.g., newly settled organisms—'incipient fouling') receive a FR RATE of 95, regardless of the abundance of these organisms. If mature foulers were present, the percent cover of each type of fouling organism was estimated. A point-intercept method was used to determine the extent of fouling on the coatings.

TABLE 16

| Coat | Mean FRRATE | Rank |
|---|---|---|
| Cu* | 95.0 | 1 |
| A5 | 89.5 | 2 |
| A6 | 89.2 | 3 |
| IS | 88.2 | 4 |
| A3 | 87.5 | 5 |
| A9 | 83.8 | 6 |
| A11 | 82.5 | 7 |
| A7 | 82.5 | 8 |
| A2 | 81.7 | 9 |
| A8 | 80.4 | 10 |
| A10 | 80.0 | 11 |
| A4 | 79.4 | 12 |
| A1 | 75.0 | 13 |

*Copper containing commercial coating for comparison.

Ease of Removal of Fouling from Test Coatings

After 48 days of submersion, force gauge tests were conducted on the experimental coatings to remove tubeworms (*Hydroides elegans*) (see Table 17). Untransformed, mean force data required to remove tubeworms (*Hydroides elegans*) from the experimental coatings is shown in Table 17 below.

The Mean Force Rank for ease of removal of tubeworms (*Hydroides elegans*) for panels coated with the experimental coatings of Table 15 is shown in Table 17. Tubeworms were removed with the least force on the A5 coatings and required the most force on the A3 coatings. The minimum force required to remove the tubeworms from the experimental panels ranged from a low of 126.9 kPa for coating A5 to 317.28 for coating A3. The commercial Intersleek silicone coating ("IS") was used as a control and was ranked fifth for ease of removal of the tubeworms. Coatings A5, A8, A7, and A9 all preformed better than the IS coatings (see results summarized in Table 17).

TABLE 17

| Panel | Mean Force kPa | Rank |
|---|---|---|
| A5 | 126.9 | 1 |
| A8 | 155.3 | 2 |
| A7 | 172.67 | 3 |
| A9 | 199.68 | 4 |
| IS | 206.31 | 5 |
| A1 | 208.75 | 6 |
| A2 | 212.12 | 7 |
| A6 | 212.17 | 8 |
| A11 | 219.93 | 9 |
| A10 | 246.06 | 10 |
| A4 | 304.98 | 11 |
| A3 | 317.28 | 12 |

Photogrid Analysis From Sample Testing for Biofouling after Three Months Exposure in a Marine Environment.

Figure 27:
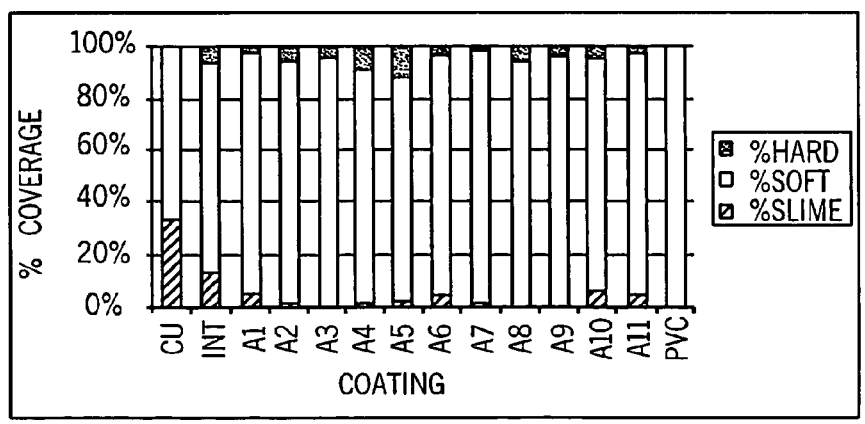
FIG. 27 shows the percent coverage by fouling organisms of panel coated with the present coatings by organism type after three months submersion under marine conditions.

Pictures were analyzed using Photogrid, which randomly assigns 100 points and those points are assigned a category. Percent coverage is then divided into groups by fouling type. Biological slimes include diatoms, initial algal germination and low form algae. Soft foulers are all attached soft organisms and includes algae, cnidarians, arborescent bryozoans, sponges, and tunicates. Hard foulers are all attached hard organisms and includes barnacles, tubeworms, molluscs, and encrusting bryozoans. Copper performed slightly better when looking at percent coverage but had a lot more soft fouling than last month. All the test coatings were similar to the Intersleek control with a majority of soft fouling organisms (see FIG. 27, which shows the percent coverage of panel by organism type). The values are averages of three replicates per panel type. Panel replicates that were previously water jetted were not included in these averages.

Illustrative Embodiments

A number of illustrative embodiments of the present methods and compositions are described below. The embodiments described are intended to provide illustrative examples of the present methods and compositions and are not intended to limit the scope of the invention.

In one embodiment, a substrate (A) may have an antifouling coating on its surface, and the coating may comprise a polymeric material which includes tetraalkyl-substituted quaternary amino functionalized cross-linked polysiloxane.

In another embodiment, the coated substrate (B) can include the quaternary amino functionalized cross-linked polysiloxane, which may be prepared by reacting a mixture which includes alkoxysilyl functionalized quaternary amine and silanol terminated polysiloxane. In the coated substrate of embodiment B, the mixture may further comprise alkyltriacyloxysilane. In the coated substrate of embodiment B, the mixture may further comprise a tetra-functional acyloxysilane and/or alkoxysilane. In the coated substrate of embodiment B, the mixture may further comprise a trifunctional silane in which the reactive functionality is selected from the group that may consist of alkoxysilane, acyloxysilane, silazane, halosilane, and ketoxime-based silane. In the coated substrate of embodiment B, the mixture may further comprise a tetra-functional silane in which the reactive functionality may be selected from the group consisting of alkoxysilane, acyloxysilane, silazane, halosilane, and ketoxime-based silane.

In another embodiment, the coated substrate (C) may include quaternary amino functionalized cross-linked polysiloxane that may be prepared by reacting a mixture which may include silyl functionalized quaternary amine and polysiloxane with reactive terminal groups. In the coated substrate of embodiment C, the silyl functionalized quaternary amine may includes a reactive functionality selected from the group that may consist of alkoxysilane, acyloxysilane, silazane, halosilane, and ketoxime-based silane. In the coated substrate of embodiment C, the polysiloxane with reactive terminal groups may include a reactive functionality selected from the group that may consist of silanol, alkoxysilane, acyloxysilane, silazane, halosilane, and ketoxime-based silane.

In another embodiment, the coated substrate (D) can include quaternary amino functionalized cross-linked polysiloxane that may be prepared by reacting a mixture which may include alkoxysilyl functionalized quaternary amine, silanol terminated polysiloxane, and alkyltriacyloxysilane.

In another embodiment, the coated substrate (E) can include the alkoxysilyl functionalized quaternary amine

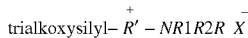

where R1 and R2 may be lower alkyl groups, R may be an alkyl group having 5 to 25 carbon atoms, R' may be a linker group, such as an alkylene and/or benzylidene group, and X may be a halide. In the coated substrate of embodiment E, R' may be ethylene and/or propylene, R1 and R2 may be methyl, benzyl and/or ethyl, and X may be chloride and/or bromide. In the coated substrate of embodiment E, R' may be ethylene, propylene and/or benzylidene. In the coated substrate of embodiment E, R1 and R2 may be methyl; and X may be chloride. In the coated substrate of embodiment E, R may be an n-alkyl group having 5 to 25 carbon atoms. In the coated substrate of embodiment E, R may be an n-alkyl group having at least 10 carbon atoms. In the coated substrate of embodiment E, R may be an n-alkyl group having no more than 20 carbon atoms. In the coated substrate of embodiment E, R may be an n-alkyl group having 12 to 20 carbon atoms. In the coated substrate of embodiment E, R may be an n-alkyl group having 12 to 16 carbon atoms. In the coated substrate of embodiment E, R may be an n-alkyl group having 16 to 20 carbon atoms. In the coated substrate of embodiment E, the alkoxysilyl functionalized quaternary amine may include a trialkoxysilyl group having no more than 6 carbon atoms. In the coated substrate of embodiment E, the alkoxysilyl functionalized quaternary amine may include a trimethoxysilyl group. In the coated substrate of embodiment E, the alkyltriacyloxysilane may be an alkyltriacetoxysilane. In the coated substrate of embodiment E, the alkyltriacyloxysilane may include methyltriacetoxysilane.

In the coated substrate of embodiment D, the silanol terminated polysiloxane may be a silanol terminated polydialkylsiloxane (e.g., a silanol terminated polydimethylsiloxane), and may preferably have a molecular weight of about 1,000 to about 100,000, desirably have a molecular weight of about 10,000 to about 75,000, and more desirably have a molecular weight of about 15,000 to about 50,000.

In another embodiment, a polymeric material (F) can be prepared by reacting a mixture which may include alkoxysilyl functionalized quaternary amine; silanol terminated polysiloxane; and alkyltriacyloxysilane. In the polymeric material of embodiment F, the mixture may further comprise tetraalkyl ammonium fluoride salt and/or tetraalkyl phosphonium fluoride salt. The polymeric material of embodiment F may be formed from a mixture comprising about 0.001 to 0.05 moles of the alkoxysilyl functionalized quaternary amine per 100 gm of the silanol terminated polysiloxane. The polymeric material of embodiment F may be formed from a mixture comprising about 0.005 to 0.03 moles trialkoxysilyl functionalized quaternary amine per 100 gm of silanol terminated polydialkylsiloxane. The polymeric material of embodiment F may be formed from a mixture comprising about 0.015 to 0.025 moles trialkoxysilyl functionalized quaternary amine per 100 gm of silanol terminated polydimethylsiloxane. In the polymeric material of embodiment F, the trialkoxysilyl functionalized quaternary amine may include an N-C18-alkyl-N,N-dimethylamino group. In the polymeric material of embodiment F, the trialkoxysilyl functionalized quaternary amine may include an N-C14-alkyl-N,N-dimethylamino group. In the polymeric material of embodiment F, the trialkoxysilyl functionalized quaternary amine may include an N—(C16-C20)-n-alkyl-N,N-dimethylamino group. In the polymeric material of embodiment F, the trialkoxysilyl functionalized quaternary amine may include an N—(C12-C16)-n-alkyl-N,N-dimethylamino group.

In another embodiment, a polymeric material (G) may be prepared by reacting a mixture which may include trialkoxysilyl functionalized quaternary amine, silanol terminated polydialkylsiloxane, and alkyltriacyloxysilane.

In another embodiment, a polymeric material (H) may be prepared by reacting a mixture which may include trimethoxysilyl functionalized quaternary amine, silanol terminated polydialkylsiloxane, and methyltriacetoxysilane.

In another embodiment, an antimicrobial polymer coating (I) can comprise quaternary amino functionalized cross-linked polysiloxane and/or salts thereof. In the polymer coating of embodiment I, the quaternary amino functionalized cross-linked polysiloxane may be prepared by reacting a mixture which may include alkoxysilyl functionalized quaternary amine, silanol terminated polysiloxane, and alkyltriacyloxysilane. In the polymer coating of embodiment I, the quaternary amino functionalized cross-linked polysiloxane may include silyl functionalized quaternary amino moieties, which may include an N—(C10-C25)-n-alkyl-N,N-dimethylamino group. In the polymer coating of embodiment I, the quaternary amino functionalized cross-linked polysiloxane may include silyl functionalized quaternary amino moieties, which may include an N—(C12-C16)-n-alkyl-N,N-dimethylamino group. In the polymeric material of embodiment I, the mixture may further comprise tetrabutyl ammonium fluoride.

In another embodiment, an amino functionalized cross-linked polysiloxane (J) may be prepared by reacting a mixture, which may include alkoxysilyl functionalized quaternary amine, silanol terminated polysiloxane, and alkyltriacyloxysilane.

Another embodiment provides a method (K) of coating a substrate, which may comprise application of a mixture to the substrate, where the mixture may include alkoxysilyl functionalized quaternary amine, silanol terminated polysiloxane, and alkyltriacyloxysilane, to the substrate.

Another embodiment provides a method (L) of inhibiting biofilm growth on a substrate surface, comprising coating the surface with a polymeric material that can include an amino functionalized cross-linked polysiloxane, which may be prepared by reacting a mixture which may include alkoxysilyl functionalized quaternary amine, silanol terminated polysiloxane and alkyltriacyloxysilane. In the method of embodiment L, the alkoxysilyl functionalized quaternary amine may include trialkoxysilyl functionalized quaternary amine that may have an N—(C12-C16)-n-alkyl-N,N-dimethylamino group. In the method of embodiment L, the polymeric material may be formed from a mixture comprising at least about 0.015 moles and, more desirably, at least about 0.02 moles alkoxysilyl functionalized quaternary amine per 100 gm of the silanol terminated polysiloxane. In the method of embodiment L, the polymeric material may be formed from a mixture comprising at least about 0.02 moles alkoxysilyl functionalized quaternary amine per 100 gm of the silanol terminated polysiloxane, and the alkoxysilyl functionalized quaternary amine may include trimethoxysilyl functionalized quaternary amine having an N—(C14)-n-alkyl-N,N-dimethylamino group.

Another embodiment provides a method (M) of inhibiting biofilm retention on a substrate surface comprising coating the surface with a polymeric material that can include an amino functionalized cross-linked polysiloxane, which may be prepared by reacting a mixture which may include alkoxysilyl functionalized quaternary amine, silanol terminated polysiloxane and alkyltriacyloxysilane. In the method of embodiment M, the alkoxysilyl functionalized quaternary amine can include trialkoxysilyl functionalized quaternary amine having an N—(C16-C20)-n-alkyl-N,N-dimethylamino group. In the method of embodiment M, the polymeric material can be formed from a mixture comprising at least about 0.01 moles alkoxysilyl functionalized quaternary amine per 100 gm of the silanol terminated polysiloxane. In the method of embodiment M, the alkoxysilyl functionalized quaternary amine may include trialkoxysilyl functionalized quaternary amine having an N-C18-alkyl-N,N-dimethylamino group, and the polymeric material may comprise at least about 0.01 moles alkoxysilyl functionalized quaternary amine per 100 gm of the silanol terminated polysiloxane.

In another embodiment, the coated substrate (N) can include the silanol terminated polysiloxane having the formula

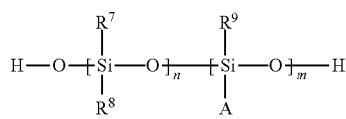

wherein $R^7$, $R^8$, and $R^9$ may be independently alkyl, A may be an alkyl and/or alkoxy group, n may be 0 to 5000, m may be 0 to 2000, and n+m may be at about least 10, and more desirably at least about 25. Commonly, n is at least about 10 and n+m is at least about 20. In the coated substrate of embodiment N, the silanol terminated polysiloxane may have a molecular weight of at least about 500 g/mol. In the coated substrate of embodiment N, the silanol terminated polysiloxane may have a molecular weight of no more than about 50,000 g/mol. In the coated substrate of embodiment N, A may be an alkyl group. In the coated substrate of embodiment N, the silanol terminated polysiloxane may be a silanol terminated polydimethylsiloxane. In the coated substrate of embodiment N, the silanol terminated polysiloxane may be a silanol terminated polyalkylsiloxane.

In another embodiment, a polymeric material (O) may be prepared by reacting a mixture which may include trimethoxysilyl functionalized quaternary amine, silanol terminated polydimethylsiloxane, and methyltriacetoxysilane.

In another embodiment, the coated substrate (P) of embodiment O, the trimethoxysilyl functionalized quaternary amine may include

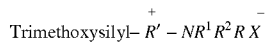

where $R^1$ and $R^2$ may be methyl, R may be an n-alkyl group having 5 to 25 carbon atoms, R' may be a propylene and/or ethylene group, and X may be a chloride and/or bromide. In the coated substrate of embodiment O or P, the silanol terminated polydimethylsiloxane may have a molecular weight of about 1,000 to 50,000.

In the polymeric material of embodiment F, the trialkoxysilyl functionalized quaternary amine may include a compound of the formula:

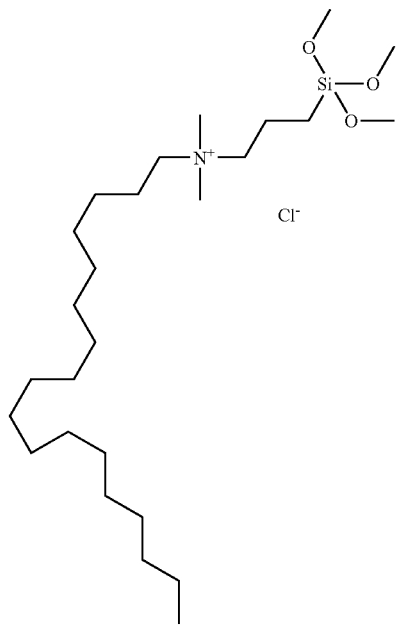 [SMILES: CCCCCCCCCCCCCCCCCC[N+](C)(C)CCC[Si](OC)(OC)OC ; [Cl-]]

In the coated substrate of embodiment E, the polymeric material may be prepared by reacting a mixture that can comprise silanol terminated polysiloxane and quaternary aminosiloxane of the following formula (wherein R is an alkyl group having 10 to 25 carbon atoms and, more desirably, is an n-alkyl group 12 to 20 carbon atoms):

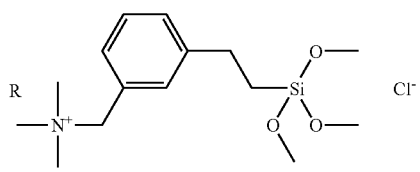

In the coated substrate of embodiment E, the polymeric material can be prepared by reacting a mixture that may comprise silanol terminated polysiloxane; and quaternary aminosiloxane of the following formula (wherein R is an alkyl group having 10 to 25 carbon atoms and, more desirably, is an n-alkyl group 12 to 20 carbon atoms):

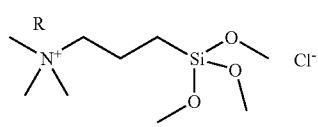

In the polymeric material of embodiment F, the trialkoxysilyl functionalized quaternary amine can include a compound of the formula:

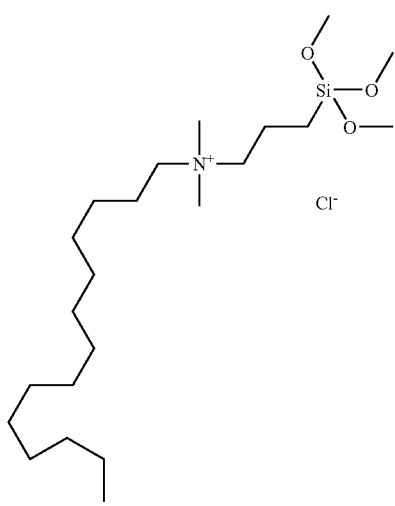 [SMILES: CCCCCCCCCCCCCC[N+](C)(C)CCC[Si](OC)(OC)OC ; [Cl-]]

In another embodiment, a polymeric material (Q) may include quaternary amino functionalized cross-linked polysiloxane.

In another embodiment, the polymeric material (R) can include the quaternary amino functionalized cross-linked polysiloxane prepared by reacting a mixture which includes alkoxysilyl functionalized quaternary amine and silanol terminated polysiloxane. In the polymeric material of embodiment R, the mixture can further comprise alkyltriacyloxysilane. In the polymeric material of embodiment R, the mixture may further comprise a tetra-functional acyloxysilane and/or alkoxysilane. In the polymeric material of embodiment R, the mixture may further comprise a trifunctional silane in which the reactive functionality is selected from the group that can consist of alkoxysilane, acyloxysilane, silazane, halosilane, and ketoxime-based silane. In the polymeric material of embodiment R, the mixture further comprises a tetra-functional silane in which the reactive functionality may be selected from the group consisting of alkoxysilane, acyloxysilane, silazane, halosilane, and ketoxime-based silane.

In another embodiment, the polymeric material (S) may include quaternary amino functionalized cross-linked polysiloxane, which may be prepared by reacting a mixture which can include silyl functionalized quaternary amine and polysiloxane with reactive terminal groups. In the polymeric material of embodiment S, the silyl functionalized quaternary amine can include a reactive functionality selected from the group that may consist of alkoxysilane, acyloxysilane, silazane, halosilane, and ketoxime-based silane. In the polymeric material of embodiment S, the polysiloxane with reactive terminal groups may include reactive functionality selected from the group that may consist of alkoxysilane, acyloxysilane, silazane, halosilane, and ketoxime-based silane.

Another embodiment provides a method (T) of facilitating biofilm removal on a substrate surface, comprising coating the surface with a polymeric material that includes an amino functionalized cross-linked polysiloxane, prepared by reacting a mixture, which may include alkoxysilyl functionalized quaternary amine, silanol terminated polysiloxane and alkyltriacyloxysilane. In the method of embodiment T, the alkoxysilyl functionalized quaternary amine can include trialkoxysilyl functionalized quaternary amine having an N—(C16-C20)-n-alkyl-N,N-dimethylamino group. In the method of embodiment T, the polymeric material may be formed from a mixture comprising at least about 0.01 moles and, more desirably, at least about 0.02 moles of alkoxysilyl functionalized quaternary amine per 100 gm of the silanol terminated polysiloxane. In the method of embodiment T, the silanol terminated polysiloxane may have a molecular weight of no more than about 35,000. In the method of embodiment T, the polymeric material may be formed from a mixture comprising at least about 0.01 moles and, more desirably, at least about 0.02 moles of alkoxysilyl functionalized quaternary amine per 100 gm of the silanol terminated polysiloxane; the alkoxysilyl functionalized quaternary amine may include trimethoxysilyl functionalized quaternary amine having an N—(C18)-n-alkyl-N,N-dimethylamino group, and the silanol terminated polysiloxane may have a molecular weight of about 10,000 to 30,000.

In the polymeric material (U), the alkoxysilyl functionalized quaternary amine may include a N,N-bis(trialkoxysilylalkyl)-N,N-dialkylamine. In the polymeric material, the alkoxysilyl functionalized quaternary amine may include a N,N-bis(trialkoxysilylalkyl)-N,N-dialkylamine where the trialkoxysilylalkyl group commonly comprises a suitably substituted lower alkyl group, preferably C2-C6. In the polymeric material, the N,N-bis(trialkoxysilylalkyl)-dialkylamine may include a N,N-bis(trialkoxysilylalkyl)-dialkylamine, where the trialkoxysilylalkyl comprises a suitably substituted lower alkyl group, preferably C2-C6, which is often a linear alkyl group. In the polymeric material, the N,N-bis(trialkoxysilylalkyl)-dialkylamine may include an N,N-bis(n-trialkoxysilylalkyl)-N—(C4-C15)-alkyl-alkylamine. In the polymeric material, the N,N-bis(trialkoxysilylalkyl)-dialkylamine may include a N,N-bis(3-trimethoxysilylpropyl)-N—(C4-C15)-n-alkyl alkylamine and/or N,N-bis(2-trimethoxysilylethyl)-N—(C4-C15)-n-alkyl alkylamine. In the polymeric material, the N,N-bis(trialkoxysilylalkyl)-dialkylamine may include a N,N-bis(3-trimethoxysilylpropyl)-N—(C4-C15)-n-alkyl-methylamine and a N,N-bis(2-trimethoxysilylethyl)-N—(C4-C15)-n-alkyl-methylamine.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

What is claimed is:

1. A polymeric material formed by reacting a mixture comprising:
   (a) alkoxysilyl functionalized quaternary amine, wherein the alkoxysilyl functionalized quaternary amine comprises alkoxysilyl functionalized quaternary amine having an N—(C16-C20)-n-alkyl-N,N-dimethylamino group;
   (b) silanol terminated polysiloxane; and
   (c) trifunctional silane, tetra-functional silane, or a mixture thereof;

wherein the mixture comprises about 0.001 to 0.05 moles of the alkoxysilyl functionalized quaternary amine per 100 gm of the silanol terminated polysiloxane.

2. The polymeric material of claim 1, wherein the alkoxysilyl functionalized quaternary amine comprises trialkoxysilyl functionalized quaternary amine.

3. The polymeric material of claim 1, wherein the trifunctional silane comprises alkyltriacyloxysilane.

4. The polymeric material of claim 1, wherein the trifunctional silane comprises acyloxysilane, ketoxime-based silane, or a mixture thereof.

5. The polymeric material of claim 1, wherein the alkoxysilyl functionalized quaternary amine comprises bis-(trialkoxysilyl functionalized)-quaternary amine.

6. The polymeric material of claim 1 wherein the alkoxysilyl functionalized quaternary amine comprises trialkoxysilyl functionalized, tetraalkyl-quaternary amine.

7. The polymeric material of claim 1 wherein the alkoxysilyl functionalized quaternary amine comprises N,N-bis(trialkoxysilylalkyl)-N,N-dialkylamine.

8. The polymeric material of claim 1 wherein the silanol terminated polysiloxane has a formula

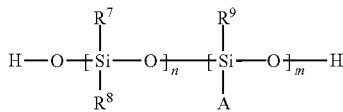

wherein $R^7$, $R^8$, and $R^9$ are independently alkyl, A is alkoxy; n is 10 to 5000; m is 0 to 2000; and n+m is at least 20.

9. A substrate having an antifouling coating on a surface thereof;
   wherein the coating comprises a cross linked polymer formed by reacting a mixture comprising trifunctional silane, tetra-functional silane, or a mixture thereof; alkoxysilyl functionalized quaternary amine; and silanol terminated polysiloxane;
   wherein the mixture comprises about 0.001 to 0.05 moles of the alkoxysilyl functionalized quaternary amine per 100 gm of the silanol terminated polysiloxane; and
   the alkoxysilyl functionalized quaternary amine comprises alkoxysilyl functionalized quaternary amine having an N—(C16-C20)-n-alkyl-N,N-dimethylamino group.

10. A substrate having an antimicrobial polymer coating on a surface thereof, the coating comprising:
   quaternary amino functionalized cross-linked polysiloxane formed by reacting a mixture comprising:
      trifunctional silane, tetra-functional silane, or a mixture thereof;
      alkoxysilyl functionalized quaternary amine; and
      silanol terminated polysiloxane;
   wherein the mixture comprises about 0.001 to 0.05 moles of the alkoxysilyl functionalized quaternary amine per 100 gm of the silanol terminated polysiloxane; and
   the alkoxysilyl functionalized quaternary amine comprises alkoxysilyl functionalized quaternary amine having an N—(C16-C20)-n-alkyl-N,N-dimethylamino group.

11. The polymeric material of claim 1 wherein the mixture further comprises a filler.

12. The polymeric material of claim 11 wherein the filler comprises silica.

13. The polymeric material of claim 1 wherein the mixture further comprises about 5 to 15 wt. % silica.

14. The polymeric material of claim 8 wherein m is 0; and the silanol terminated polysiloxane has a molecular weight of about 1,000 to 50,000.

15. The polymeric material of claim 1 wherein the mixture comprises at least 0.015 moles of the alkoxysilyl functionalized quaternary amine per 100 gm of the silanol terminated polysiloxane.

16. The polymeric material of claim 1 wherein the alkoxysilyl functionalized quaternary amine further comprises a trialkoxysilyl functionalized quaternary amine having an N—(C12-C14)-n-alkyl-N,N-dimethylamino group.

17. The polymeric material of claim 8 wherein the silanol terminated polysiloxane has a molecular weight of about 1,000 to 50,000; m is 0; and $R^7$, $R^8$, and $R^9$ are methyl;
   alkoxysilyl functionalized quaternary amine further comprises a trialkoxysilyl functionalized quaternary amine having an N—(C12-C14)-n-alkyl-N,N-dimethylamino group; and
   the trifunctional silane comprises tri-functional acyloxysilane.

18. The polymeric material of claim 17 wherein the alkoxysilyl functionalized quaternary amine comprises a quaternary amine having a formula

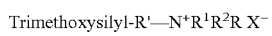

wherein $R^1$ and $R^2$ are methyl; R is an n-alkyl group having 12 to 20 carbon atoms; R' is a propylene and/or ethylene group; and X is chloride and/or bromide.

19. The substrate of claim 9 wherein the silanol terminated polysiloxane has a molecular weight of about 15,000 to 50,000; and $R^7$, $R^8$, and $R^9$ are methyl;
   the alkoxysilyl functionalized quaternary amine comprises a quaternary amine having a formula

wherein $R^1$ and $R^2$ are methyl; R is an n-alkyl group having 16 to 20 carbon atoms; R' is a propylene and/or ethylene group; and X is chloride and/or bromide; and
   the mixture comprises tri-functional acyloxysilane.

20. The substrate of claim 10 wherein the silanol terminated polysiloxane has a molecular weight of about 15,000 to 50,000;
   the alkoxysilyl functionalized quaternary amine comprises a quaternary amine having a formula

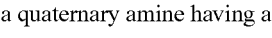

wherein $R^1$ and $R^2$ are methyl; R is an n-alkyl group having 16 to 20 carbon atoms; R' is a propylene and/or ethylene group; and X is chloride and/or bromide; and
   the mixture comprises tri-functional acyloxysilane.

21. The polymeric material of claim 1 wherein the mixture comprises about 0.005 to 0.03 moles of the alkoxysilyl functionalized quaternary amine per 100 gm of the silanol terminated polysiloxane.

22. A cross-linked polymeric material formed by reacting a mixture comprising:
   (a) alkoxysilyl functionalized quaternary amine comprising trialkoxysilyl functionalized quaternary amine having an N—(C16-C20)-n-alkyl-N,N-dimethylamino group; and
   (b) silanol terminated polysiloxane;
   wherein the mixture comprises about 0.001 to 0.05 moles of the alkoxysilyl functionalized quaternary amine per 100 gm of the silanol terminated polysiloxane.

23. The polymeric material of claim 8 wherein the silanol terminated polysiloxane has a molecular weight of about 10,000 to 75,000 and has a formula

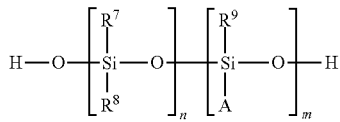

wherein m is 0; and $R^7$ and $R^8$ are methyl.

24. The polymeric material of claim 23 wherein the silanol terminated polydialkylsiloxane has a molecular weight of about 15,000 to about 50,000;

the alkoxysilyl functionalized quaternary amine includes trialkoxysilyl-R'—$N^+R^1R^2R\ X^-$ wherein $R^1$ and $R^2$ are methyl;
R is an alkyl group having 16 to 20 carbon atoms;
R' is a propylene and/or ethylene group; and
X is a halide; and
the mixture comprises 0.01 to 0.03 moles of the alkoxysilyl functionalized quaternary amine per 100 gm of the silanol terminated polysiloxane.

25. The polymeric material of claim 1 wherein the silanol terminated polydialkylsiloxane has a molecular weight of about 15,000 to about 50,000; and the mixture comprises 0.01 to 0.03 moles of the alkoxysilyl functionalized quaternary amine per 100 gm of the silanol terminated polysiloxane.

26. The polymeric material of claim 17 wherein the trifunctional acyloxysilane comprises methyltriacetoxysilane.

27. The polymeric material of claim 19 wherein the trifunctional acyloxysilane is alkyltriacyloxysilane.

28. The polymeric material of claim 20 wherein the trifunctional acyloxysilane is alkyltriacyloxysilane.

* * * * *

UNITED STATES PATENT AND TRADEMARK OFFICE
CERTIFICATE OF CORRECTION

| | | |
|---|---|---|
| PATENT NO. | : 8,372,384 B2 | Page 1 of 1 |
| APPLICATION NO. | : 12/006926 | |
| DATED | : February 12, 2013 | |
| INVENTOR(S) | : Chisholm et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1333 days.

Signed and Sealed this
Sixteenth Day of December, 2014

Michelle K. Lee
*Deputy Director of the United States Patent and Trademark Office*